United States Patent
Tozawa et al.

(12)

(10) Patent No.: US 11,746,357 B2
(45) Date of Patent: Sep. 5, 2023

(54) METHOD FOR PRODUCING HSL PROTEIN HAVING IMPROVED CATALYTIC ACTIVITY FOR 2-OXOGLUTARIC ACID-DEPENDENTLY OXIDIZING 4-HPPD INHIBITOR

(71) Applicants: National Agriculture and Food Research Organization, Tsukuba (JP); SDS Biotech K.K., Tokyo (JP)

(72) Inventors: Yuzuru Tozawa, Saitama (JP); Satomi Takei, Saitama (JP); Masahiro Oshima, Tsukuba (JP); Sakiko Hirose, Tsukuba (JP); Motoshige Kawata, Tsu (JP); Keisuke Sekino, Tokyo (JP); Akihiko Yamazaki, Tokyo (JP)

(73) Assignees: National Agriculture and Food Research Organization, Tsukuba (JP); SDS BIOTECH K.K., Tokyo (JP)

( * ) Notice: Subject to any disclaimer, the term of this patent is extended or adjusted under 35 U.S.C. 154(b) by 310 days.

(21) Appl. No.: 16/485,046

(22) PCT Filed: Feb. 9, 2018

(86) PCT No.: PCT/JP2018/004514
§ 371 (c)(1),
(2) Date: Aug. 9, 2019

(87) PCT Pub. No.: WO2018/147401
PCT Pub. Date: Aug. 16, 2018

(65) Prior Publication Data
US 2020/0048315 A1    Feb. 13, 2020

(30) Foreign Application Priority Data
Feb. 10, 2017 (JP) .................. 2017-023294

(51) Int. Cl.
*C12N 15/82* (2006.01)
*C07K 14/415* (2006.01)
*C12Q 1/6895* (2018.01)

(52) U.S. Cl.
CPC ........ *C12N 15/8274* (2013.01); *C07K 14/415* (2013.01); *C12Q 1/6895* (2013.01)

(58) Field of Classification Search
CPC .................................................. C12N 15/8274
See application file for complete search history.

(56) References Cited

U.S. PATENT DOCUMENTS

| 10,544,425 B2* | 1/2020 | Kato | C12N 15/8274 |
| 2015/0047066 A1* | 2/2015 | Kato | C12N 9/0004 800/260 |
| 2016/0208243 A1* | 7/2016 | Zhang | C12N 15/82 |

FOREIGN PATENT DOCUMENTS

| JP | 2014-011967 A | | 1/2014 | |
| WO | 2012/090950 A1 | | 7/2012 | |
| WO | WO2012/090950 | * | 7/2012 | .............. C12N 15/82 |

OTHER PUBLICATIONS

Communication, dated Aug. 22, 2019, issued in International Application No. PCT/JP2018/004514.
International Search Report for PCT/JP2018/004514 dated May 1, 2018 [PCT/ISA/210].

* cited by examiner

*Primary Examiner* — Mykola V. Kovalenko
(74) *Attorney, Agent, or Firm* — Sughrue Mion, PLLC

(57) ABSTRACT

In order to provide: a method for producing an HSL protein with increased catalytic activity to oxidize a 4-HPPD inhibitor in a 2-oxoglutarate-dependent manner; and a method for producing a plant with increased resistance to a 4-HPPD inhibitor using the method for producing the HSL protein, it has been revealed that, by mutating position 140 to a basic amino acid in an HSL protein, the catalytic activity of the protein to oxidize a 4-HPPD inhibitor in a 2-oxoglutarate-dependent manner can be increased, and an activity of the protein to decompose the inhibitor can be increased.

2 Claims, 16 Drawing Sheets
(1 of 16 Drawing Sheet(s) Filed in Color)
Specification includes a Sequence Listing.

FIG. 12

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL1-mt | I | H | F | T | L | 5 |
| OsHSL1-mt | V | H | F | T | L | 5 |
| OsHSL1-mt | V | H | F | T | L | 5 |
| OsHSL1-mt | V | H | L | S | L | 4 |
| OsHSL1-mt | V | H | F | S | F | 3 |
| OsHSL1-mt | V | F | F | S | F | 3 |
| OsHSL1-mt | V | H | L | S | F | 2 |
| OsHSL1-mt | V | F | L | S | F | 1 |
| OsHSL1-mt | V | K | L | S | F | 1 |
| OsHSL1 (Wild-type) | V | F | L | S | F | ALMOST 0 |

FIG. 13

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL2-mt | I | H | T | C | I | 2 |
| OsHSL2 (Wild-type) | I | H | T | C | F | 0 |

FIG. 14

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| ZmHSL2-mt | L | H | F | P | L | 4.5 |
| ZmHSL2-mt | L | H | Y | P | L | 4 |
| ZmHSL2 (Wild-type) | L | Q | Y | P | L | 3 |

|  | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| SbBSl1-mt | L | H | Y | P | L | 3 |
| SbBSl1 (Wild-type) | L | Q | Y | P | L | 2 |

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL1-mt | V | H | F | T | L | 5 |
| OsHSL1-mt | V | H | L | S | L | 5 |
| OsHSL1-mt | V | H | F | S | F | 5 |
| OsHSL1-mt | V | H | L | S | F | 5 |
| OsHSL1-mt | V | K | L | S | F | 4.5 |
| OsHSL1 (Wild-type) | V | F | L | S | F | 4 |
| OsHSL1-mt | V | F | F | S | F | 3.5 |
| OsHSL1-mt | V | F | L | S | F | 2.5 |
| OsHSL1-mt | V | Q | L | S | F | 2.5 |
| OsHSL1-mt | V | F | F | S | L | 1.5 |

FIG. 17

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL1-mt | V | R | L | S | F | 5 |
| OsHSL1-mt | V | R | L | S | I | 4 |
| OsHSL1-mt | V | H | F | S | F | 4 |
| OsHSL1-mt | V | F | R | S | I | 1 |
| OsHSL1-mt | V | R | L | S | F | 0.5 |
| OsHSL1 (Wild-type) | V | F | L | S | F | ALMOST 0 |

SEQUENCE LISTING

```
<160> NUMBER OF SEQ ID NOS: 43

<210> SEQ ID NO 1
<211> LENGTH: 1056
<212> TYPE: DNA
<213> ORGANISM: Oryza sativa
<220> FEATURE:
<221> NAME/KEY: CDS
<222> LOCATION: (1)..(1056)

<400> SEQUENCE: 1 atg gct gac gag tca tgg agg gcg ccg gcg ata gtg caa gag ctg gcg     48
Met Ala Asp Glu Ser Trp Arg Ala Pro Ala Ile Val Gln Glu Leu Ala
1               5                   10                  15 gca gcc ggc gtc gag gag ccg ccg agc cga tac ctg cta cgg gag aaa     96
Ala Ala Gly Val Glu Glu Pro Pro Ser Arg Tyr Leu Leu Arg Glu Lys
            20                  25                  30 gac cgt tct gac gtc aag ctg gtc gcc gcc gag ctg ccg gag ccc ctc    144
Asp Arg Ser Asp Val Lys Leu Val Ala Ala Glu Leu Pro Glu Pro Leu
        35                  40                  45 ccc gtc gtt gat ctc agc cgg cta gat ggt gcc gag gag gcc acc aag    192
Pro Val Val Asp Leu Ser Arg Leu Asp Gly Ala Glu Glu Ala Thr Lys
    50                  55                  60 ctc agg gtg gct ctg cag aat tgg ggc ttc ttc ctg ctt acc aac cat    240
Leu Arg Val Ala Leu Gln Asn Trp Gly Phe Phe Leu Leu Thr Asn His
65                  70                  75                  80
```

```
gga gta gaa gcc tct ctg atg gac agc gtg atg aac ttg tcg aga gag        288
Gly Val Glu Ala Ser Leu Met Asp Ser Val Met Asn Leu Ser Arg Glu
                85                  90                  95 ttt ttc aac caa cca atc gaa cgg aag caa aaa ttc agc aac ttg atc        336
Phe Phe Asn Gln Pro Ile Glu Arg Lys Gln Lys Phe Ser Asn Leu Ile
            100                 105                 110 gat ggc aag aac ttc cag att caa ggg tat gga act gac cgg gtg gtt        384
Asp Gly Lys Asn Phe Gln Ile Gln Gly Tyr Gly Thr Asp Arg Val Val
        115                 120                 125 acc caa gat cag atc ctg gac tgg tct gat cgg ttg cat ctc aga gtt        432
Thr Gln Asp Gln Ile Leu Asp Trp Ser Asp Arg Leu His Leu Arg Val
    130                 135                 140 gaa ccc aag gag gag caa gat ctt gcc ttc tgg cct gac cat cct gaa        480
Glu Pro Lys Glu Glu Gln Asp Leu Ala Phe Trp Pro Asp His Pro Glu
145                 150                 155                 160 tct ttc agg gat gtt ctg aac aag tat gca tca gga acc aaa aga att        528
Ser Phe Arg Asp Val Leu Asn Lys Tyr Ala Ser Gly Thr Lys Arg Ile
                165                 170                 175 aga gac gat atc att cag gct atg gcc aag ctt ctt gag ctt gat gag        576
Arg Asp Asp Ile Ile Gln Ala Met Ala Lys Leu Leu Glu Leu Asp Glu
            180                 185                 190 gat tac ttc ttg gac cga ctc aac gaa gct cct gca ttt gca aga ttc        624
Asp Tyr Phe Leu Asp Arg Leu Asn Glu Ala Pro Ala Phe Ala Arg Phe
        195                 200                 205 aac tac tac cct ccc tgt cca agg cct gac ctt gtg ttc ggc atc agg        672
Asn Tyr Tyr Pro Pro Cys Pro Arg Pro Asp Leu Val Phe Gly Ile Arg
    210                 215                 220 cct cac tcc gac ggc acc ctc ttg acg att ctt ctc gtc gac aaa gat        720
Pro His Ser Asp Gly Thr Leu Leu Thr Ile Leu Leu Val Asp Lys Asp
225                 230                 235                 240 gtc agt ggc ctg caa gtt cag agg gat ggc aag tgg tcc aac gtt gag        768
Val Ser Gly Leu Gln Val Gln Arg Asp Gly Lys Trp Ser Asn Val Glu
                245                 250                 255 gca act cct cac aca ttg ctg atc aac tta ggt gac acc atg gag gta        816
Ala Thr Pro His Thr Leu Leu Ile Asn Leu Gly Asp Thr Met Glu Val
            260                 265                 270 atg tgc aat ggc atc ttc agg agc ccg gtg cac agg gtg gtg aca aac        864
Met Cys Asn Gly Ile Phe Arg Ser Pro Val His Arg Val Val Thr Asn
        275                 280                 285 gcc gag aag gag agg atc tcc ctg gcc atg tta tac agc gtg aac gat        912
Ala Glu Lys Glu Arg Ile Ser Leu Ala Met Leu Tyr Ser Val Asn Asp
    290                 295                 300 gag aaa gac att gag ccg gcg gct ggt ttg ctg gat gag aat cgg cct        960
Glu Lys Asp Ile Glu Pro Ala Ala Gly Leu Leu Asp Glu Asn Arg Pro
305                 310                 315                 320 gca aga tac agg aaa gtg agc gtc gaa gag ttc agg gcc ggg atc ttt       1008
Ala Arg Tyr Arg Lys Val Ser Val Glu Glu Phe Arg Ala Gly Ile Phe
                325                 330                 335 gga aaa ttc tct cga gga gag agg tac atc gac tcc ctg agg atc tga       1056
Gly Lys Phe Ser Arg Gly Glu Arg Tyr Ile Asp Ser Leu Arg Ile
            340                 345                 350

<210> SEQ ID NO 2
<211> LENGTH: 351
<212> TYPE: PRT
<213> ORGANISM: Oryza sativa

<400> SEQUENCE: 2

Met Ala Asp Glu Ser Trp Arg Ala Pro Ala Ile Val Gln Glu Leu Ala
1               5                   10                  15
```

```
Ala Ala Gly Val Glu Pro Pro Ser Arg Tyr Leu Leu Arg Glu Lys
            20              25                  30

Asp Arg Ser Asp Val Lys Leu Val Ala Glu Leu Pro Glu Pro Leu
        35              40                  45

Pro Val Val Asp Leu Ser Arg Leu Asp Gly Ala Glu Glu Ala Thr Lys
50              55                  60

Leu Arg Val Ala Leu Gln Asn Trp Gly Phe Leu Leu Thr Asn His
65              70                  75                  80

Gly Val Glu Ala Ser Leu Met Asp Ser Val Met Asn Leu Ser Arg Glu
                85                  90                  95

Phe Phe Asn Gln Pro Ile Glu Arg Lys Gln Lys Phe Ser Asn Leu Ile
            100                 105                 110

Asp Gly Lys Asn Phe Gln Ile Gln Gly Tyr Gly Thr Asp Arg Val Val
            115                 120                 125

Thr Gln Asp Gln Ile Leu Asp Trp Ser Asp Arg Leu His Leu Arg Val
            130                 135                 140

Glu Pro Lys Glu Glu Gln Asp Leu Ala Phe Trp Pro Asp His Pro Glu
145                 150                 155                 160

Ser Phe Arg Asp Val Leu Asn Lys Tyr Ala Ser Gly Thr Lys Arg Ile
                165                 170                 175

Arg Asp Asp Ile Ile Gln Ala Met Ala Lys Leu Leu Glu Leu Asp Glu
            180                 185                 190

Asp Tyr Phe Leu Asp Arg Leu Asn Glu Ala Pro Ala Phe Ala Arg Phe
            195                 200                 205

Asn Tyr Tyr Pro Pro Cys Pro Arg Pro Asp Leu Val Phe Gly Ile Arg
            210                 215                 220

Pro His Ser Asp Gly Thr Leu Leu Thr Ile Leu Leu Val Asp Lys Asp
225                 230                 235                 240

Val Ser Gly Leu Gln Val Gln Arg Asp Gly Lys Trp Ser Asn Val Glu
                245                 250                 255

Ala Thr Pro His Thr Leu Leu Ile Asn Leu Gly Asp Thr Met Glu Val
            260                 265                 270

Met Cys Asn Gly Ile Phe Arg Ser Pro Val His Arg Val Val Thr Asn
            275                 280                 285

Ala Glu Lys Glu Arg Ile Ser Leu Ala Met Leu Tyr Ser Val Asn Asp
            290                 295                 300

Glu Lys Asp Ile Glu Pro Ala Ala Gly Leu Leu Asp Glu Asn Arg Pro
305                 310                 315                 320

Ala Arg Tyr Arg Lys Val Ser Val Glu Glu Phe Arg Ala Gly Ile Phe
            325                 330                 335

Gly Lys Phe Ser Arg Gly Glu Arg Tyr Ile Asp Ser Leu Arg Ile
            340                 345                 350

<210> SEQ ID NO 3
<211> LENGTH: 1056
<212> TYPE: DNA
<213> ORGANISM: Oryza sativa
<220> FEATURE:
<221> NAME/KEY: CDS
<222> LOCATION: (1)..(1056)

<400> SEQUENCE: 3 atg gct gac gag tca tgg agg acg ccg gcg ata gtg caa gag ctg gcg    48
Met Ala Asp Glu Ser Trp Arg Thr Pro Ala Ile Val Gln Glu Leu Ala
1               5                   10                  15 gcg gcc ggc gtc gag gag cca ccg agt cgg tac gtg ctt ggg gag aaa    96
```

|   |   |   |   |   |   |   |   |   |   |   |   |   |   |   |   |     |
|---|---|---|---|---|---|---|---|---|---|---|---|---|---|---|---|-----|
| Ala | Ala | Gly | Val | Glu | Pro | Pro | Ser | Arg | Tyr | Val | Leu | Gly | Glu | Lys |   |     |
|   |   |   | 20  |   |   |   | 25  |   |   |   | 30  |   |   |   |   |     |

```
gac cgt tct gac gag ctg gtc gcc gcc gag ctg ccg gag ccc atc ccc      144
Asp Arg Ser Asp Glu Leu Val Ala Ala Glu Leu Pro Glu Pro Ile Pro
        35                  40                  45 gtc gtt gat ctc agc cgg cta gcc ggc gcc gac gag gct gcc aag ctc      192
Val Val Asp Leu Ser Arg Leu Ala Gly Ala Asp Glu Ala Ala Lys Leu
 50                  55                  60 agg gcg gct ctg cag aat tgg ggc ttc ttc ctg ctt acc aac cat gga      240
Arg Ala Ala Leu Gln Asn Trp Gly Phe Phe Leu Leu Thr Asn His Gly
 65                  70                  75                  80 gta gaa acc tct ctg atg gat gat gtg ttg aac ttg gca aga gag ttc      288
Val Glu Thr Ser Leu Met Asp Asp Val Leu Asn Leu Ala Arg Glu Phe
                 85                  90                  95 ttc aac caa ccg atc gaa cgg aag cga aaa ttc agc aac ttg atc gac      336
Phe Asn Gln Pro Ile Glu Arg Lys Arg Lys Phe Ser Asn Leu Ile Asp
            100                 105                 110 ggc aag aac ttc cag gtg gaa ggg tat gga act gac cgg gtg gta acc      384
Gly Lys Asn Phe Gln Val Glu Gly Tyr Gly Thr Asp Arg Val Val Thr
        115                 120                 125 caa gat cag atc ctg gac tgg tct gat cgg ctg ttt ctc aga gtt gaa      432
Gln Asp Gln Ile Leu Asp Trp Ser Asp Arg Leu Phe Leu Arg Val Glu
130                 135                 140 ccc aag gag gag cga aat ctt gcc ttc tgg cct gac cat cct gaa tct      480
Pro Lys Glu Glu Arg Asn Leu Ala Phe Trp Pro Asp His Pro Glu Ser
145                 150                 155                 160 ttc agg gat gtt ctg aac gag tac gca tca aga acc aaa aga ata aga      528
Phe Arg Asp Val Leu Asn Glu Tyr Ala Ser Arg Thr Lys Arg Ile Arg
                165                 170                 175 gac gat atc gtt cag gct atg tcc aag ctt ctt ggg ctt gat gag gat      576
Asp Asp Ile Val Gln Ala Met Ser Lys Leu Leu Gly Leu Asp Glu Asp
            180                 185                 190 tac ttc ttc gac cga ctc aac aaa gct cct gca ctt gca aga ttc aac      624
Tyr Phe Phe Asp Arg Leu Asn Lys Ala Pro Ala Leu Ala Arg Phe Asn
        195                 200                 205 tac tac cct ccc tgt cca agg cct gac ctt gtg ttc ggc gtc agg cct      672
Tyr Tyr Pro Pro Cys Pro Arg Pro Asp Leu Val Phe Gly Val Arg Pro
210                 215                 220 cac tcc gac ggc tcc ctc ttt acg att ctt ctc gtc gac gaa gat gtc      720
His Ser Asp Gly Ser Leu Phe Thr Ile Leu Leu Val Asp Glu Asp Val
225                 230                 235                 240 ggt ggc ctg caa att cag agg gat ggc aag tgg tac aat gtt cag gtc      768
Gly Gly Leu Gln Ile Gln Arg Asp Gly Lys Trp Tyr Asn Val Gln Val
                245                 250                 255 act ccc aac aca ttg ctg atc aac tta ggt gac acc atg gag gta ttg      816
Thr Pro Asn Thr Leu Leu Ile Asn Leu Gly Asp Thr Met Glu Val Leu
            260                 265                 270 tgc aat ggc atc ttc agg agc cca gtg cac agg gtg gtg aca aac gcc      864
Cys Asn Gly Ile Phe Arg Ser Pro Val His Arg Val Val Thr Asn Ala
        275                 280                 285 gag agg gag agg atc tca ctg gcc atg ttt tac agt gtg aat gat gag      912
Glu Arg Glu Arg Ile Ser Leu Ala Met Phe Tyr Ser Val Asn Asp Glu
290                 295                 300 aaa gat att ggg ccg gcg gct ggt ttg ctg gat gag aat cgg cct gca      960
Lys Asp Ile Gly Pro Ala Ala Gly Leu Leu Asp Glu Asn Arg Pro Ala
305                 310                 315                 320 aga tac agg aaa gtg agc gtc gga gag ttc agg gct ggg atc att gga     1008
Arg Tyr Arg Lys Val Ser Val Gly Glu Phe Arg Ala Gly Ile Ile Gly
                325                 330                 335
```

```
aaa ttc tct cga cga gag aga tac atc gac tcc ctg aag atc tga ttt      1056
Lys Phe Ser Arg Arg Glu Arg Tyr Ile Asp Ser Leu Lys Ile     Phe
            340                 345                 350
```

<210> SEQ ID NO 4
<211> LENGTH: 350
<212> TYPE: PRT
<213> ORGANISM: Oryza sativa

<400> SEQUENCE: 4

```
Met Ala Asp Glu Ser Trp Arg Thr Pro Ala Ile Val Gln Glu Leu Ala
1               5                   10                  15

Ala Ala Gly Val Glu Glu Pro Pro Ser Arg Tyr Val Leu Gly Glu Lys
                20                  25                  30

Asp Arg Ser Asp Glu Leu Val Ala Ala Glu Leu Pro Glu Pro Ile Pro
            35                  40                  45

Val Val Asp Leu Ser Arg Leu Ala Gly Ala Asp Glu Ala Ala Lys Leu
        50                  55                  60

Arg Ala Ala Leu Gln Asn Trp Gly Phe Phe Leu Leu Thr Asn His Gly
65                  70                  75                  80

Val Glu Thr Ser Leu Met Asp Asp Val Leu Asn Leu Ala Arg Glu Phe
                85                  90                  95

Phe Asn Gln Pro Ile Glu Arg Lys Arg Lys Phe Ser Asn Leu Ile Asp
                100                 105                 110

Gly Lys Asn Phe Gln Val Glu Gly Tyr Gly Thr Asp Arg Val Val Thr
            115                 120                 125

Gln Asp Gln Ile Leu Asp Trp Ser Asp Arg Leu Phe Leu Arg Val Glu
130                 135                 140

Pro Lys Glu Glu Arg Asn Leu Ala Phe Trp Pro Asp His Pro Glu Ser
145                 150                 155                 160

Phe Arg Asp Val Leu Asn Glu Tyr Ala Ser Arg Thr Lys Arg Ile Arg
                165                 170                 175

Asp Asp Ile Val Gln Ala Met Ser Lys Leu Leu Gly Leu Asp Glu Asp
            180                 185                 190

Tyr Phe Phe Asp Arg Leu Asn Lys Ala Pro Ala Leu Ala Arg Phe Asn
        195                 200                 205

Tyr Tyr Pro Pro Cys Pro Arg Pro Asp Leu Val Phe Gly Val Arg Pro
210                 215                 220

His Ser Asp Gly Ser Leu Phe Thr Ile Leu Leu Val Asp Glu Asp Val
225                 230                 235                 240

Gly Gly Leu Gln Ile Gln Arg Asp Gly Lys Trp Tyr Asn Val Gln Val
                245                 250                 255

Thr Pro Asn Thr Leu Leu Ile Asn Leu Gly Asp Thr Met Glu Val Leu
            260                 265                 270

Cys Asn Gly Ile Phe Arg Ser Pro Val His Arg Val Thr Asn Ala
        275                 280                 285

Glu Arg Glu Arg Ile Ser Leu Ala Met Phe Tyr Ser Val Asn Asp Glu
    290                 295                 300

Lys Asp Ile Gly Pro Ala Ala Gly Leu Leu Asp Glu Asn Arg Pro Ala
305                 310                 315                 320

Arg Tyr Arg Lys Val Ser Val Gly Glu Phe Arg Ala Gly Ile Ile Gly
                325                 330                 335

Lys Phe Ser Arg Arg Glu Arg Tyr Ile Asp Ser Leu Lys Ile
            340                 345                 350
```

<210> SEQ ID NO 5
<211> LENGTH: 1065
<212> TYPE: DNA
<213> ORGANISM: Oryza sativa
<220> FEATURE:
<221> NAME/KEY: CDS
<222> LOCATION: (1)..(1065)

<400> SEQUENCE: 5

| | | | | | | | | | | | | | | | | |
|---|---|---|---|---|---|---|---|---|---|---|---|---|---|---|---|---|
| atg | gcc | gac | gaa | cca | tgg | cgg | ttg | ccg | aac | att | gtc | cag | gaa | cta | gca | 48 |
| Met | Ala | Asp | Glu | Pro | Trp | Arg | Leu | Pro | Asn | Ile | Val | Gln | Glu | Leu | Ala | |
| 1 | | | | 5 | | | | | 10 | | | | | 15 | | |
| gct | gga | gtg | caa | gag | cca | ccg | agt | cgc | tac | cta | caa | gac | ctg | gca | ggc | 96 |
| Ala | Gly | Val | Gln | Glu | Pro | Pro | Ser | Arg | Tyr | Leu | Gln | Asp | Leu | Ala | Gly | |
| | | | 20 | | | | | 25 | | | | | 30 | | | |
| ggg | gat | cag | ctg | gca | gga | gcg | gag | ata | cca | gag | cct | ata | ccc | act | ata | 144 |
| Gly | Asp | Gln | Leu | Ala | Gly | Ala | Glu | Ile | Pro | Glu | Pro | Ile | Pro | Thr | Ile | |
| | 35 | | | | | 40 | | | | | 45 | | | | | |
| gac | cta | ggt | cgc | ctt | tct | ggg | tca | gac | ggt | gct | gac | gaa | gct | gcc | aaa | 192 |
| Asp | Leu | Gly | Arg | Leu | Ser | Gly | Ser | Asp | Gly | Ala | Asp | Glu | Ala | Ala | Lys | |
| 50 | | | | | 55 | | | | | 60 | | | | | | |
| ctc | cgc | agt | gcc | ctc | cag | aat | tgg | ggc | ctc | ttt | ctg | gtg | tct | aac | cat | 240 |
| Leu | Arg | Ser | Ala | Leu | Gln | Asn | Trp | Gly | Leu | Phe | Leu | Val | Ser | Asn | His | |
| 65 | | | | | 70 | | | | | 75 | | | | | 80 | |
| ggc | gtg | gaa | acg | tcg | ctt | att | gat | gcg | gtc | atc | gaa | gca | gcc | agg | gag | 288 |
| Gly | Val | Glu | Thr | Ser | Leu | Ile | Asp | Ala | Val | Ile | Glu | Ala | Ala | Arg | Glu | |
| | | | | 85 | | | | | 90 | | | | | 95 | | |
| ttc | ttc | cgg | caa | cct | gtg | gag | gag | aag | aag | aag | ttg | agc | aac | ctc | atc | 336 |
| Phe | Phe | Arg | Gln | Pro | Val | Glu | Glu | Lys | Lys | Lys | Leu | Ser | Asn | Leu | Ile | |
| | | | 100 | | | | | 105 | | | | | 110 | | | |
| gac | gga | aag | cgt | ttc | cag | att | gag | ggc | tat | ggc | aat | gat | ccc | gtc | caa | 384 |
| Asp | Gly | Lys | Arg | Phe | Gln | Ile | Glu | Gly | Tyr | Gly | Asn | Asp | Pro | Val | Gln | |
| | 115 | | | | | 120 | | | | | 125 | | | | | |
| acc | aaa | gac | cag | att | ctc | gac | tgg | agc | gac | agg | ctc | cac | ctc | aaa | gtc | 432 |
| Thr | Lys | Asp | Gln | Ile | Leu | Asp | Trp | Ser | Asp | Arg | Leu | His | Leu | Lys | Val | |
| 130 | | | | | 135 | | | | | 140 | | | | | | |
| gag | cca | gag | tgc | gat | agg | aat | ttg | gcc | ttt | tgg | ccg | aca | cac | ccg | aag | 480 |
| Glu | Pro | Glu | Cys | Asp | Arg | Asn | Leu | Ala | Phe | Trp | Pro | Thr | His | Pro | Lys | |
| 145 | | | | | 150 | | | | | 155 | | | | | 160 | |
| agc | ttt | agg | gac | att | ctg | cac | gag | tac | acc | ctc | aag | atc | aag | aca | gtg | 528 |
| Ser | Phe | Arg | Asp | Ile | Leu | His | Glu | Tyr | Thr | Leu | Lys | Ile | Lys | Thr | Val | |
| | | | | 165 | | | | | 170 | | | | | 175 | | |
| aag | aac | gac | atc | ctc | ttg | gcg | ttg | gcc | aag | ctt | ctc | gaa | ttg | gac | gag | 576 |
| Lys | Asn | Asp | Ile | Leu | Leu | Ala | Leu | Ala | Lys | Leu | Leu | Glu | Leu | Asp | Glu | |
| | | | 180 | | | | | 185 | | | | | 190 | | | |
| gac | tgc | ctc | ctg | aac | cag | ttc | tcg | gat | agg | gcg | att | acc | aca | gcg | cgc | 624 |
| Asp | Cys | Leu | Leu | Asn | Gln | Phe | Ser | Asp | Arg | Ala | Ile | Thr | Thr | Ala | Arg | |
| | 195 | | | | | 200 | | | | | 205 | | | | | |
| ttc | aac | tac | tac | tca | ccc | tgt | ccc | aga | cct | gat | ctt | gtc | ctg | gga | ctg | 672 |
| Phe | Asn | Tyr | Tyr | Ser | Pro | Cys | Pro | Arg | Pro | Asp | Leu | Val | Leu | Gly | Leu | |
| 210 | | | | | 215 | | | | | 220 | | | | | | |
| aag | ccg | cat | agc | gat | ctt | tgc | gct | ttg | acc | gtc | ctt | ctg | acc | gac | aaa | 720 |
| Lys | Pro | His | Ser | Asp | Leu | Cys | Ala | Leu | Thr | Val | Leu | Leu | Thr | Asp | Lys | |
| 225 | | | | | 230 | | | | | 235 | | | | | 240 | |
| gag | gtt | ggc | gga | cta | caa | gtt | ctc | cgg | gat | ggc | act | tgg | tac | tcc | gtt | 768 |
| Glu | Val | Gly | Gly | Leu | Gln | Val | Leu | Arg | Asp | Gly | Thr | Trp | Tyr | Ser | Val | |
| | | | | 245 | | | | | 250 | | | | | 255 | | |
| cca | gct | gta | agg | gac | tac | tcc | ctg | ctg | atc | aac | atc | ggc | gtt | acg | ctc | 816 |
| Pro | Ala | Val | Arg | Asp | Tyr | Ser | Leu | Leu | Ile | Asn | Ile | Gly | Val | Thr | Leu | |
| | | | 260 | | | | | 265 | | | | | 270 | | | |
| gag | atc | atg | acg | aac | ggg | act | ttt | cgt | gcc | cca | ctt | cat | cgc | gtg | gtg | 864 |

```
Glu Ile Met Thr Asn Gly Thr Phe Arg Ala Pro Leu His Arg Val Val
            275                 280                 285 acc aat gcg gaa cgt gag agg atg tcg gta gcc atg ttc tat gcg gtc        912
Thr Asn Ala Glu Arg Glu Arg Met Ser Val Ala Met Phe Tyr Ala Val
            290                 295                 300 gat ggg gag aag gag atc gag cca gtg gcc gag ctc ctg ggc ctg aag        960
Asp Gly Glu Lys Glu Ile Glu Pro Val Ala Glu Leu Leu Gly Leu Lys
305                 310                 315                 320 caa caa tcc gcc aga tat cgc ggg atc aag ggt aag gat ctc ctc atc       1008
Gln Gln Ser Ala Arg Tyr Arg Gly Ile Lys Gly Lys Asp Leu Leu Ile
                325                 330                 335 ggc cac tac gag cac ttc tcc aga ggt ggg cgg gtt gtg gac tca ctc       1056
Gly His Tyr Glu His Phe Ser Arg Gly Gly Arg Val Val Asp Ser Leu
            340                 345                 350 aag atc tga                                                           1065
Lys Ile <210> SEQ ID NO 6
<211> LENGTH: 354
<212> TYPE: PRT
<213> ORGANISM: Oryza sativa

<400> SEQUENCE: 6

Met Ala Asp Glu Pro Trp Arg Leu Pro Asn Ile Val Gln Glu Leu Ala
1               5                   10                  15

Ala Gly Val Gln Glu Pro Pro Ser Arg Tyr Leu Gln Asp Leu Ala Gly
            20                  25                  30

Gly Asp Gln Leu Ala Gly Ala Glu Ile Pro Glu Pro Ile Pro Thr Ile
        35                  40                  45

Asp Leu Gly Arg Leu Ser Gly Ser Asp Gly Ala Asp Glu Ala Ala Lys
    50                  55                  60

Leu Arg Ser Ala Leu Gln Asn Trp Gly Leu Phe Leu Val Ser Asn His
65                  70                  75                  80

Gly Val Glu Thr Ser Leu Ile Asp Ala Val Ile Glu Ala Ala Arg Glu
                85                  90                  95

Phe Phe Arg Gln Pro Val Glu Glu Lys Lys Lys Leu Ser Asn Leu Ile
            100                 105                 110

Asp Gly Lys Arg Phe Gln Ile Glu Gly Tyr Gly Asn Asp Pro Val Gln
        115                 120                 125

Thr Lys Asp Gln Ile Leu Asp Trp Ser Asp Arg Leu His Leu Lys Val
    130                 135                 140

Glu Pro Glu Cys Asp Arg Asn Leu Ala Phe Trp Pro Thr His Pro Lys
145                 150                 155                 160

Ser Phe Arg Asp Ile Leu His Glu Tyr Thr Leu Lys Ile Lys Thr Val
                165                 170                 175

Lys Asn Asp Ile Leu Leu Ala Leu Ala Lys Leu Leu Glu Leu Asp Glu
            180                 185                 190

Asp Cys Leu Leu Asn Gln Phe Ser Asp Arg Ala Ile Thr Thr Ala Arg
        195                 200                 205

Phe Asn Tyr Tyr Ser Pro Cys Pro Arg Pro Asp Leu Val Leu Gly Leu
    210                 215                 220

Lys Pro His Ser Asp Leu Cys Ala Leu Thr Val Leu Leu Thr Asp Lys
225                 230                 235                 240

Glu Val Gly Gly Leu Gln Val Leu Arg Asp Gly Thr Trp Tyr Ser Val
                245                 250                 255

Pro Ala Val Arg Asp Tyr Ser Leu Leu Ile Asn Ile Gly Val Thr Leu
```

```
                  260                 265                 270
Glu Ile Met Thr Asn Gly Thr Phe Arg Ala Pro Leu His Arg Val Val
            275                 280                 285

Thr Asn Ala Glu Arg Glu Arg Met Ser Val Ala Met Phe Tyr Ala Val
        290                 295                 300

Asp Gly Glu Lys Glu Ile Glu Pro Val Ala Glu Leu Leu Gly Leu Lys
305                 310                 315                 320

Gln Gln Ser Ala Arg Tyr Arg Gly Ile Lys Gly Lys Asp Leu Leu Ile
                325                 330                 335

Gly His Tyr Glu His Phe Ser Arg Gly Gly Arg Val Val Asp Ser Leu
            340                 345                 350

Lys Ile

<210> SEQ ID NO 7
<211> LENGTH: 1059
<212> TYPE: DNA
<213> ORGANISM: Hordeum vulgare
<220> FEATURE:
<221> NAME/KEY: CDS
<222> LOCATION: (1)..(1059)

<400> SEQUENCE: 7
```

| | | |
|---|---|---|
| atg gcg gcg tcc gat gaa atg ccg atg gtt caa gac cta gtt tcg gct<br>Met Ala Ala Ser Asp Glu Met Pro Met Val Gln Asp Leu Val Ser Ala<br>1                   5                     10                  15 | | 48 |
| ggc gtt caa gag cct ccc agt cgg tac ctc gtg cac gag caa gat cgc<br>Gly Val Gln Glu Pro Pro Ser Arg Tyr Leu Val His Glu Gln Asp Arg<br>                    20                     25                   30 | | 96 |
| cat ggc gac ctc ctt gcc gca cat gag atg ccc gag cca att ccg ctg<br>His Gly Asp Leu Leu Ala Ala His Glu Met Pro Glu Pro Ile Pro Leu<br>            35                     40                   45 | | 144 |
| att gac cta tct cgc ctt atg gac gcc gat gag gca gac aag ctc aga<br>Ile Asp Leu Ser Arg Leu Met Asp Ala Asp Glu Ala Asp Lys Leu Arg<br> 50                     55                     60 | | 192 |
| gct gcg ttg caa act tgg ggc ttc ttt ctc gcg aca aac cac ggc ata<br>Ala Ala Leu Gln Thr Trp Gly Phe Phe Leu Ala Thr Asn His Gly Ile<br>65                    70                     75                   80 | | 240 |
| gag gac tcc ttg atg gag gcc atg atg tct gcg tcg aga gag ttc ttc<br>Glu Asp Ser Leu Met Glu Ala Met Met Ser Ala Ser Arg Glu Phe Phe<br>                    85                     90                   95 | | 288 |
| cgt cag cca agc gaa gag aag cag aaa tgc tcc aat ctg gtg gat ggg<br>Arg Gln Pro Ser Glu Glu Lys Gln Lys Cys Ser Asn Leu Val Asp Gly<br>                    100                   105                  110 | | 336 |
| aat ggc aag cac tat cag gtc gaa ggt tac gga tca gac aag gtc gag<br>Asn Gly Lys His Tyr Gln Val Glu Gly Tyr Gly Ser Asp Lys Val Glu<br>            115                   120                  125 | | 384 |
| tca gag gac caa gtc ctc aac tgg aac gat agg ctg cac ttg agg gta<br>Ser Glu Asp Gln Val Leu Asn Trp Asn Asp Arg Leu His Leu Arg Val<br>130                   135                     140 | | 432 |
| gaa ccg gag gac gaa cgc aat ttc gcc aaa tgg cct tct cac cca gag<br>Glu Pro Glu Asp Glu Arg Asn Phe Ala Lys Trp Pro Ser His Pro Glu<br>145                   150                     155                  160 | | 480 |
| tca ttc cgt gac gtg ctc aac gag tac gcg agc aag acg aag aag atc<br>Ser Phe Arg Asp Val Leu Asn Glu Tyr Ala Ser Lys Thr Lys Lys Ile<br>                    165                   170                  175 | | 528 |
| agg gac ttg gtg cta cgc agc atc gcc aaa ctc ctg gag att gat gag<br>Arg Asp Leu Val Leu Arg Ser Ile Ala Lys Leu Leu Glu Ile Asp Glu<br>                    180                   185                  190 | | 576 |
| gac tac ttc gtg aat cag atc tcc aac aaa gca tcc ggt ttt gcc agg | | 624 |

```
Asp Tyr Phe Val Asn Gln Ile Ser Asn Lys Ala Ser Gly Phe Ala Arg
        195                 200                 205 ctc tac tac tat ccg ccc tgt cct agg ccc gac ctt gta ctc gga ctc    672
Leu Tyr Tyr Tyr Pro Pro Cys Pro Arg Pro Asp Leu Val Leu Gly Leu
    210                 215                 220 act ccg cat tcg gac ggg aat ttg ctc acc atc ctg ttc gtt gac gat    720
Thr Pro His Ser Asp Gly Asn Leu Leu Thr Ile Leu Phe Val Asp Asp
225                 230                 235                 240 gac gtc ggt ggc ctt cag gtc caa cgg gat ggg aag tgg tac aac gtg    768
Asp Val Gly Gly Leu Gln Val Gln Arg Asp Gly Lys Trp Tyr Asn Val
                245                 250                 255 cca gca aag cca cat acg ctg gtg atc aac ctt gcc gat tgc ctg gag    816
Pro Ala Lys Pro His Thr Leu Val Ile Asn Leu Ala Asp Cys Leu Glu
            260                 265                 270 atc atg aac aac ggg ata ttc cgg agt ccc gtt cac agg gtc gtc aca    864
Ile Met Asn Asn Gly Ile Phe Arg Ser Pro Val His Arg Val Val Thr
        275                 280                 285 aac acc gag aag gag cgg ctg agc ctc gct gtg ttc tat gcc gtt gat    912
Asn Thr Glu Lys Glu Arg Leu Ser Leu Ala Val Phe Tyr Ala Val Asp
    290                 295                 300 gaa gaa acc gtg ttg gaa cca gct cct gga ctc ctt gac gag aag agg    960
Glu Glu Thr Val Leu Glu Pro Ala Pro Gly Leu Leu Asp Glu Lys Arg
305                 310                 315                 320 cca cca aga tac cgc aag atg atg gcc aag gac ttt gtc gtg gga ctg   1008
Pro Pro Arg Tyr Arg Lys Met Met Ala Lys Asp Phe Val Val Gly Leu
                325                 330                 335 ttc gag cac ttt ctg cag ggc aag cgc ttt atc gat acc ctc aag atg   1056
Phe Glu His Phe Leu Gln Gly Lys Arg Phe Ile Asp Thr Leu Lys Met
            340                 345                 350 tga                                                                1059

<210> SEQ ID NO 8
<211> LENGTH: 352
<212> TYPE: PRT
<213> ORGANISM: Hordeum vulgare

<400> SEQUENCE: 8

Met Ala Ala Ser Asp Glu Met Pro Met Val Gln Asp Leu Val Ser Ala
1               5                   10                  15

Gly Val Gln Glu Pro Pro Ser Arg Tyr Leu Val His Glu Gln Asp Arg
            20                  25                  30

His Gly Asp Leu Leu Ala Ala His Glu Met Pro Glu Pro Ile Pro Leu
        35                  40                  45

Ile Asp Leu Ser Arg Leu Met Asp Ala Asp Glu Ala Asp Lys Leu Arg
    50                  55                  60

Ala Ala Leu Gln Thr Trp Gly Phe Phe Leu Ala Thr Asn His Gly Ile
65                  70                  75                  80

Glu Asp Ser Leu Met Glu Ala Met Met Ser Ala Ser Arg Glu Phe Phe
                85                  90                  95

Arg Gln Pro Ser Glu Glu Lys Gln Lys Cys Ser Asn Leu Val Asp Gly
            100                 105                 110

Asn Gly Lys His Tyr Gln Val Glu Gly Tyr Gly Ser Asp Lys Val Glu
        115                 120                 125

Ser Glu Asp Gln Val Leu Asn Trp Asn Asp Arg Leu His Leu Arg Val
    130                 135                 140

Glu Pro Glu Asp Glu Arg Asn Phe Ala Lys Trp Pro Ser His Pro Glu
145                 150                 155                 160
```

```
Ser Phe Arg Asp Val Leu Asn Glu Tyr Ala Ser Lys Thr Lys Lys Ile
            165                 170                 175

Arg Asp Leu Val Leu Arg Ser Ile Ala Lys Leu Leu Glu Ile Asp Glu
        180                 185                 190

Asp Tyr Phe Val Asn Gln Ile Ser Asn Lys Ala Ser Gly Phe Ala Arg
    195                 200                 205

Leu Tyr Tyr Tyr Pro Pro Cys Pro Arg Pro Asp Leu Val Leu Gly Leu
210                 215                 220

Thr Pro His Ser Asp Gly Asn Leu Leu Thr Ile Leu Phe Val Asp Asp
225                 230                 235                 240

Asp Val Gly Gly Leu Gln Val Gln Arg Asp Gly Lys Trp Tyr Asn Val
                245                 250                 255

Pro Ala Lys Pro His Thr Leu Val Ile Asn Leu Ala Asp Cys Leu Glu
            260                 265                 270

Ile Met Asn Asn Gly Ile Phe Arg Ser Pro Val His Arg Val Val Thr
        275                 280                 285

Asn Thr Glu Lys Glu Arg Leu Ser Leu Ala Val Phe Tyr Ala Val Asp
    290                 295                 300

Glu Glu Thr Val Leu Glu Pro Ala Pro Gly Leu Leu Asp Glu Lys Arg
305                 310                 315                 320

Pro Pro Arg Tyr Arg Lys Met Met Ala Lys Asp Phe Val Val Gly Leu
                325                 330                 335

Phe Glu His Phe Leu Gln Gly Lys Arg Phe Ile Asp Thr Leu Lys Met
            340                 345                 350

<210> SEQ ID NO 9
<211> LENGTH: 1068
<212> TYPE: DNA
<213> ORGANISM: Hordeum vulgare
<220> FEATURE:
<221> NAME/KEY: CDS
<222> LOCATION: (1)..(1068)

<400> SEQUENCE: 9 atg gcg gat gca gaa ccc tgg aaa aca gtg aag ata ccg ccg ata gtg      48
Met Ala Asp Ala Glu Pro Trp Lys Thr Val Lys Ile Pro Pro Ile Val
1               5                   10                  15 cag gaa ctg gca aca ggt gtg caa gag cca cca tcc cgg tat gta atc      96
Gln Glu Leu Ala Thr Gly Val Gln Glu Pro Pro Ser Arg Tyr Val Ile
            20                  25                  30 gcc gag cat aac cgc cca gct gtg gct gcc tcc gaa atg ccg gac cct     144
Ala Glu His Asn Arg Pro Ala Val Ala Ala Ser Glu Met Pro Asp Pro
        35                  40                  45 att ccc atc gtt gac ctt tct cgc ttg tcc gac aac tgt gcc gat gaa     192
Ile Pro Ile Val Asp Leu Ser Arg Leu Ser Asp Asn Cys Ala Asp Glu
    50                  55                  60 gtt gcc aag ttg cgc tca gcg ctc gaa aac tgg ggc ttg ttc ctc gca     240
Val Ala Lys Leu Arg Ser Ala Leu Glu Asn Trp Gly Leu Phe Leu Ala
65                  70                  75                  80 gtc ggg cac gga atg gag caa agc ttt ctc ggt gag gtc atg aag gtt     288
Val Gly His Gly Met Glu Gln Ser Phe Leu Gly Glu Val Met Lys Val
                85                  90                  95 gcg agg gag ttc ttt aag cta cct ttg gag gag aag cag aag tac tcg     336
Ala Arg Glu Phe Phe Lys Leu Pro Leu Glu Glu Lys Gln Lys Tyr Ser
            100                 105                 110 aac ctt gtg aac ggc gac gag gtt cgc att gaa ggc tat ggg aat gac     384
Asn Leu Val Asn Gly Asp Glu Val Arg Ile Glu Gly Tyr Gly Asn Asp
        115                 120                 125
```

-continued

```
atg gtc gtg agc gag aag caa atc ctc gat tgg tgc gat aga ctg tac      432
Met Val Val Ser Glu Lys Gln Ile Leu Asp Trp Cys Asp Arg Leu Tyr
    130                 135                 140 atc atc gtt gag cca gag aac aga cgg atc tac agt ctc tgg ccg act      480
Ile Ile Val Glu Pro Glu Asn Arg Arg Ile Tyr Ser Leu Trp Pro Thr
145                 150                 155                 160 caa cca cct tcc ttc cgt gac atc ctc agc gag tac acc gtg aga tgc      528
Gln Pro Pro Ser Phe Arg Asp Ile Leu Ser Glu Tyr Thr Val Arg Cys
                165                 170                 175 cat aag atc gcc aac ctg ttc ctc cag aat ctg gcg aag cta ctc gac      576
His Lys Ile Ala Asn Leu Phe Leu Gln Asn Leu Ala Lys Leu Leu Asp
            180                 185                 190 ctc cat gag gac tac ttc gtc aac atg ttc gac gag aac gct ctt gcg      624
Leu His Glu Asp Tyr Phe Val Asn Met Phe Asp Glu Asn Ala Leu Ala
        195                 200                 205 tat gcc agg ctc aac tac tac ccg aat tgc ccg aaa ccc gat cac gtg      672
Tyr Ala Arg Leu Asn Tyr Tyr Pro Asn Cys Pro Lys Pro Asp His Val
    210                 215                 220 ttt ggc atg aaa cct cac acg gac gcg tcg gtc att acc atc gtg ttc      720
Phe Gly Met Lys Pro His Thr Asp Ala Ser Val Ile Thr Ile Val Phe
225                 230                 235                 240 att gac gac aat gtc agt ggc cta caa ctc cag aac gat gga gtc tgg      768
Ile Asp Asp Asn Val Ser Gly Leu Gln Leu Gln Asn Asp Gly Val Trp
                245                 250                 255 tac aat gtg ccc att gta ccc aat gcc ctt ctc gtc aac gtt ggg gat      816
Tyr Asn Val Pro Ile Val Pro Asn Ala Leu Leu Val Asn Val Gly Asp
            260                 265                 270 gta atg gag atc atg tca aac ggc ttc ttc aag tct cca atc cac agg      864
Val Met Glu Ile Met Ser Asn Gly Phe Phe Lys Ser Pro Ile His Arg
        275                 280                 285 gtt gtg acg aat gca gag aaa gag agg ctg agc ttg gtg atg ttc tac      912
Val Val Thr Asn Ala Glu Lys Glu Arg Leu Ser Leu Val Met Phe Tyr
    290                 295                 300 acc atg aac ccc gaa aag gag ata gag cca ctg cca gag ctt gtc gat      960
Thr Met Asn Pro Glu Lys Glu Ile Glu Pro Leu Pro Glu Leu Val Asp
305                 310                 315                 320 gaa aag agg cca cgg agg tat cgc aag acg act acc aac gac tac atc     1008
Glu Lys Arg Pro Arg Arg Tyr Arg Lys Thr Thr Thr Asn Asp Tyr Ile
                325                 330                 335 gct aag ctg ttt gag aca ttt gcc cgt gga act ctg gcc att gac acc     1056
Ala Lys Leu Phe Glu Thr Phe Ala Arg Gly Thr Leu Ala Ile Asp Thr
            340                 345                 350 gtc aag atc tga                                                     1068
Val Lys Ile
355
```

<210> SEQ ID NO 10
<211> LENGTH: 355
<212> TYPE: PRT
<213> ORGANISM: Hordeum vulgare

<400> SEQUENCE: 10

```
Met Ala Asp Ala Glu Pro Trp Lys Thr Val Lys Ile Pro Pro Ile Val
1               5                   10                  15

Gln Glu Leu Ala Thr Gly Val Gln Glu Pro Pro Ser Arg Tyr Val Ile
            20                  25                  30

Ala Glu His Asn Arg Pro Ala Val Ala Ala Ser Glu Met Pro Asp Pro
        35                  40                  45

Ile Pro Ile Val Asp Leu Ser Arg Leu Ser Asp Asn Cys Ala Asp Glu
    50                  55                  60
```

```
Val Ala Lys Leu Arg Ser Ala Leu Glu Asn Trp Gly Leu Phe Leu Ala
 65                  70                  75                  80

Val Gly His Gly Met Glu Gln Ser Phe Leu Gly Glu Val Met Lys Val
                 85                  90                  95

Ala Arg Glu Phe Phe Lys Leu Pro Leu Glu Glu Lys Gln Lys Tyr Ser
            100                 105                 110

Asn Leu Val Asn Gly Asp Glu Val Arg Ile Glu Gly Tyr Gly Asn Asp
        115                 120                 125

Met Val Val Ser Glu Lys Gln Ile Leu Asp Trp Cys Asp Arg Leu Tyr
130                 135                 140

Ile Ile Val Glu Pro Glu Asn Arg Arg Ile Tyr Ser Leu Trp Pro Thr
145                 150                 155                 160

Gln Pro Pro Ser Phe Arg Asp Ile Leu Ser Glu Tyr Thr Val Arg Cys
                165                 170                 175

His Lys Ile Ala Asn Leu Phe Leu Gln Asn Leu Ala Lys Leu Leu Asp
            180                 185                 190

Leu His Glu Asp Tyr Phe Val Asn Met Phe Asp Glu Asn Ala Leu Ala
        195                 200                 205

Tyr Ala Arg Leu Asn Tyr Tyr Pro Asn Cys Pro Lys Pro Asp His Val
210                 215                 220

Phe Gly Met Lys Pro His Thr Asp Ala Ser Val Ile Thr Ile Val Phe
225                 230                 235                 240

Ile Asp Asp Asn Val Ser Gly Leu Gln Leu Gln Asn Asp Gly Val Trp
                245                 250                 255

Tyr Asn Val Pro Ile Val Pro Asn Ala Leu Leu Val Asn Val Gly Asp
            260                 265                 270

Val Met Glu Ile Met Ser Asn Gly Phe Phe Lys Ser Pro Ile His Arg
        275                 280                 285

Val Val Thr Asn Ala Glu Lys Glu Arg Leu Ser Leu Val Met Phe Tyr
290                 295                 300

Thr Met Asn Pro Glu Lys Glu Ile Glu Pro Leu Pro Glu Leu Val Asp
305                 310                 315                 320

Glu Lys Arg Pro Arg Arg Tyr Arg Lys Thr Thr Thr Asn Asp Tyr Ile
                325                 330                 335

Ala Lys Leu Phe Glu Thr Phe Ala Arg Gly Thr Leu Ala Ile Asp Thr
            340                 345                 350

Val Lys Ile
        355

<210> SEQ ID NO 11
<211> LENGTH: 1071
<212> TYPE: DNA
<213> ORGANISM: Hordeum vulgare
<220> FEATURE:
<221> NAME/KEY: CDS
<222> LOCATION: (1)..(1071)

<400> SEQUENCE: 11 atg gct agc tat gat cag cag ttc aag att ctc gag gtc cct cca att      48
Met Ala Ser Tyr Asp Gln Gln Phe Lys Ile Leu Glu Val Pro Pro Ile
 1               5                  10                  15 gtc caa gag ctc gtt ggt gcg ggt gtg aag gag cca cca tct caa tac      96
Val Gln Glu Leu Val Gly Ala Gly Val Lys Glu Pro Pro Ser Gln Tyr
                20                  25                  30 gtc ttg ccg gag caa tat cgc cct gca gct gcc gca gtg tcg gag atg     144
Val Leu Pro Glu Gln Tyr Arg Pro Ala Ala Ala Ala Val Ser Glu Met
```

```
                  35                  40                  45
cca gaa ccc ata ccg atc atc gac cta tcg agg ctg tca gcc gga tct     192
Pro Glu Pro Ile Pro Ile Ile Asp Leu Ser Arg Leu Ser Ala Gly Ser
         50                  55                  60 gct gaa gag ttc gac aaa ctc cgt agt gcc cta gag aac tgg aat ctc     240
Ala Glu Glu Phe Asp Lys Leu Arg Ser Ala Leu Glu Asn Trp Asn Leu
 65                  70                  75                  80 ttt ctg gcc gtt ggc cat ggc atg gaa ccc tcc ttc ttg gcg gaa gcc     288
Phe Leu Ala Val Gly His Gly Met Glu Pro Ser Phe Leu Ala Glu Ala
                 85                  90                  95 atg aag gca acg cgc gag ttc ttt aac ctc tca atc gag gag aag cag     336
Met Lys Ala Thr Arg Glu Phe Phe Asn Leu Ser Ile Glu Glu Lys Gln
            100                 105                 110 aag tac tcc aac ata gtc gga ggc gag aaa atg ggg atg gat ggc tat     384
Lys Tyr Ser Asn Ile Val Gly Gly Glu Lys Met Gly Met Asp Gly Tyr
        115                 120                 125 ggc aac gat atg gtg gtc aag gaa aac cag gtg ctg gat tgg aac gac     432
Gly Asn Asp Met Val Val Lys Glu Asn Gln Val Leu Asp Trp Asn Asp
130                 135                 140 aga ctc aac ctc ctc gtt gag cca gag tca ttg cgt acc tac agg ctc     480
Arg Leu Asn Leu Leu Val Glu Pro Glu Ser Leu Arg Thr Tyr Arg Leu
145                 150                 155                 160 tgg cct act caa ccg ccg tcg ttt agg gac gtt ctc tgc gaa tac acc     528
Trp Pro Thr Gln Pro Pro Ser Phe Arg Asp Val Leu Cys Glu Tyr Thr
                165                 170                 175 gtg cgg tgt aag gcg gcg acc aac atc gtg ata cgc aac atg gcc aag     576
Val Arg Cys Lys Ala Ala Thr Asn Ile Val Ile Arg Asn Met Ala Lys
            180                 185                 190 atg ctg aat ctt cag gag gag cac ctt gtg aac atg atc gga gac aac     624
Met Leu Asn Leu Gln Glu Glu His Leu Val Asn Met Ile Gly Asp Asn
        195                 200                 205 tcc atc aca cag gcc atc ttc aac tac tat ccc caa tgc cca aga ccc     672
Ser Ile Thr Gln Ala Ile Phe Asn Tyr Tyr Pro Gln Cys Pro Arg Pro
    210                 215                 220 gac cat gtc ctc ggt ctg aaa gcc cac aca gat gga tcc atc atc acc     720
Asp His Val Leu Gly Leu Lys Ala His Thr Asp Gly Ser Ile Ile Thr
225                 230                 235                 240 gta aac ttc gcc gat gcc gaa ggg ctt caa cta gag cgg aat ggc gtg     768
Val Asn Phe Ala Asp Ala Glu Gly Leu Gln Leu Glu Arg Asn Gly Val
                245                 250                 255 tgg tac aat gtc ccg att gtc ccc aat gcg ctt gtc atg aac att ggg     816
Trp Tyr Asn Val Pro Ile Val Pro Asn Ala Leu Val Met Asn Ile Gly
            260                 265                 270 gac atc atg gag atc ctg agc aat ggc ttc ttt aag agc ctg gta cac     864
Asp Ile Met Glu Ile Leu Ser Asn Gly Phe Phe Lys Ser Leu Val His
        275                 280                 285 agg gtt gtt acg aac gct gag aag gaa cgg ctc agt ctt gtc ctg gtg     912
Arg Val Val Thr Asn Ala Glu Lys Glu Arg Leu Ser Leu Val Leu Val
    290                 295                 300 tac aca ctc gaa ctc gag act caa ctg gag cct gtg agc gag ttg gtt     960
Tyr Thr Leu Glu Leu Glu Thr Gln Leu Glu Pro Val Ser Glu Leu Val
305                 310                 315                 320 gac gac aaa cgc cca gct agg tac atg aag att aag ctg aat gac tac    1008
Asp Asp Lys Arg Pro Ala Arg Tyr Met Lys Ile Lys Leu Asn Asp Tyr
                325                 330                 335 atg gag aag tac cac gat acg tac gca acc ggc act ttg gcg att gac    1056
Met Glu Lys Tyr His Asp Thr Tyr Ala Thr Gly Thr Leu Ala Ile Asp
            340                 345                 350 ggg gtg aag atc tga                                                 1071
```

```
Gly Val Lys Ile
        355

<210> SEQ ID NO 12
<211> LENGTH: 356
<212> TYPE: PRT
<213> ORGANISM: Hordeum vulgare

<400> SEQUENCE: 12

Met Ala Ser Tyr Asp Gln Gln Phe Lys Ile Leu Glu Val Pro Pro Ile
1               5                   10                  15

Val Gln Glu Leu Val Gly Ala Gly Val Lys Glu Pro Pro Ser Gln Tyr
            20                  25                  30

Val Leu Pro Glu Gln Tyr Arg Pro Ala Ala Ala Val Ser Glu Met
        35                  40                  45

Pro Glu Pro Ile Pro Ile Ile Asp Leu Ser Arg Leu Ser Ala Gly Ser
    50                  55                  60

Ala Glu Glu Phe Asp Lys Leu Arg Ser Ala Leu Glu Asn Trp Asn Leu
65                  70                  75                  80

Phe Leu Ala Val Gly His Gly Met Glu Pro Ser Phe Leu Ala Glu Ala
                85                  90                  95

Met Lys Ala Thr Arg Glu Phe Phe Asn Leu Ser Ile Glu Glu Lys Gln
            100                 105                 110

Lys Tyr Ser Asn Ile Val Gly Gly Glu Lys Met Gly Met Asp Gly Tyr
        115                 120                 125

Gly Asn Asp Met Val Val Lys Glu Asn Gln Val Leu Asp Trp Asn Asp
    130                 135                 140

Arg Leu Asn Leu Leu Val Glu Pro Glu Ser Leu Arg Thr Tyr Arg Leu
145                 150                 155                 160

Trp Pro Thr Gln Pro Pro Ser Phe Arg Asp Val Leu Cys Glu Tyr Thr
                165                 170                 175

Val Arg Cys Lys Ala Ala Thr Asn Ile Val Ile Arg Asn Met Ala Lys
            180                 185                 190

Met Leu Asn Leu Gln Glu Glu His Leu Val Asn Met Ile Gly Asp Asn
        195                 200                 205

Ser Ile Thr Gln Ala Ile Phe Asn Tyr Tyr Pro Gln Cys Pro Arg Pro
    210                 215                 220

Asp His Val Leu Gly Leu Lys Ala His Thr Asp Gly Ser Ile Ile Thr
225                 230                 235                 240

Val Asn Phe Ala Asp Ala Glu Gly Leu Gln Leu Glu Arg Asn Gly Val
                245                 250                 255

Trp Tyr Asn Val Pro Ile Val Pro Asn Ala Leu Val Met Asn Ile Gly
            260                 265                 270

Asp Ile Met Glu Ile Leu Ser Asn Gly Phe Phe Lys Ser Leu Val His
        275                 280                 285

Arg Val Val Thr Asn Ala Glu Lys Glu Arg Leu Ser Leu Val Leu Val
    290                 295                 300

Tyr Thr Leu Glu Leu Glu Thr Gln Leu Glu Pro Val Ser Glu Leu Val
305                 310                 315                 320

Asp Asp Lys Arg Pro Ala Arg Tyr Met Lys Ile Lys Leu Asn Asp Tyr
                325                 330                 335

Met Glu Lys Tyr His Asp Thr Tyr Ala Thr Gly Thr Leu Ala Ile Asp
            340                 345                 350

Gly Val Lys Ile
        355
```

<210> SEQ ID NO 13
<211> LENGTH: 1071
<212> TYPE: DNA
<213> ORGANISM: Triticum aestivum
<220> FEATURE:
<221> NAME/KEY: CDS
<222> LOCATION: (1)..(1071)

<400> SEQUENCE: 13

| | | | | | | | | | | | | | | | | |
|---|---|---|---|---|---|---|---|---|---|---|---|---|---|---|---|---|
| atg | gcc | gct | tct | gac | gaa | tca | ccg | atg | gtt | cgg | cca | act | gtc | caa | gag | 48 |
| Met | Ala | Ala | Ser | Asp | Glu | Ser | Pro | Met | Val | Arg | Pro | Thr | Val | Gln | Glu | |
| 1 | | | | 5 | | | | | 10 | | | | | 15 | | |
| ctt | acc | gcg | gca | gga | gtg | gag | gaa | cca | ccg | agg | cag | tac | gtg | ctc | ccc | 96 |
| Leu | Thr | Ala | Ala | Gly | Val | Glu | Glu | Pro | Pro | Arg | Gln | Tyr | Val | Leu | Pro | |
| | | | 20 | | | | | 25 | | | | | 30 | | | |
| gag | caa | gat | cgc | cat | ggc | gac | cta | ctt | gcc | gcc | gac | gag | ttt | ccg | gaa | 144 |
| Glu | Gln | Asp | Arg | His | Gly | Asp | Leu | Leu | Ala | Ala | Asp | Glu | Phe | Pro | Glu | |
| | | 35 | | | | | 40 | | | | | 45 | | | | |
| ccc | aca | ccg | ctg | atc | gac | cta | agc | cgt | cta | acc | gat | gcg | gat | gag | gcc | 192 |
| Pro | Thr | Pro | Leu | Ile | Asp | Leu | Ser | Arg | Leu | Thr | Asp | Ala | Asp | Glu | Ala | |
| | 50 | | | | | 55 | | | | | 60 | | | | | |
| gaa | aga | ctc | cgt | gct | gcg | ttg | cag | act | tgg | ggc | ttc | ttc | ctc | gct | acg | 240 |
| Glu | Arg | Leu | Arg | Ala | Ala | Leu | Gln | Thr | Trp | Gly | Phe | Phe | Leu | Ala | Thr | |
| 65 | | | | | 70 | | | | | 75 | | | | | 80 | |
| aat | cat | ggc | att | gag | gac | tca | ctt | atg | gac | gcc | atg | atg | tcc | gtt | tcc | 288 |
| Asn | His | Gly | Ile | Glu | Asp | Ser | Leu | Met | Asp | Ala | Met | Met | Ser | Val | Ser | |
| | | | | 85 | | | | | 90 | | | | | 95 | | |
| aga | gag | ttc | ttc | agg | caa | cca | gcc | gag | gag | aag | cag | aag | tgc | agc | aac | 336 |
| Arg | Glu | Phe | Phe | Arg | Gln | Pro | Ala | Glu | Glu | Lys | Gln | Lys | Cys | Ser | Asn | |
| | | | 100 | | | | | 105 | | | | | 110 | | | |
| ctg | gtc | gat | ggg | aat | ggt | aag | gac | tac | cag | gta | gag | gga | tat | ggc | agt | 384 |
| Leu | Val | Asp | Gly | Asn | Gly | Lys | Asp | Tyr | Gln | Val | Glu | Gly | Tyr | Gly | Ser | |
| | | 115 | | | | | 120 | | | | | 125 | | | | |
| gac | aag | gtg | gtg | tcc | gaa | gat | caa | gtc | ctc | aac | tgg | agt | gac | agg | ctg | 432 |
| Asp | Lys | Val | Val | Ser | Glu | Asp | Gln | Val | Leu | Asn | Trp | Ser | Asp | Arg | Leu | |
| | 130 | | | | | 135 | | | | | 140 | | | | | |
| cac | ttg | aga | gtc | gaa | cca | gag | gac | gag | aga | aac | ttc | gcc | aaa | tgg | cca | 480 |
| His | Leu | Arg | Val | Glu | Pro | Glu | Asp | Glu | Arg | Asn | Phe | Ala | Lys | Trp | Pro | |
| 145 | | | | | 150 | | | | | 155 | | | | | 160 | |
| tct | cac | cca | gag | tcg | ttt | cgt | gac | gtg | ctg | caa | gag | tat | gcc | tct | cgc | 528 |
| Ser | His | Pro | Glu | Ser | Phe | Arg | Asp | Val | Leu | Gln | Glu | Tyr | Ala | Ser | Arg | |
| | | | | 165 | | | | | 170 | | | | | 175 | | |
| acc | aag | aag | atc | agg | gat | ctt | gtc | ctt | cgc | tca | att | gct | gag | ctg | ctc | 576 |
| Thr | Lys | Lys | Ile | Arg | Asp | Leu | Val | Leu | Arg | Ser | Ile | Ala | Glu | Leu | Leu | |
| | | | 180 | | | | | 185 | | | | | 190 | | | |
| gag | att | gac | gag | gat | tac | ttc | gtc | aac | caa | att | tcg | aac | aag | gca | tcc | 624 |
| Glu | Ile | Asp | Glu | Asp | Tyr | Phe | Val | Asn | Gln | Ile | Ser | Asn | Lys | Ala | Ser | |
| | | 195 | | | | | 200 | | | | | 205 | | | | |
| ggc | ttt | gcg | cgc | ttc | aac | tac | tac | cct | cct | tgt | cca | cgc | ccc | gat | ttg | 672 |
| Gly | Phe | Ala | Arg | Phe | Asn | Tyr | Tyr | Pro | Pro | Cys | Pro | Arg | Pro | Asp | Leu | |
| | 210 | | | | | 215 | | | | | 220 | | | | | |
| gtg | ctt | ggg | ttg | agg | cct | cac | tcg | gac | gga | ggt | ctg | ctc | acg | atc | ctg | 720 |
| Val | Leu | Gly | Leu | Arg | Pro | His | Ser | Asp | Gly | Gly | Leu | Leu | Thr | Ile | Leu | |
| 225 | | | | | 230 | | | | | 235 | | | | | 240 | |
| ttc | aat | gac | gac | aac | gtt | ggt | gga | ctc | cag | ata | cag | agg | gat | ggg | agg | 768 |
| Phe | Asn | Asp | Asp | Asn | Val | Gly | Gly | Leu | Gln | Ile | Gln | Arg | Asp | Gly | Arg | |
| | | | | 245 | | | | | 250 | | | | | 255 | | |
| tgg | tac | aat | gtg | ccg | acg | aaa | ccc | cac | act | ctg | ctc | atc | aac | ctc | gca | 816 |
| Trp | Tyr | Asn | Val | Pro | Thr | Lys | Pro | His | Thr | Leu | Leu | Ile | Asn | Leu | Ala | |
| | | | 260 | | | | | 265 | | | | | 270 | | | |

```
gac tgc ctg gaa atc atg aac aat ggc atc ttt agg tcc ccg ttc cat        864
Asp Cys Leu Glu Ile Met Asn Asn Gly Ile Phe Arg Ser Pro Phe His
            275                 280                 285 cgg gtt gtg acc aac gtg gag aag gac cgc ttg agc ctc gcg gtt ttc        912
Arg Val Val Thr Asn Val Glu Lys Asp Arg Leu Ser Leu Ala Val Phe
        290                 295                 300 tac gcc gta gat gcg gag aca atg ctc gaa ccc gct cca ggc ctc ctg        960
Tyr Ala Val Asp Ala Glu Thr Met Leu Glu Pro Ala Pro Gly Leu Leu
305                 310                 315                 320 gat gac aag agg cct agc cgg tat cgg aag atg ttg gcc aag gac ttt       1008
Asp Asp Lys Arg Pro Ser Arg Tyr Arg Lys Met Leu Ala Lys Asp Phe
                325                 330                 335 gtc gca ggc ctc ttc gag cac ttc cgc caa ggg aaa cgg ttt atc gac       1056
Val Ala Gly Leu Phe Glu His Phe Arg Gln Gly Lys Arg Phe Ile Asp
            340                 345                 350 acc ctc aag ata tga                                                    1071
Thr Leu Lys Ile
        355

<210> SEQ ID NO 14
<211> LENGTH: 356
<212> TYPE: PRT
<213> ORGANISM: Triticum aestivum

<400> SEQUENCE: 14

Met Ala Ala Ser Asp Glu Ser Pro Met Val Arg Pro Thr Val Gln Glu
1               5                   10                  15

Leu Thr Ala Ala Gly Val Glu Glu Pro Pro Arg Gln Tyr Val Leu Pro
            20                  25                  30

Glu Gln Asp Arg His Gly Asp Leu Leu Ala Ala Asp Glu Phe Pro Glu
        35                  40                  45

Pro Thr Pro Leu Ile Asp Leu Ser Arg Leu Thr Asp Ala Asp Glu Ala
    50                  55                  60

Glu Arg Leu Arg Ala Ala Leu Gln Thr Trp Gly Phe Phe Leu Ala Thr
65                  70                  75                  80

Asn His Gly Ile Glu Asp Ser Leu Met Asp Ala Met Met Ser Val Ser
                85                  90                  95

Arg Glu Phe Phe Arg Gln Pro Ala Glu Glu Lys Gln Lys Cys Ser Asn
            100                 105                 110

Leu Val Asp Gly Asn Gly Lys Asp Tyr Gln Val Glu Gly Tyr Gly Ser
        115                 120                 125

Asp Lys Val Val Ser Glu Asp Gln Val Leu Asn Trp Ser Asp Arg Leu
    130                 135                 140

His Leu Arg Val Glu Pro Glu Asp Glu Arg Asn Phe Ala Lys Trp Pro
145                 150                 155                 160

Ser His Pro Glu Ser Phe Arg Asp Val Leu Gln Glu Tyr Ala Ser Arg
                165                 170                 175

Thr Lys Lys Ile Arg Asp Leu Val Leu Arg Ser Ile Ala Glu Leu Leu
            180                 185                 190

Glu Ile Asp Glu Asp Tyr Phe Val Asn Gln Ile Ser Asn Lys Ala Ser
        195                 200                 205

Gly Phe Ala Arg Phe Asn Tyr Tyr Pro Pro Cys Pro Arg Pro Asp Leu
    210                 215                 220

Val Leu Gly Leu Arg Pro His Ser Asp Gly Gly Leu Leu Thr Ile Leu
225                 230                 235                 240

Phe Asn Asp Asp Asn Val Gly Gly Leu Gln Ile Gln Arg Asp Gly Arg
```

```
                        245                 250                 255
Trp Tyr Asn Val Pro Thr Lys Pro His Thr Leu Leu Ile Asn Leu Ala
                260                 265                 270

Asp Cys Leu Glu Ile Met Asn Asn Gly Ile Phe Arg Ser Pro Phe His
            275                 280                 285

Arg Val Val Thr Asn Val Glu Lys Asp Arg Leu Ser Leu Ala Val Phe
        290                 295                 300

Tyr Ala Val Asp Ala Glu Thr Met Leu Glu Pro Ala Pro Gly Leu Leu
305                 310                 315                 320

Asp Asp Lys Arg Pro Ser Arg Tyr Arg Lys Met Leu Ala Lys Asp Phe
                325                 330                 335

Val Ala Gly Leu Phe Glu His Phe Arg Gln Gly Lys Arg Phe Ile Asp
            340                 345                 350

Thr Leu Lys Ile
        355

<210> SEQ ID NO 15
<211> LENGTH: 1020
<212> TYPE: DNA
<213> ORGANISM: Triticum aestivum
<220> FEATURE:
<221> NAME/KEY: CDS
<222> LOCATION: (1)..(1020)

<400> SEQUENCE: 15 atg caa gag cct ccg tca cag tac ttg ttg cgc gag caa gag ctg ctt     48
Met Gln Glu Pro Pro Ser Gln Tyr Leu Leu Arg Glu Gln Glu Leu Leu
1               5                   10                  15 gga gct cat ctc gct ggg gct gag atg ccc gaa cca gtg ccg acg att     96
Gly Ala His Leu Ala Gly Ala Glu Met Pro Glu Pro Val Pro Thr Ile
                20                  25                  30 gac cta ggt ctg ttg tcg gct tcg aac gat ccg gaa gaa gcc gca aaa    144
Asp Leu Gly Leu Leu Ser Ala Ser Asn Asp Pro Glu Glu Ala Ala Lys
            35                  40                  45 ctg cgt tct gcc ctt cag acc tgg ggt ttc ttc caa gtc agc aac cat    192
Leu Arg Ser Ala Leu Gln Thr Trp Gly Phe Phe Gln Val Ser Asn His
        50                  55                  60 ggc atg gag gcc tca atg atg gac tcc gtc ttt acc gcg tct agg gaa    240
Gly Met Glu Ala Ser Met Met Asp Ser Val Phe Thr Ala Ser Arg Glu
65                  70                  75                  80 ttc ttc cat ctc cct ctc gaa gag aag aag aag tgc agt aac ctg atc    288
Phe Phe His Leu Pro Leu Glu Glu Lys Lys Lys Cys Ser Asn Leu Ile
                85                  90                  95 gat gga aag cac ttc cag gtt gag ggc tat ggc aac gac caa gta cgc    336
Asp Gly Lys His Phe Gln Val Glu Gly Tyr Gly Asn Asp Gln Val Arg
            100                 105                 110 act cag gac cag agg cta gat tgg agc gat cgg ctt cac ctc cgt gtc    384
Thr Gln Asp Gln Arg Leu Asp Trp Ser Asp Arg Leu His Leu Arg Val
        115                 120                 125 gag cca gaa gga gga cgc aat ctc gtg cac tgg cct acc cac ccc aag    432
Glu Pro Glu Gly Gly Arg Asn Leu Val His Trp Pro Thr His Pro Lys
    130                 135                 140 tcc ttt cgc gat gac ctc cac gag tac acc ctc aag tgc aag cgc att    480
Ser Phe Arg Asp Asp Leu His Glu Tyr Thr Leu Lys Cys Lys Arg Ile
145                 150                 155                 160 aag ggc gac ata ctg agg gca atg gcc aag atc ctt gag ctc gac gag    528
Lys Gly Asp Ile Leu Arg Ala Met Ala Lys Ile Leu Glu Leu Asp Glu
                165                 170                 175 gat tgc ctc gtg aac cag ttc aac agc aat gca ccc aca ttt gca cgg    576
```

```
                Asp Cys Leu Val Asn Gln Phe Asn Ser Asn Ala Pro Thr Phe Ala Arg
                            180                 185                 190 ttc aac cac ttt cca ccg tgc ccc aga cca gat ctc gtg ctg ggc atc           624
Phe Asn His Phe Pro Pro Cys Pro Arg Pro Asp Leu Val Leu Gly Ile
            195                 200                 205 aaa ccg cat gcc gac ttt ccc gcc ttg act gtc ctg ttg atg gac aag           672
Lys Pro His Ala Asp Phe Pro Ala Leu Thr Val Leu Leu Met Asp Lys
210                 215                 220 gat gtc gct ggc ctt cag tac ctc aaa gac ggg aca tgg tac aac gtt           720
Asp Val Ala Gly Leu Gln Tyr Leu Lys Asp Gly Thr Trp Tyr Asn Val
225                 230                 235                 240 ccg gcg gcc tgt gac cac act cta ctg atc agc att ggc ctc acc atg           768
Pro Ala Ala Cys Asp His Thr Leu Leu Ile Ser Ile Gly Leu Thr Met
                245                 250                 255 gag atc atg acg aat ggg atg ttc aca ggg cca atg cac agg gtt gtc           816
Glu Ile Met Thr Asn Gly Met Phe Thr Gly Pro Met His Arg Val Val
            260                 265                 270 acg aat gcg gac aag gag agg att tcc gtg gcg atg ttc tat ggg gtg           864
Thr Asn Ala Asp Lys Glu Arg Ile Ser Val Ala Met Phe Tyr Gly Val
        275                 280                 285 gac cct gag caa gag atc ggt cca ata gcc cac ctc ttg tcc gaa gag           912
Asp Pro Glu Gln Glu Ile Gly Pro Ile Ala His Leu Leu Ser Glu Glu
290                 295                 300 caa cca gcg caa tac cgg aag atg aaa gcc aac gac ctt ctg gtt ctc           960
Gln Pro Ala Gln Tyr Arg Lys Met Lys Ala Asn Asp Leu Leu Val Leu
305                 310                 315                 320 cat cac gag cat tac gcc ggt ggc aga ggc cca agg atc gcg gat gcg          1008
His His Glu His Tyr Ala Gly Gly Arg Gly Pro Arg Ile Ala Asp Ala
                325                 330                 335 ctg aag atc tga                                                          1020
Leu Lys Ile <210> SEQ ID NO 16
<211> LENGTH: 339
<212> TYPE: PRT
<213> ORGANISM: Triticum aestivum

<400> SEQUENCE: 16

Met Gln Glu Pro Pro Ser Gln Tyr Leu Leu Arg Glu Gln Glu Leu Leu
1               5                   10                  15

Gly Ala His Leu Ala Gly Ala Glu Met Pro Glu Pro Val Pro Thr Ile
            20                  25                  30

Asp Leu Gly Leu Leu Ser Ala Ser Asn Asp Pro Glu Glu Ala Ala Lys
        35                  40                  45

Leu Arg Ser Ala Leu Gln Thr Trp Gly Phe Phe Gln Val Ser Asn His
    50                  55                  60

Gly Met Glu Ala Ser Met Met Asp Ser Val Phe Thr Ala Ser Arg Glu
65                  70                  75                  80

Phe Phe His Leu Pro Leu Glu Glu Lys Lys Cys Ser Asn Leu Ile
                85                  90                  95

Asp Gly Lys His Phe Gln Val Glu Gly Tyr Gly Asn Asp Gln Val Arg
            100                 105                 110

Thr Gln Asp Gln Arg Leu Asp Trp Ser Asp Arg Leu His Leu Arg Val
        115                 120                 125

Glu Pro Glu Gly Gly Arg Asn Leu Val His Trp Pro Thr His Pro Lys
    130                 135                 140

Ser Phe Arg Asp Asp Leu His Glu Tyr Thr Leu Lys Cys Lys Arg Ile
145                 150                 155                 160
```

```
Lys Gly Asp Ile Leu Arg Ala Met Ala Lys Ile Leu Glu Leu Asp Glu
            165                 170                 175

Asp Cys Leu Val Asn Gln Phe Asn Ser Asn Ala Pro Thr Phe Ala Arg
        180                 185                 190

Phe Asn His Phe Pro Pro Cys Pro Arg Pro Asp Leu Val Leu Gly Ile
            195                 200                 205

Lys Pro His Ala Asp Phe Pro Ala Leu Thr Val Leu Leu Met Asp Lys
    210                 215                 220

Asp Val Ala Gly Leu Gln Tyr Leu Lys Asp Gly Thr Trp Tyr Asn Val
225                 230                 235                 240

Pro Ala Ala Cys Asp His Thr Leu Leu Ile Ser Ile Gly Leu Thr Met
            245                 250                 255

Glu Ile Met Thr Asn Gly Met Phe Thr Gly Pro Met His Arg Val Val
            260                 265                 270

Thr Asn Ala Asp Lys Glu Arg Ile Ser Val Ala Met Phe Tyr Gly Val
    275                 280                 285

Asp Pro Glu Gln Glu Ile Gly Pro Ile Ala His Leu Leu Ser Glu Glu
    290                 295                 300

Gln Pro Ala Gln Tyr Arg Lys Met Lys Ala Asn Asp Leu Leu Val Leu
305                 310                 315                 320

His His Glu His Tyr Ala Gly Gly Arg Gly Pro Arg Ile Ala Asp Ala
                325                 330                 335

Leu Lys Ile
```

<210> SEQ ID NO 17
<211> LENGTH: 1065
<212> TYPE: DNA
<213> ORGANISM: Zea mays
<220> FEATURE:
<221> NAME/KEY: CDS
<222> LOCATION: (1)..(1065)

<400> SEQUENCE: 17

```
atg gct gat gaa tcg tgg cgc gtc cca act ccc gtc caa gaa ctc gcc    48
Met Ala Asp Glu Ser Trp Arg Val Pro Thr Pro Val Gln Glu Leu Ala
1               5                   10                  15 gcg ggt gta gtt gag cca cct aca cag ttc gtt ctc caa gag caa gat    96
Ala Gly Val Val Glu Pro Pro Thr Gln Phe Val Leu Gln Glu Gln Asp
            20                  25                  30 aga cca ggc tca ggg acg ctc ctc ttt gcc acc gat atg ccg gag cca   144
Arg Pro Gly Ser Gly Thr Leu Leu Phe Ala Thr Asp Met Pro Glu Pro
        35                  40                  45 att ccg gtc gtg gac ctt tcc agg ctc gct gct gcc gat gaa gcg agc   192
Ile Pro Val Val Asp Leu Ser Arg Leu Ala Ala Ala Asp Glu Ala Ser
    50                  55                  60 aaa ctg cgg tca gct ctg gag act tgg ggc ctt ttc ctc gtc aca aag   240
Lys Leu Arg Ser Ala Leu Glu Thr Trp Gly Leu Phe Leu Val Thr Lys
65                  70                  75                  80 cac ggc atc gag gcg tcc ttg atg gat gac gtg atg gca gca tct cgc   288
His Gly Ile Glu Ala Ser Leu Met Asp Asp Val Met Ala Ala Ser Arg
                85                  90                  95 gac ttc ttc tac caa cct ctg gag gcc aag caa gag tac agc aac ctc   336
Asp Phe Phe Tyr Gln Pro Leu Glu Ala Lys Gln Glu Tyr Ser Asn Leu
            100                 105                 110 att gga ggc aag agg ttt cag atg gag ggc tat ggg aac gac atg gtc   384
Ile Gly Gly Lys Arg Phe Gln Met Glu Gly Tyr Gly Asn Asp Met Val
        115                 120                 125
```

```
aag tcg aaa gac cag atc ctc gac tgg cag gat agg ctg cag ctg cgt    432
Lys Ser Lys Asp Gln Ile Leu Asp Trp Gln Asp Arg Leu Gln Leu Arg
    130                 135                 140 gtt gag ccg caa gac gag cgg aac ttg gcc tac tgg ccc aaa cat ccc    480
Val Glu Pro Gln Asp Glu Arg Asn Leu Ala Tyr Trp Pro Lys His Pro
145                 150                 155                 160 gac tcg ttt agg gac cta ctc gaa aag tac gcc agc aaa acc aag ata    528
Asp Ser Phe Arg Asp Leu Leu Glu Lys Tyr Ala Ser Lys Thr Lys Ile
                165                 170                 175 gtc cgg aac aag gtg ctt cgc gct atg ggt aag act ctc gag ctt ggc    576
Val Arg Asn Lys Val Leu Arg Ala Met Gly Lys Thr Leu Glu Leu Gly
            180                 185                 190 gag gac tac ttc atc tcc cag att ggc gat cgt gcg tca gcc ata gca    624
Glu Asp Tyr Phe Ile Ser Gln Ile Gly Asp Arg Ala Ser Ala Ile Ala
        195                 200                 205 cgc ttc aac tac tat cca ccg tgc cca aga ccc gat ctt gtg ttc ggg    672
Arg Phe Asn Tyr Tyr Pro Pro Cys Pro Arg Pro Asp Leu Val Phe Gly
    210                 215                 220 atc aag cct cac agt gac gga ggc gcg gtc acc ata ctg ctg gtt gac    720
Ile Lys Pro His Ser Asp Gly Gly Ala Val Thr Ile Leu Leu Val Asp
225                 230                 235                 240 aag gat gtg ggt ggc ttg caa gtg cag aag gac gga gtg tgg tac acg    768
Lys Asp Val Gly Gly Leu Gln Val Gln Lys Asp Gly Val Trp Tyr Thr
                245                 250                 255 gtc cca tcc atg ccg cat acc ctg cta gtg aat ctc ggc gac agc atg    816
Val Pro Ser Met Pro His Thr Leu Leu Val Asn Leu Gly Asp Ser Met
            260                 265                 270 gag atc atg aat aac ggt atc ttc aag tct ccc gta cac aga gtg gtg    864
Glu Ile Met Asn Asn Gly Ile Phe Lys Ser Pro Val His Arg Val Val
        275                 280                 285 acc aat gcg gag aag gaa cgg ctg agt cta gcc atg ttt tac ggg gtt    912
Thr Asn Ala Glu Lys Glu Arg Leu Ser Leu Ala Met Phe Tyr Gly Val
    290                 295                 300 gag gga caa cgc gtt ctg gag cca gcg ctc ggc ttg ctc ggt gag gaa    960
Glu Gly Gln Arg Val Leu Glu Pro Ala Leu Gly Leu Leu Gly Glu Glu
305                 310                 315                 320 cgt cct gca agg tat cgc aag atc atg gcc tcc gac tac atc atc ggg   1008
Arg Pro Ala Arg Tyr Arg Lys Ile Met Ala Ser Asp Tyr Ile Ile Gly
                325                 330                 335 ttg agg caa ggg att gcc gag gga cag agg ttc atc gaa acg ctc aag   1056
Leu Arg Gln Gly Ile Ala Glu Gly Gln Arg Phe Ile Glu Thr Leu Lys
            340                 345                 350 att tga taa                                                        1065
Ile
```

<210> SEQ ID NO 18
<211> LENGTH: 353
<212> TYPE: PRT
<213> ORGANISM: Zea mays

<400> SEQUENCE: 18

```
Met Ala Asp Glu Ser Trp Arg Val Pro Thr Pro Val Gln Glu Leu Ala
1               5                   10                  15

Ala Gly Val Val Glu Pro Pro Thr Gln Phe Val Leu Gln Glu Gln Asp
            20                  25                  30

Arg Pro Gly Ser Gly Thr Leu Leu Phe Ala Thr Asp Met Pro Glu Pro
        35                  40                  45

Ile Pro Val Val Asp Leu Ser Arg Leu Ala Ala Ala Asp Glu Ala Ser
    50                  55                  60
```

```
Lys Leu Arg Ser Ala Leu Glu Thr Trp Gly Leu Phe Leu Val Thr Lys
 65                  70                  75                  80

His Gly Ile Glu Ala Ser Leu Met Asp Val Met Ala Ala Ser Arg
                 85                  90                  95

Asp Phe Phe Tyr Gln Pro Leu Glu Ala Lys Gln Glu Tyr Ser Asn Leu
                100                 105                 110

Ile Gly Gly Lys Arg Phe Gln Met Glu Gly Tyr Gly Asn Asp Met Val
            115                 120                 125

Lys Ser Lys Asp Gln Ile Leu Asp Trp Gln Asp Arg Leu Gln Leu Arg
130                 135                 140

Val Glu Pro Gln Asp Glu Arg Asn Leu Ala Tyr Trp Pro Lys His Pro
145                 150                 155                 160

Asp Ser Phe Arg Asp Leu Leu Glu Lys Tyr Ala Ser Lys Thr Lys Ile
                165                 170                 175

Val Arg Asn Lys Val Leu Arg Ala Met Gly Lys Thr Leu Glu Leu Gly
            180                 185                 190

Glu Asp Tyr Phe Ile Ser Gln Ile Gly Asp Arg Ala Ser Ala Ile Ala
        195                 200                 205

Arg Phe Asn Tyr Tyr Pro Pro Cys Pro Arg Pro Asp Leu Val Phe Gly
210                 215                 220

Ile Lys Pro His Ser Asp Gly Ala Val Thr Ile Leu Leu Val Asp
225                 230                 235                 240

Lys Asp Val Gly Gly Leu Gln Val Gln Lys Asp Gly Val Trp Tyr Thr
                245                 250                 255

Val Pro Ser Met Pro His Thr Leu Leu Val Asn Leu Gly Asp Ser Met
            260                 265                 270

Glu Ile Met Asn Asn Gly Ile Phe Lys Ser Pro Val His Arg Val Val
        275                 280                 285

Thr Asn Ala Glu Lys Glu Arg Leu Ser Leu Ala Met Phe Tyr Gly Val
290                 295                 300

Glu Gly Gln Arg Val Leu Glu Pro Ala Leu Gly Leu Leu Gly Glu Glu
305                 310                 315                 320

Arg Pro Ala Arg Tyr Arg Lys Ile Met Ala Ser Asp Tyr Ile Ile Gly
                325                 330                 335

Leu Arg Gln Gly Ile Ala Glu Gly Gln Arg Phe Ile Glu Thr Leu Lys
            340                 345                 350

Ile

<210> SEQ ID NO 19
<211> LENGTH: 1059
<212> TYPE: DNA
<213> ORGANISM: Zea mays
<220> FEATURE:
<221> NAME/KEY: CDS
<222> LOCATION: (1)..(1059)

<400> SEQUENCE: 19 atg gcg gtc gag agc tgg aca gtg cct acg ccg gtc aag gac ctt gct    48
Met Ala Val Glu Ser Trp Thr Val Pro Thr Pro Val Lys Asp Leu Ala
 1               5                  10                  15 gcc ctc gtt gat gag cct ccc tcc agg ttc gtc cag agg gaa gag cat    96
Ala Leu Val Asp Glu Pro Pro Ser Arg Phe Val Gln Arg Glu Glu His
             20                  25                  30 agg cct ggt tcc ctg atg ctt gcc gca gac atg ccg gat ccg ctg cca   144
Arg Pro Gly Ser Leu Met Leu Ala Ala Asp Met Pro Asp Pro Leu Pro
         35                  40                  45
```

| | |
|---|---|
| att gtg gac ctc aac aag ctt agc act gca gac gaa gcc gcg aaa ctg<br>Ile Val Asp Leu Asn Lys Leu Ser Thr Ala Asp Glu Ala Ala Lys Leu<br>50              55                  60 | 192 |
| cgt tca gcg ctg caa aca tgg ggt ctt ttc ctc gcc acc aat cac gga<br>Arg Ser Ala Leu Gln Thr Trp Gly Leu Phe Leu Ala Thr Asn His Gly<br>65              70                  75              80 | 240 |
| atc gac gct agc ctc atg gag gac ctc atg gaa gcc tca cgg gag ttc<br>Ile Asp Ala Ser Leu Met Glu Asp Leu Met Glu Ala Ser Arg Glu Phe<br>                85                  90                  95 | 288 |
| ttc cac caa ccg cta cag gaa cgc cag aag tac tcg aac ttg cgc gaa<br>Phe His Gln Pro Leu Gln Glu Arg Gln Lys Tyr Ser Asn Leu Arg Glu<br>            100                 105                 110 | 336 |
| ggc act cgg ttt cag ctc gag ggc tac ggg agt gac ccc gta gtg gcc<br>Gly Thr Arg Phe Gln Leu Glu Gly Tyr Gly Ser Asp Pro Val Val Ala<br>        115                 120                 125 | 384 |
| cag gac cac atc ttg gac tgg aat gac agg ttg cag cta aag gtc gag<br>Gln Asp His Ile Leu Asp Trp Asn Asp Arg Leu Gln Leu Lys Val Glu<br>    130                 135                 140 | 432 |
| cca gag gat gag aga tcg ctg gca caa tgg ccg aag tac cct gag tcc<br>Pro Glu Asp Glu Arg Ser Leu Ala Gln Trp Pro Lys Tyr Pro Glu Ser<br>145                 150                 155                 160 | 480 |
| ttt cgc gat ctc cta cac gag tat gcg tcc aag acg aag tct atg agg<br>Phe Arg Asp Leu Leu His Glu Tyr Ala Ser Lys Thr Lys Ser Met Arg<br>                165                 170                 175 | 528 |
| gat cgg att ttg cgt gct atg gcg aag atc ctc gag ctt gac gag gag<br>Asp Arg Ile Leu Arg Ala Met Ala Lys Ile Leu Glu Leu Asp Glu Glu<br>            180                 185                 190 | 576 |
| gaa ttc atc aag cag ctg gga gca agt ccc caa gcc tat gcc cgc ttc<br>Glu Phe Ile Lys Gln Leu Gly Ala Ser Pro Gln Ala Tyr Ala Arg Phe<br>        195                 200                 205 | 624 |
| aac tac tac cca cca tgc cca agg cca gag ctc gtt ctg ggc atc aaa<br>Asn Tyr Tyr Pro Pro Cys Pro Arg Pro Glu Leu Val Leu Gly Ile Lys<br>    210                 215                 220 | 672 |
| gcg cac tca gac ggc cca gtg ctc acc gtt ctg ctg gta gat agg gag<br>Ala His Ser Asp Gly Pro Val Leu Thr Val Leu Leu Val Asp Arg Glu<br>225                 230                 235                 240 | 720 |
| gtc ggt ggg ttg caa gtg caa aga gag aac acc tgg ttt aac gtt ccc<br>Val Gly Gly Leu Gln Val Gln Arg Glu Asn Thr Trp Phe Asn Val Pro<br>                245                 250                 255 | 768 |
| ttt gtg cca cat acc ctc gtg atc aac ctg ggc gat agc cta gag atc<br>Phe Val Pro His Thr Leu Val Ile Asn Leu Gly Asp Ser Leu Glu Ile<br>            260                 265                 270 | 816 |
| atg tcc aat ggg atc ttc aag tct ccc gtc cat agg gtc gtg acg aat<br>Met Ser Asn Gly Ile Phe Lys Ser Pro Val His Arg Val Val Thr Asn<br>        275                 280                 285 | 864 |
| gcc gag aaa gag cgc att tct ctg gct atg ctc tac gcg gtt gaa cgg<br>Ala Glu Lys Glu Arg Ile Ser Leu Ala Met Leu Tyr Ala Val Glu Arg<br>    290                 295                 300 | 912 |
| gat aac gtg ttg caa cca gcc gct ggg ctc ctc gac gag aaa cgt ccg<br>Asp Asn Val Leu Gln Pro Ala Ala Gly Leu Leu Asp Glu Lys Arg Pro<br>305                 310                 315                 320 | 960 |
| gca cgc tat aga cgc ata act gag gcc gac ttc ctt gag gga gtc aag<br>Ala Arg Tyr Arg Arg Ile Thr Glu Ala Asp Phe Leu Glu Gly Val Lys<br>                325                 330                 335 | 1008 |
| gaa cac ttc tcg aag ggc att cgg atg atc gaa acc ctc aag ata tga<br>Glu His Phe Ser Lys Gly Ile Arg Met Ile Glu Thr Leu Lys Ile<br>            340                 345                 350 | 1056 |
| taa | 1059 |

<210> SEQ ID NO 20
<211> LENGTH: 351
<212> TYPE: PRT
<213> ORGANISM: Zea mays

<400> SEQUENCE: 20

Met Ala Val Glu Ser Trp Thr Val Pro Thr Pro Val Lys Asp Leu Ala
1               5                   10                  15

Ala Leu Val Asp Glu Pro Pro Ser Arg Phe Val Gln Arg Glu Glu His
            20                  25                  30

Arg Pro Gly Ser Leu Met Leu Ala Ala Asp Met Pro Asp Pro Leu Pro
        35                  40                  45

Ile Val Asp Leu Asn Lys Leu Ser Thr Ala Asp Glu Ala Ala Lys Leu
    50                  55                  60

Arg Ser Ala Leu Gln Thr Trp Gly Leu Phe Leu Ala Thr Asn His Gly
65                  70                  75                  80

Ile Asp Ala Ser Leu Met Glu Asp Leu Met Glu Ala Ser Arg Glu Phe
                85                  90                  95

Phe His Gln Pro Leu Gln Glu Arg Gln Lys Tyr Ser Asn Leu Arg Glu
            100                 105                 110

Gly Thr Arg Phe Gln Leu Glu Gly Tyr Gly Ser Asp Pro Val Val Ala
        115                 120                 125

Gln Asp His Ile Leu Asp Trp Asn Asp Arg Leu Gln Leu Lys Val Glu
    130                 135                 140

Pro Glu Asp Glu Arg Ser Leu Ala Gln Trp Pro Lys Tyr Pro Glu Ser
145                 150                 155                 160

Phe Arg Asp Leu Leu His Glu Tyr Ala Ser Lys Thr Lys Ser Met Arg
                165                 170                 175

Asp Arg Ile Leu Arg Ala Met Ala Lys Ile Leu Glu Leu Asp Glu Glu
            180                 185                 190

Glu Phe Ile Lys Gln Leu Gly Ala Ser Pro Gln Ala Tyr Ala Arg Phe
        195                 200                 205

Asn Tyr Tyr Pro Pro Cys Pro Arg Pro Glu Leu Val Leu Gly Ile Lys
    210                 215                 220

Ala His Ser Asp Gly Pro Val Leu Thr Val Leu Leu Val Asp Arg Glu
225                 230                 235                 240

Val Gly Gly Leu Gln Val Gln Arg Glu Asn Thr Trp Phe Asn Val Pro
                245                 250                 255

Phe Val Pro His Thr Leu Val Ile Asn Leu Gly Asp Ser Leu Glu Ile
            260                 265                 270

Met Ser Asn Gly Ile Phe Lys Ser Pro Val His Arg Val Val Thr Asn
        275                 280                 285

Ala Glu Lys Glu Arg Ile Ser Leu Ala Met Leu Tyr Ala Val Glu Arg
    290                 295                 300

Asp Asn Val Leu Gln Pro Ala Ala Gly Leu Leu Asp Glu Lys Arg Pro
305                 310                 315                 320

Ala Arg Tyr Arg Arg Ile Thr Glu Ala Asp Phe Leu Glu Gly Val Lys
                325                 330                 335

Glu His Phe Ser Lys Gly Ile Arg Met Ile Glu Thr Leu Lys Ile
            340                 345                 350

<210> SEQ ID NO 21
<211> LENGTH: 1059
<212> TYPE: DNA
<213> ORGANISM: Sorghum bicolor
<220> FEATURE:

```
<221> NAME/KEY: CDS
<222> LOCATION: (1)..(1059)

<400> SEQUENCE: 21 atg gca ggg gaa tcg tgg aag gtt ccg aca ccc gtc aaa gac ttg gca      48
Met Ala Gly Glu Ser Trp Lys Val Pro Thr Pro Val Lys Asp Leu Ala
1               5                   10                  15 gcg ctc gta gaa gag cca cca tcc cag ttc gta cag agg gag gag gac      96
Ala Leu Val Glu Glu Pro Pro Ser Gln Phe Val Gln Arg Glu Glu Asp
                20                  25                  30 cgt ccc ggc tcg ctc atg ctg gca gcg gat atg cca gat cca ctc ccc     144
Arg Pro Gly Ser Leu Met Leu Ala Ala Asp Met Pro Asp Pro Leu Pro
            35                  40                  45 ata gtg gac ctt gac aag atg agc aca gct gat gag gct acc aaa cta     192
Ile Val Asp Leu Asp Lys Met Ser Thr Ala Asp Glu Ala Thr Lys Leu
        50                  55                  60 cgc tct gcc ctc caa act tgg gga ctt ttc ctt gcc acc aat cac ggc     240
Arg Ser Ala Leu Gln Thr Trp Gly Leu Phe Leu Ala Thr Asn His Gly
65                  70                  75                  80 atc gat gtc agc ttg atg gag gac ctg atg aag gcc agt agg gag ttc     288
Ile Asp Val Ser Leu Met Glu Asp Leu Met Lys Ala Ser Arg Glu Phe
                85                  90                  95 ttc aac cag cca ctg caa gag agg caa aag tac tcc aat ctc aga gaa     336
Phe Asn Gln Pro Leu Gln Glu Arg Gln Lys Tyr Ser Asn Leu Arg Glu
                100                 105                 110 ggc acg cgg ttt cag ctc gag ggg tat ggc agc gat ccg gtg ata gcc     384
Gly Thr Arg Phe Gln Leu Glu Gly Tyr Gly Ser Asp Pro Val Ile Ala
            115                 120                 125 caa gac cac att ctc gac tgg agc gac aga ctc caa ctg aag gtt gag     432
Gln Asp His Ile Leu Asp Trp Ser Asp Arg Leu Gln Leu Lys Val Glu
        130                 135                 140 ccg gag gat gaa cgg aat ctc gct caa tgg cca aaa cac ccc gaa tcc     480
Pro Glu Asp Glu Arg Asn Leu Ala Gln Trp Pro Lys His Pro Glu Ser
145                 150                 155                 160 ttt cgc gac ctc ctg cat gag tac gcg acc aag aca aag act gtc atg     528
Phe Arg Asp Leu Leu His Glu Tyr Ala Thr Lys Thr Lys Thr Val Met
                165                 170                 175 gtg aag atc ctc cgg gca atg gct aag acc cta gag ttg gac gag gag     576
Val Lys Ile Leu Arg Ala Met Ala Lys Thr Leu Glu Leu Asp Glu Glu
                180                 185                 190 gac ttc atc gac cag att ggc ggt agg ccc caa gct tat gcc cgt ttc     624
Asp Phe Ile Asp Gln Ile Gly Gly Arg Pro Gln Ala Tyr Ala Arg Phe
            195                 200                 205 aac tac tac ccg cca tgc cct aga ccc gaa ctg gtg ttg ggg atc aaa     672
Asn Tyr Tyr Pro Pro Cys Pro Arg Pro Glu Leu Val Leu Gly Ile Lys
        210                 215                 220 gcg cat tcc gac ggt cca ctt ctg acc gtc ttg ctg gtc gat cgc gaa     720
Ala His Ser Asp Gly Pro Leu Leu Thr Val Leu Leu Val Asp Arg Glu
225                 230                 235                 240 gtc ggc gga cta cag att cag cgc gaa aac aag tgg ttc aac gtg cca     768
Val Gly Gly Leu Gln Ile Gln Arg Glu Asn Lys Trp Phe Asn Val Pro
                245                 250                 255 tca ata cct cat gcc ctc gtc atc aac ctc gga gac tct ctc gag atc     816
Ser Ile Pro His Ala Leu Val Ile Asn Leu Gly Asp Ser Leu Glu Ile
                260                 265                 270 atg tca aac ggg atc ttt aag agt ccg gtt cac agg gtt gtg acg aat     864
Met Ser Asn Gly Ile Phe Lys Ser Pro Val His Arg Val Val Thr Asn
            275                 280                 285 gcg gag aaa gag cgc att tcg ctt gcc atg ctc tac gcc gtt caa cgc     912
Ala Glu Lys Glu Arg Ile Ser Leu Ala Met Leu Tyr Ala Val Gln Arg
```

```
                290              295              300
gat aac gtg ctt gag cct gcg cct ggc ttg ctg gat gag aag cgg ccg      960
Asp Asn Val Leu Glu Pro Ala Pro Gly Leu Leu Asp Glu Lys Arg Pro
305              310              315              320 gcc aag tac agg cgt atc acg gaa gcc cac ttt ctg gag gga gtg aag     1008
Ala Lys Tyr Arg Arg Ile Thr Glu Ala His Phe Leu Glu Gly Val Lys
            325              330              335 gag cac ttc tca aag ggt atg agg atg atc gag act ctg aag atc tga    1056
Glu His Phe Ser Lys Gly Met Arg Met Ile Glu Thr Leu Lys Ile
            340              345              350 taa                                                                 1059

<210> SEQ ID NO 22
<211> LENGTH: 351
<212> TYPE: PRT
<213> ORGANISM: Sorghum bicolor

<400> SEQUENCE: 22

Met Ala Gly Glu Ser Trp Lys Val Pro Thr Pro Val Lys Asp Leu Ala
1               5                   10                  15

Ala Leu Val Glu Glu Pro Pro Ser Gln Phe Val Gln Arg Glu Glu Asp
            20                  25                  30

Arg Pro Gly Ser Leu Met Leu Ala Ala Asp Met Pro Asp Pro Leu Pro
        35                  40                  45

Ile Val Asp Leu Asp Lys Met Ser Thr Ala Asp Glu Ala Thr Lys Leu
    50                  55                  60

Arg Ser Ala Leu Gln Thr Trp Gly Leu Phe Leu Ala Thr Asn His Gly
65                  70                  75                  80

Ile Asp Val Ser Leu Met Glu Asp Leu Met Lys Ala Ser Arg Glu Phe
                85                  90                  95

Phe Asn Gln Pro Leu Gln Glu Arg Gln Lys Tyr Ser Asn Leu Arg Glu
            100                 105                 110

Gly Thr Arg Phe Gln Leu Glu Gly Tyr Gly Ser Asp Pro Val Ile Ala
        115                 120                 125

Gln Asp His Ile Leu Asp Trp Ser Asp Arg Leu Gln Leu Lys Val Glu
    130                 135                 140

Pro Glu Asp Glu Arg Asn Leu Ala Gln Trp Pro Lys His Pro Glu Ser
145                 150                 155                 160

Phe Arg Asp Leu Leu His Glu Tyr Ala Thr Lys Thr Lys Thr Val Met
                165                 170                 175

Val Lys Ile Leu Arg Ala Met Ala Lys Thr Leu Glu Leu Asp Glu Glu
            180                 185                 190

Asp Phe Ile Asp Gln Ile Gly Gly Arg Pro Gln Ala Tyr Ala Arg Phe
        195                 200                 205

Asn Tyr Tyr Pro Pro Cys Pro Arg Pro Glu Leu Val Leu Gly Ile Lys
    210                 215                 220

Ala His Ser Asp Gly Pro Leu Leu Thr Val Leu Leu Val Asp Arg Glu
225                 230                 235                 240

Val Gly Gly Leu Gln Ile Gln Arg Glu Asn Lys Trp Phe Asn Val Pro
                245                 250                 255

Ser Ile Pro His Ala Leu Val Ile Asn Leu Gly Asp Ser Leu Glu Ile
            260                 265                 270

Met Ser Asn Gly Ile Phe Lys Ser Pro Val His Arg Val Val Thr Asn
        275                 280                 285

Ala Glu Lys Glu Arg Ile Ser Leu Ala Met Leu Tyr Ala Val Gln Arg
```

```
                290                 295                 300
Asp Asn Val Leu Glu Pro Ala Pro Gly Leu Leu Asp Glu Lys Arg Pro
305                 310                 315                 320

Ala Lys Tyr Arg Arg Ile Thr Glu Ala His Phe Leu Glu Gly Val Lys
            325                 330                 335

Glu His Phe Ser Lys Gly Met Arg Met Ile Glu Thr Leu Lys Ile
        340                 345                 350
```

<210> SEQ ID NO 23
<211> LENGTH: 5
<212> TYPE: PRT
<213> ORGANISM: Artificial Sequence
<220> FEATURE:
<223> OTHER INFORMATION: Synthetic sequence, catalytic triad
<220> FEATURE:
<221> NAME/KEY: misc_feature
<222> LOCATION: (2)..(2)
<223> OTHER INFORMATION: Xaa can be any amino acid.
<220> FEATURE:
<221> NAME/KEY: MISC_FEATURE
<222> LOCATION: (3)..(3)
<223> OTHER INFORMATION: Xaa is Asp or Glu.
<220> FEATURE:
<221> NAME/KEY: misc_feature
<222> LOCATION: (4)..(4)
<223> OTHER INFORMATION: Xaa can be any amino acid.

<400> SEQUENCE: 23

```
His Xaa Xaa Xaa His
1               5
```

<210> SEQ ID NO 24
<211> LENGTH: 40
<212> TYPE: DNA
<213> ORGANISM: Artificial Sequence
<220> FEATURE:
<223> OTHER INFORMATION: Artificially synthesized primer sequence

<400> SEQUENCE: 24
cgacggcaag aacttccaga ttgaagggta tggaactgac                         40

<210> SEQ ID NO 25
<211> LENGTH: 40
<212> TYPE: DNA
<213> ORGANISM: Artificial Sequence
<220> FEATURE:
<223> OTHER INFORMATION: Artificially synthesized primer sequence

<400> SEQUENCE: 25
gtcagttcca taccettcaa tctggaagtt cttgccgtcg                         40

<210> SEQ ID NO 26
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 26
ggtctgatcg gctgcatctc agagttgaac cc                                 32

<210> SEQ ID NO 27
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 27
gggttcaact ctgagatgca gccgatcaga cc                              32

<210> SEQ ID NO 28
<211> LENGTH: 39
<212> TYPE: DNA
<213> ORGANISM: Artificial Sequence
<220> FEATURE:
<223> OTHER INFORMATION: Artificially synthesized primer sequence

<400> SEQUENCE: 28
caacaaagct cctgcatttg caagattcaa ctactaccc                       39

<210> SEQ ID NO 29
<211> LENGTH: 39
<212> TYPE: DNA
<213> ORGANISM: Artificial Sequence
<220> FEATURE:
<223> OTHER INFORMATION: Artificially synthesized primer sequence

<400> SEQUENCE: 29
gggtagtagt tgaatcttgc aaatgcagga gctttgttg                       39

<210> SEQ ID NO 30
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 30
cctcactccg acggcaccct ctttacgatt cttc                            34

<210> SEQ ID NO 31
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 31
gaagaatcgt aaagagggtg ccgtcggagt gagg                            34

<210> SEQ ID NO 32
<211> LENGTH: 38
<212> TYPE: DNA
<213> ORGANISM: Artificial Sequence
<220> FEATURE:
<223> OTHER INFORMATION: Artificially synthesized primer sequence

<400> SEQUENCE: 32
ggatctcact ggccatgtta tacagtgtga atgatgag                        38

<210> SEQ ID NO 33
<211> LENGTH: 38
<212> TYPE: DNA
<213> ORGANISM: Artificial Sequence
<220> FEATURE:
<223> OTHER INFORMATION: Artificially synthesized primer sequence

<400> SEQUENCE: 33
ctcatcattc acactgtata acatggccag tgagatcc                        38

<210> SEQ ID NO 34

```
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 34
ttgtatgcgg tcgatgggga gaag                                          24

<210> SEQ ID NO 35
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 35
catggctacc gacatcctct cac                                           23

<210> SEQ ID NO 36
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 36
catctaaagg tcgagccaga gg                                            22

<210> SEQ ID NO 37
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 37
caacctgtca ttccagtcca agatg                                         25

<210> SEQ ID NO 38
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 38
catctgaagg ttgagccgga gg                                            22

<210> SEQ ID NO 39
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 39
gagtctgtcg ctccagtcga gaatg                                         25

<210> SEQ ID NO 40
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 40
```

```
tttgcccgct tcaactacta c                                                    21

<210> SEQ ID NO 41
<211> LENGTH: 17
<212> TYPE: DNA
<213> ORGANISM: Artificial Sequence
<220> FEATURE:
<223> OTHER INFORMATION: Artificially synthesized primer sequence

<400> SEQUENCE: 41
ggcttgggga cttgctc                                                         17

<210> SEQ ID NO 42
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 42
cgcatcaggc aggaaatatt taggtgac                                             28

<210> SEQ ID NO 43
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 43
ggagaaaggc ggacaggtat ccggtaag                                             28
```

US 11,746,357 B2

METHOD FOR PRODUCING HSL PROTEIN HAVING IMPROVED CATALYTIC ACTIVITY FOR 2-OXOGLUTARIC ACID-DEPENDENTLY OXIDIZING 4-HPPD INHIBITOR

CROSS REFERENCE TO RELATED APPLICATIONS

This application is a National Stage of International Application No. PCT/JP2018/004514 filed Feb. 9, 2018, claiming priority based on Japanese Patent Application No. 2017-023294 filed Feb. 10, 2017.

TECHNICAL FIELD

The present invention relates to a method for producing an HSL protein with increased catalytic activity to oxidize a 4-HPPD inhibitor in a 2-oxoglutarate-dependent manner. In addition, the present invention relates to a method for producing a plant with increased resistance to a 4-HPPD inhibitor, utilizing the above method. Moreover, the present invention also relates to a method for determining resistance of a plant to a 4-HPPD inhibitor and a method for breeding a plant having increased resistance to a 4-HPPD inhibitor, utilizing the above method.

BACKGROUND ART

These days, herbicide components such as benzobicyclon, tefuryltrione, sulcotrione, mesotrione, and tembotrione have been developed and put into practice. These herbicides are all agents (4-HPPD inhibitors) that inhibit the function of 4-hydroxyphenylpyruvate dioxygenase (4-HPPD), and by inhibiting the function of this enzyme, indirectly inhibit the carotenoid synthesis system to cause chlorophyll degradation, whitening plants and withering the plants to death, as shown in FIG. 1. Since the safety to edible cultivars was sufficiently confirmed, these inhibitors have been spreading rapidly in cultivation of rice, and the like.

Meanwhile, some cultivars are weak to the 4-HPPD inhibitors, and it has been reported that there is a possibility that some cultivars are withered to death in some cases. For this reason, there have been demands for the developments of a method for increasing resistance to 4-HPPD inhibitors and a method for reliably identifying resistance or susceptibility to the 4-HPPD inhibitors.

Regarding this point, the present inventors previously found out that a gene (4-hydroxyphenylpyruvate dioxygenase inhibitor sensitive gene No. 1 (HIS1)), which rice has and codes for an oxidase (2-oxoglutarate-dependent dioxygenase) dependent on the divalent iron ion and 2-oxoglutarate, and a homologous gene thereof (HSL1 gene) contribute to the resistance or the susceptibility to the 4-HPPD inhibitors. The present inventors also found that a plant with increased resistance or susceptibility to a 4-HPPD inhibitor can be produced utilizing the gene, and further found that genes having a high homology with the HIS1 gene of rice also existed in barley, sorghum, corn, and the like (PTL 1).

CITATION LIST

Patent Literature

[PTL 1] International Publication No. WO2012/090950

SUMMARY OF INVENTION

Technical Problem

An object of the present invention is to provide a method for producing an HSL protein with increased catalytic activity to oxidize a 4-HPPD inhibitor in a 2-oxoglutarate-dependent manner. Moreover, another object of the present invention is to provide a method for producing a plant with increased resistance to a 4-HPPD inhibitor, utilizing the above method. In addition, still another object of the present invention is to provide a method for determining resistance of a plant to a 4-HPPD inhibitor, and a method for breeding a plant having increased resistance to a 4-HPPD inhibitor, utilizing the above method.

Solution to Problem

As a result of repeated earnest studies, the present inventors have confirmed that the HIS1 protein of rice has an activity to oxidize a 4-HPPD inhibitor in a 2-oxoglutarate-dependent manner and thus decompose the inhibitor. However, on the other hand, the present inventors also found that an OsHSL1 protein exhibiting a high homology with the HIS1 protein (a protein having an amino acid sequence of SEQ ID NO: 4) has little catalytic activity.

Based on the new findings, the present inventors surmised that a slight difference in amino acid sequence between the HIS1 protein and the OsHSL1 protein contributed to the catalytic activity. Then, the present inventors prepared mutants by substituting amino acid residues at sites which were surmised to contribute to these catalytic activities in the OsHSL1 proteins with corresponding amino acid residues of the HIS1 protein and evaluated the catalytic activities in these mutants.

As a result, the present inventors revealed that the catalytic activity was improved by substituting phenylalanine at position 140 in the OsHSL1 protein with a basic amino acid such as histidine. The present inventors also found that in an HIS1-homologous protein (the ZmHSL2 protein and the SbHSL1 protein) in other cultivars, the catalytic activity was improved by mutating an amino acid corresponding to position 140 of the OsHSL1 protein to a basic amino acid. Moreover, the present inventors found out that in *Arabidopsis thaliana* and a 4-HPPD inhibitor susceptible rice cultivar expressing the OsHSL1 protein in which position 140 was substituted with histidine, the resistance to the 4-HPPD inhibitor was improved. These findings have led to the completion of the present invention.

More specifically, the present invention is as follows:

<1> A method for producing an HSL protein with increased catalytic activity to oxidize a 4-HPPD inhibitor in a 2-oxoglutarate-dependent manner, comprising the step of mutating, in an HSL protein, position 140 of an amino acid sequence of SEQ ID NO: 4 or an amino acid corresponding to the position to a basic amino acid.

<2> A method for producing a plant with increased resistance to a 4-HPPD inhibitor, comprising the steps of:

(I) mutating, in an HSL protein of a plant cell, position 140 of an amino acid sequence of SEQ ID NO: 4 or an amino acid corresponding to the position to a basic amino acid; and (II) regenerating a plant from the plant cell in which amino acid mutation is introduced in the step (I).

<3> The production method according to <1> or <2>, wherein the basic amino acid is histidine, lysine, or arginine.

<4> A method for determining resistance of a plant to a 4-HPPD inhibitor, comprising:

detecting a nucleotide which codes for position 140 of an amino acid sequence of SEQ ID NO: 4 or an amino acid corresponding to the position in an HSL gene of a test plant; and if the nucleotide codes for a basic amino acid, determining that the test plant has resistance to a 4-HPPD inhibitor.

<5> A method for breeding a plant having increased resistance to a 4-HPPD inhibitor, the method comprising the steps of:

(a) crossing a plant cultivar having resistance to a 4-HPPD inhibitor with any cultivar;
  (b) determining resistance of an individual obtained by the mating in the step (a) to a 4-HPPD inhibitor by the method according to <4>; and
  (c) selecting an individual determined to have resistant to the 4-HPPD inhibitor.

Advantageous Effects of Invention

According to the present invention, it is possible to increase the catalytic activity of an HSL protein to oxidize a 4-HPPD inhibitor in a 2-oxoglutarate-dependent manner by mutating, in the protein, position 140 of an amino acid sequence of SEQ ID NO: 4 or an amino acid corresponding to the position (hereinafter, also referred to simply as an "amino acid at position 140" to a basic amino acid.

In particular, in a case where the 4-HPPD inhibitor is benzobicyclon (hereinafter, also referred to as "BBC") and its hydrolysate (hereinafter, also referred to as "benzobicyclon hydrolysate" or "BBC-OH"), it is possible to further increase the catalytic activity to oxidize the inhibitor by further substituting position 204 or position 298, or an amino acid corresponding to the position each with another amino acid, in addition to the position 140.

Then, in the present invention, it is also possible to produce a plant with increased resistance to a 4-HPPD inhibitor by utilizing such a method for producing an HSL protein with increased catalytic activity to oxidize a 4-HPPD inhibitor in a 2-oxoglutarate-dependent manner.

Moreover, as described above, based on the finding that an amino acid at position 140 in an HSL protein is an amino acid that affects the catalytic activity, according to the present invention, it is also possible to determine resistance of a test plant to a 4-HPPD inhibitor by detecting a nucleotide which codes for an amino acid at position 140 in an HSL gene of the test plant. In addition, according to the present invention, it is also possible to provide a method for breeding a plant having increased resistance to a 4-HPPD inhibitor, utilizing the above method.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 12 is a table depicting 4-HPPD inhibitor decomposition activity of wild-type and variant proteins.

FIG. 13 is a table depicting 4-HPPD inhibitor decomposition activity of wild-type and variant proteins.

FIG. 14 is a table depicting 4-HPPD inhibitor decomposition activity of wild-type and variant proteins.

FIG. 15 is a table depicting 4-HPPD inhibitor decomposition activity of wild-type and variant proteins.

FIG. 16 is a table depicting 4-HPPD inhibitor decomposition activity of wild-type and variant proteins.

FIG. 17 is a table depicting 4-HPPD inhibitor decomposition activity of wild-type and variant proteins.

DESCRIPTION OF EMBODIMENTS

<Method for Producing HSL Protein with Increased Catalytic Activity to Oxidize 4-HPPD Inhibitor in 2-Oxoglutarate-Dependent Manner>

The present invention provides a method for producing an HSL protein with increased catalytic activity to oxidize a 4-HPPD inhibitor in a 2-oxoglutarate-dependent manner, comprising the step of mutating, in an HSL protein, position 140 of an amino acid sequence of SEQ ID NO: 4 or an amino acid corresponding to the position to a basic amino acid.

Figure 1:
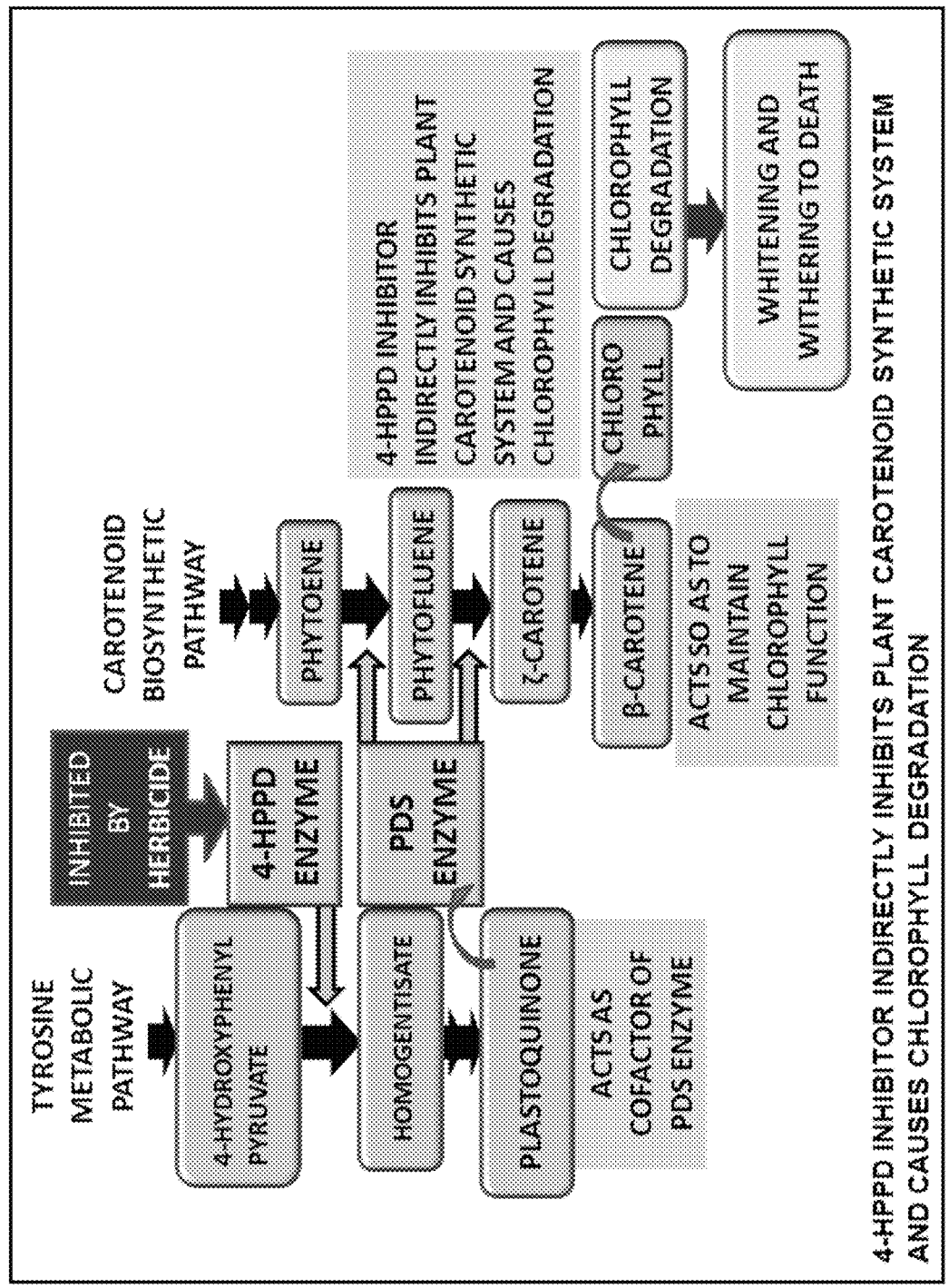
FIG. 1 is a diagram showing an outline and a relation between a tyrosine metabolism pathway and a carotenoid biosynthesis pathway and a 4-HPPD inhibitor.

The "4-HPPD inhibitors" in the present invention mean agents (4-HPPD inhibitors) that inhibit the function of 4-HPPD (4-hydroxyphenylpyruvate dioxygenase, EC Number: 1.13.11.27, 1.14.2.2). As shown in FIG. 1, the 4-HPPD inhibitors inhibit the function of 4-HPPD and thus indirectly inhibit the carotenoid synthesis system to cause chlorophyll degradation, whitening plants and withering the plants to death.

The "4-HPPD inhibitors" in the present invention is classified into (1) cyclohexanedione type, (2) pyrazole type, (3) bicyclo type, (4) isoxazole type (see "From Pesticides to Agrobioregulators—disease, pest, and weed controls at present and in the future", Japan, CMC Publishing Co., Ltd., December, 2009).

(1) The cyclohexanedione type includes, for example, tefuryltrione (CAS registry number: 473278-76-1), sulcotrione (CAS registry number: 99105-77-8), mesotrione (CAS registry number: 104206-82-8), tembotrione (CAS registry number: 335104-84-2), lancotrione (CAS registry number: 1486617-21-3), and 2-[2-nitro-4-(trifluoromethyl)benzoyl]cyclohexane-1,3-di one (Nitisinone, NTBC, CAS registry number: 104206-65-7). (2) The pyrazole type includes, for example, pyrazolynate (CAS registry number: 58011-68-0), benzofenap (CAS registry number: 82692-44-2), pyrazoxyfen (CAS registry number: 71561-11-0), topramezone (CAS registry number: 210631-68-8), and pyrasulfotole (CAS registry number: 365400-11-9).

(3) The bicyclo type includes, for example, benzobicyclon (BBC, CAS registry number: 156963-66-5), benzobicyclon hydrolysate (BBC-OH, CAS registry number: 126656-88-0), and bicyclopyrone (CAS registry number: 352010-68-5).

(4) The isoxazole type includes, for example, isoxaflutole (CAS registry number: 141112-29-0).

The 4-HPPD inhibitor for which the present invention has been made is preferably a 4-HPPD inhibitor of the cyclohexanedione type or the bicyclo type such as benzobicyclon (BBC) or a hydrolysate thereof (benzobicyclon hydrolysate, BBC-OH), tefuryltrione, sulcotrione, mesotrione, tembotrione, lancotrione, bicyclopyrone, or NTBC, more preferably BBC, BBC-OH, tefuryltrione, sulcotrione, mesotrione, or tembotrione, further preferably BBC, BBC-OH, or tefuryltrione, and particularly preferably BBC or BBC-OH.

Note that whether a certain compound has the 4-HPPD inhibitory activity may be determined by analyzing whether the generation of homogentisic acid from 4-hydroxyphenylpyruvic acid, which is promoted by the 4-HPPD enzyme, is suppressed in the presence of the compound (see, for example, the descriptions of Schulz, A. Ort, O. Beyer, P. Kleinig, H. (1993), FEBS Lett., 318, 162-166, and Secor, J. (1994), Plant Physiol., 106, 1429-1433).

The "catalytic activity" in the present invention means, as shown in the following reaction formula, the activity to catalyze the oxidation reaction of a 4-HPPD inhibitor ("R" in the following reaction formula), which serves as a substrate, in a 2-oxoglutarate ("2OG" in the following reaction formula)-dependent manner.

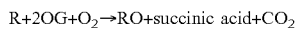

$$R+2OG+O_2 \rightarrow RO+\text{succinic acid}+CO_2$$

Note that this reaction involves the generation of succinic acid and carbon dioxide resulting from the decarboxylation of 2OG.

The HSL protein the catalytic activity of which is increased in the present invention means a protein (HSL protein) having a high homology with a HIS1 protein (typically, a protein having an amino acid sequence of SEQ ID NO: 2). The high homology is a sequence homology of at least 60% or more, and preferably 80% or more (for example, 85%, 90%, 95%, 97%, or 99% or more). The sequence homology may be determined utilizing the BLASTP (amino acid level) program (Altschul et al. J. Mol. Biol., 215: 403-410, 1990). This program is based on the algorithm blast by Karlin and Altschul (Proc. Natl. Acad. Sci. USA, 87: 2264-2268, 1990, Proc. Natl. Acad. Sci. USA, 90: 5873-5877, 1993). When an amino acid sequence is analyzed using the BLASTP, the parameters are set at, for example, score=50, wordlength=3. On the other hand, when an amino acid sequence is analyzed using the Gapped BLAST program, the analysis may be conducted as described in Altschul et al. (Nucleic Acids Res. 25: 3389-3402, 1997). Moreover, when both of the BLAST and the Gapped BLAST program are used, default parameters of each program are used. Specific procedures of these analyzing methods are known.

The source of the "HSL protein" according to the present invention is not particularly limited as long as the source is a plant, which includes, for example, rice, barley, wheat, corn, and sorghum. More specifically, the rice-derived HSL protein includes an OsHSL1 protein (typically, a protein having an amino acid sequence of SEQ ID NO: 4), an OsHSL2 protein (typically, a protein having an amino acid sequence of SEQ ID NO: 6), and the like. The barley-derived HSL protein includes an HvHSL1 protein (typically, a protein having an amino acid sequence of SEQ ID NO: 8), an HvHSL2 protein (typically, a protein having an amino acid sequence of SEQ ID NO: 10), an HvHSL3 protein (typically, a protein having an amino acid sequence of SEQ ID NO: 12), and the like. The wheat-derived HSL protein includes a TaHSL1 protein (typically, a protein having an amino acid sequence of SEQ ID NO: 14), a TaHSL2 protein (typically, a protein having an amino acid sequence of SEQ ID NO: 16), and the like. The corn-derived HSL protein includes a ZmHSL1 protein (typically, a protein having an amino acid sequence of SEQ ID NO: 18), a ZmHSL2 protein (typically, a protein having an amino acid sequence of SEQ ID NO: 20), and the like. The sorghum-derived HSL protein includes a SbHSL1 protein (typically, a protein having an amino acid sequence of SEQ ID NO: 22) and the like. However, the HSL protein according to the present invention is not limited to these. In addition, the amino acid sequence of a protein also changes as a result of mutation of a nucleotide sequence in nature (that is, non-artificially). Hence, it should be appreciated that the target of the present invention encompasses not only the proteins having the above-described typical amino acid sequences but also such natural mutants.

In addition, the "basic amino acid" with which position 140 of an amino acid sequence of SEQ ID NO: 4 or an amino acid corresponding to the position in the above-described HSL protein is substituted in order to increase the catalytic activity includes, for example, histidine, lysine, and arginine, and is preferably histidine from the viewpoint that histidine allows the catalytic activity to be more easily increased.

Moreover, in the present invention, mutation may be introduced into an amino acid at another position instead of mutating position 140 of an amino acid sequence of SEQ ID NO: 4 or an amino acid corresponding to the position to a basic amino acid. Such "mutation" means that one or a plurality of amino acids of an HSL protein are substituted, deleted, added, and/or inserted at positions other than the position 140 of the amino acid sequence of SEQ ID NO: 4 or the portion corresponding to the position. Here, the "plurality" is not particularly limited but is normally 2 to 40, preferably 2 to 30, more preferably 2 to 20, and further preferably 2 to 10 (for example, 2 to 8, 2 to 4, or 2 to 2)

The mutation to be introduced into another portion is not particularly limited. However, from the viewpoint that the catalytic activity to oxidize BBC or BBC—OH is more easily increased, it is preferable that at least one amino acid out of position 204 of the amino acid sequence of SEQ ID NO: 4 or an amino acid corresponding to the position and position 298 of the amino acid sequence of SEQ ID NO: 4 or an amino acid corresponding to the position be each substituted with another amino acid, and it is more preferable that these 2 positions be each substituted with another amino acid. In addition, such "another amino acid" is also not particularly limited. However, from the same viewpoint, it is preferable that position 204 of the amino acid sequence of SEQ ID NO: 4 or an amino acid corresponding to the position be substituted with phenylalanine, and it is preferable that position 298 of the amino acid sequence of SEQ ID NO: 4 or an amino acid corresponding to the position be substituted with leucine.

Note that in the present invention, the "corresponding position" is a position that is matched up with position 140 or the like of the amino acid sequence of SEQ ID NO: 4 when the amino acid sequence of SEQ ID NO: 4 and an amino acid sequence of another SL protein are aligned with each other utilizing amino acid sequence analysis software (GENETYX-MAC, Sequencher, or the like), BLAST (blast.ncbi.nlm.nih.gov/Blast.cgi), CLUSTALW (genome.jp/tools/clustalw/).

In addition, mutagenesis in an HSL protein may be conducted by a mutagenesis method at an amino acid sequence level or by a mutagenesis method at a nucleotide sequence level.

The mutagenesis method at an amino acid sequence level includes a method including chemically synthesizing the mutant using a commercially-available peptide synthesizer based on the amino acid sequence of the HSL protein in which mutation has been introduced at a desired position.

In addition, the mutagenesis at a nucleotide sequence level includes, for example, a site-directed mutagenesis method, a genome editing method, a chemical DNA synthesis method based on nucleotide sequence information coding for an HSL protein in which mutation has been introduced at a desired position. Then, based on the nucleotide prepared by such a mutagenesis method, it is possible to obtain an HSL protein or the like in which position 140 is substituted with a basic amino acid, by utilizing a biological synthesis system or a cell-free protein synthesis system.

The biological synthesis system includes cells such as yeast, plant cells, insect cells, and animal cells. By introducing, into such cells, a cassette (a plasmid vector or the like) capable of expressing a nucleotide coding for the HSL protein or the like in the cells, it is possible to prepare the protein or the like.

In addition, the cell-free protein synthesis system includes, for example, wheat germ-derived, *Escherichia coli*-derived, rabbit reticulocyte-derived, and insect cell-derived synthesis systems. By adding, to such a synthesis system (a cell extract or the like), a cassette (a plasmid vector or the like) capable of expressing a nucleotide coding for the HSL protein or the like in the synthesis system, it is possible to prepare the protein or the like.

Note that among such synthesis systems, a wheat germ-derived cell-free protein synthesis system is preferable from the viewpoint that it is easy to prepare an HSL protein having the catalytic activity as shown in Examples described later. In addition, a synthesis system using tris(2-carboxyethyl)phosphine (TCEP) as a reducing agent is preferable from the viewpoint of suppressing influence on the catalytic activity of an HSL protein.

In addition, whether the catalytic activity has been increased by the above-described mutagenesis can be evaluated by, for example: processing a 4-HPPD inhibitor in the presence of an HSL protein in which mutation has been introduced, divalent iron ions, 2-oxoglutarate, and oxygen; then directly measuring the amount of an oxide of the 4-HPPD inhibitor or measuring the amount of a product (degradant) generated during the oxidation by means of a high-performance liquid chromatography analysis; and comparing the measured amount with the amount in the HSL protein before the introduction of the mutation, as shown in Examples described later. Moreover, as shown in the above-described reaction formula, such reaction also generates not only an oxide of the 4-HPPD inhibitor but also succinic acid at the same time. For this reason, it is also possible to determine whether the catalytic activity has been increased, by measuring the amount of succinic acid generated in the presence of an HSL protein in which mutation has been introduced and comparing the measured amount with the amount in the HSL protein before the introduction of the mutation.

<Method for Producing Plant with Increased Resistance to 4-HPPD Inhibitor>

As described above, by substituting position 140 of an HSL protein with a basic amino acid, it is possible to increase the activity to oxidize and decompose the 4-HPPD inhibitor, and in turn also to improve resistance to the 4-HPPD inhibitor in a plant in which the protein has been expressed, as shown in Examples described later.

Hence, the present invention can also provide a method for producing a plant with increased resistance to a 4-HPPD inhibitor, comprising the steps of:

(I) mutating, in an HSL protein of a plant cell, position 140 of an amino acid sequence of SEQ ID NO: 4 or an amino acid corresponding to the position to a basic amino acid; and (II) regenerating a plant from the plant cell in which amino acid mutation is introduced in the step (I).

The plant whose resistance to a 4-HPPD inhibitor can be increased by the method according to the present invention is not particularly limited, and includes, for example, Poaceae plants such as rice, barley, wheat, sorghum, corn, and creeping bentgrass, Brassicaceae plants such as *Arabidopsis thaliana*, Solanaceae plants such as tomato, Fabaceae plants such as soybean, alfalfa, and Lotus japonicas, Malvaceae plants such as cotton plant, and Chenopodiaceae plants such as sugar beet. Among these plants, 4-HPPD inhibitor-susceptible cultivars are particularly preferable as a target to which the present invention is applied to increase resistance to a 4-HPPD inhibitor. A 4-HPPD inhibitor-susceptible rice cultivar includes, for example, Yamadawara (Kanto 239), Habataki, Takanari, Momiroman, Mizuhochikara, Ruriaoba, Odorokimochi, Hyogo-ushiwakamaru, Kasalath, and the like, but is not limited thereto.

The plant cell of the present invention includes, besides culture cells, cells in plants. Further, the plant cell of the present invention includes plant cells in various forms, for example, suspended culture cells, protoplasts, leaf sections, calli, immature embryos, pollens, and the like.

A method for mutating, in an HSL protein of a plant cell, an amino acid at position 140 to a basic amino acid includes genome editing. In such genome editing, a person skilled in the art can surely substitute an amino acid at position 140 in a plant cell with a basic amino acid, for example, by using fusion proteins such as ZFNs (U.S. Pat. Nos. 6,265,196, 8,524,500, and 7,888,121, European Patent No. 1720995), TALENs (U.S. Pat. Nos. 8,470,973 and 8,586,363), PPR (pentatricopeptide repeat) associated with a nuclease domain (Nakamura et al., Plant Cell Physiol 53: 1171-1179 (2012)), and complexes of guide RNAs and proteins such as CRISPR-Cas9 (U.S. Pat. No. 8,697,359, International Publication No. WO2013/176772), CRISPR-Cpf1 (Zetsche B. et al., Cell, 163 (3): 759-71, (2015)), and Target-AID (K. Nishida et al., Targeted nucleotide editing using hybrid prokaryotic and vertebrate adaptive immune systems, Science, DOI: 10. 1126/science. aaf 8729, (2016)).

In addition, another method for mutating, in an HSL protein of a plant cell, an amino acid at position 140 to a basic amino acid includes a genetic recombination method. In this method, a nucleotide coding for an HSL protein in which an amino acid at position 140 has been substituted with a basic amino acid is introduced into a plant cell, which causes homologous recombination between the nucleotide and an HSL gene on the genome of the cell, substituting the amino acid at the position 140 with the basic amino acid in the cell (what is termed as gene targeting). Note that a person skilled in the art can prepare the nucleotide, for example, by means of a method described in the above-described "mutagenesis at a nucleotide sequence level." In addition, the introduction of the nucleotide into a plant cell can be conducted as appropriate, for example, by using a method described in a method of regenerating a plant, which is described later.

Moreover, as a matter of course, in the method for producing a plant according to the present invention as well, mutation may be introduced not only into position 140 or an amino acid corresponding to the position but also into an amino acid at another position. As the mutation at another position, for example, from the viewpoint that the resistance to BBC or BBC—OH is more easily increased, it is preferable that at least one amino acid out of position 204 of the amino acid sequence of SEQ ID NO: 4 or an amino acid corresponding to the position and position 298 of the amino acid sequence of SEQ ID NO: 4 or an amino acid corresponding to the position be each substituted with another amino acid, and it is more preferable that these 2 positions be each substituted with another amino acid. In addition, such "another amino acid" is also not particularly limited. However, from the same viewpoint, it is preferable that position 204 of the amino acid sequence of SEQ ID NO: 4 or an amino acid corresponding to the position be substituted with phenylalanine, and it is preferable that position 298 of the amino acid sequence of SEQ ID NO: 4 or an amino acid corresponding to the position be substituted with leucine.

In the present invention, the regeneration of a plant from a plant cell in which amino acid mutation has been introduced can be conducted by means of a method publicly known to a person skilled in the art depending on the type of the plant cell.

For example, several techniques of the procedure for producing regenerated rice plants have been already established, such as a method in which a gene is introduced into protoplasts using polyethylene glycol and a plant is regenerated (Datta, S. K. In Gene Transfer To Plants (Potrykus I and Spangenberg Eds.) pp 66-74, 1995); a method in which a gene is introduced into protoplasts using electric pulse and a plant is regenerated (Toki et al. Plant Physiol. 100, 1503-1507, 1992); a method in which a gene is directly introduced into cells by a particle gun method and a plant is regenerated (Christou et al. Bio/technology, 9: 957-962, 1991); and a method in which a gene is introduced using *Agrobacterium* and a plant is regenerated (Hiei et al. Plant J. 6: 271-282, 1994). These are widely used in the technical field of the present invention.

Moreover, the procedure for producing regenerated barley plants includes methods described in Tingay et al. (Tingay S. et al. Plant J. 11: 1369-1376, 1997), Murray et al. (Murray F et al. Plant Cell Report 22: 397-402, 2004), and Travalla et al. (Travalla S et al. Plant Cell Report 23: 780-789, 2005).

In addition, the procedure for producing regenerated wheat plants includes, for example, a method described in "Taiich Ogawa, Japanese Journal of Pesticide Science, 2010, vol. 35, no. 2, pp 160 to 164".

Moreover, the procedure for producing regenerated corn plants includes, for example, methods described in "Ishida Y. et al., Nat Protoc., 2007, vol. 2, no. 7, pp 1614 to 1621", "Hiei Y. et al., Front Plant Sci., Nov. 7, 2014; 5: 628. doi: 10. 3389/fpls. 2014. 00628. eCollection 2014.", and "Hiei et al., Breeding Science Study, 2000, pp 205 to 213".

As the method for regenerating sorghum plants, preferably used are, for example, a method in which a gene is introduced into immature embryos or calli by an *Agrobacterium* method or a particle gun method and a plant is regenerated; and a method in which pollens having a gene introduced therein using ultrasound are used for pollination (J. A. Able et al., In Vitro Cell. Dev. Biol. 37: 341-348, 2001, A. M. Casas et al., Proc. Natl. Acad. Sci. USA 90: 11212-11216, 1993, V. Girijashankar et al., Plant Cell Rep 24: 513-522, 2005, J. M. JEOUNG et al., Hereditas 137: 20-28, 2002, V Girijashankar et al., Plant Cell Rep 24 (9): 513-522, 2005, Zuo-yu Zhao et al., Plant Molecular Biology 44: 789-798, 2000, S. Gurel et al., Plant Cell Rep 28 (3): 429-444, 2009, ZY Zhao, Methods Mol Biol, 343: 233-244, 2006, AK Shrawat and H Lorz, Plant Biotechnol J, 4 (6): 575-603, 2006, D Syamala and P Devi Indian J Exp Biol, 41 (12): 1482-1486, 2003, and Z Gao et al., Plant Biotechnol J, 3 (6): 591-599, 2005).

Further, the procedure for *Arabidopsis thaliana* includes a method by Akama et al. (Akama et al. Plant Cell Reports 12: 7-11, 1992). In the present invention, these methods can be preferably used.

In addition, also regarding other plants, transformation and regeneration to the plants can be conducted using a method described in Tabei et al., (Tabei Y. Ed., "Protocols of Plant Transformation, Kagaku-Dojin Publishing Company, INC, published on Sep. 20, 2012).

Once a plant with increased resistance to a 4-HPPD inhibitor is obtained, it is possible to obtain a progeny from the plant by sexual reproduction or asexual reproduction. In addition, propagation materials (for example, seeds, fruits, spikes, stubs, calli, protoplasts, and the like) are obtained from the plant or a progeny or a clone thereof, from which the plant can also be produced in mass.

In addition, whether the resistance of the plant to a 4-HPPD inhibitor has been improved by the above method can be determined, for example, by examining whether the resistance has been improved in the produced plant by introducing the above-described mutation into the plant, as described in Examples described later. Specifically, with the concentration of a 4-HPPD inhibitor with which a plant before mutagenesis is whitened (for example, 0.05 µM or more in the case where *Arabidopsis thaliana* (*A. thaliana*: ecotype Columbia) is used), if a plant in which the above-described amino acid mutation has been introduced can be grown without being whitened, it can be determined that the resistance of the plant has been increased.

Although the preferred embodiment of the method for producing a plant with increased resistance to a 4-HPPD inhibitor according to the present invention has been described so far, the method for producing a plant according to the present invention is not limited to the above-described embodiment.

As shown in Examples described later, even when homologous recombination does not occur in the above-described genetic recombination method (for example, even when the nucleotide is inserted into the genome of the plant cell at random), it is possible to produce a plant with increased resistance to a 4-HPPD inhibitor by introducing the nucleotide into the plant cell.

Hence, the present invention can also provide a method for producing a plant with increased resistance to a 4-HPPD inhibitor, comprising the steps of:

(I) introducing a nucleotide coding for an HSL protein in which an amino acid at position 140 is substituted with a basic amino acid into a plant cell; and (II) regenerating a plant from the plant cell in which the nucleotide is introduced in the step (I).

As described above, a person skilled in the art can prepare the nucleotide, introduce the nucleotide into a plant cell, and obtain a plant from the plant cell, using publicly-known methods as appropriate. In addition, as described above, also in this production method using the genetic recombination method as well, mutation may be introduced not only into position 140 or an amino acid corresponding to the position but also into an amino acid at another position.

Moreover, in this method, the plant from which the nucleotide is derived and the plant from which the cell is derived may be of the same cultivar (for example, both are rice) as in Example 6 described later. Alternatively, the plant from which the nucleotide is derived and the plant from which the cell is derived may be different cultivars (for example, the former is derived from rice and the latter is derived from *Arabidopsis thaliana*) as in Example 5 described later.

<Method for Determining Resistance of Plant to 4-HPPD Inhibitor>

As shown in Examples described later, the amino acid at position 140 of an HSL protein greatly contributes to the resistance to a 4-HPPD inhibitor. Hence, the present invention also provides a method for determining resistance of a plant to a 4-HPPD inhibitor, comprising: detecting a nucleotide which codes for position 140 of an amino acid sequence of SEQ ID NO: 4 or an amino acid corresponding to the position in an HSL gene of a test plant; and if the nucleotide codes for a basic amino acid, determining that the test plant has resistance to a 4-HPPD inhibitor.

The preparation of a nucleotide from a test plant in the determination method of the present invention can be conducted using a conventional method, for example, the CTAB method. As the plant for preparing a nucleotide, not only grown plants but also seeds or infant plants may be used.

Whether the nucleotide obtained in this way has coded for the amino acid at position 140 of SEQ ID NO: 4 in an HSL gene can be detected by conducting sequencing. Moreover, besides such direct determination of a nucleotide sequence, the analysis can be made indirectly by various methods. Such methods include, for example, the PCR-SSCP (single-strand conformation polymorphism) method, the RFLP method and the PCR-RFLP method utilizing the restriction fragment length polymorphism (RFLP), the denaturant gradient gel electrophoresis (DGGE), the allele-specific oligonucleotide (ASO) hybridization method, and the ribonuclease A mismatch cleavage method.

<Method for Breeding Plant According to Present Invention>

The present invention provides a method for breeding a plant having increased resistance to a 4-HPPD inhibitor. This breeding method comprises the steps of: (a) crossing a plant cultivar having resistance to a 4-HPPD inhibitor with any cultivar; (b) determining resistance of an individual obtained by the mating in the step (a) to a 4-HPPD inhibitor by the above-described <Method for Determining Resistance of Plant to 4-HPPD Inhibitor>; and (c) selecting an individual determined to have resistant to the 4-HPPD inhibitor.

The "any plant cultivar" to be crossed with a plant cultivar having resistance to a 4-HPPD inhibitor includes, for example, a 4-HPPD inhibitor-susceptible cultivar and an individual obtained by crossing a 4-HPPD inhibitor-resistant cultivar and a 4-HPPD inhibitor-susceptible cultivar, but is not limited to these.

Utilizing the breeding method according to the present invention makes it possible to select a 4-HPPD inhibitor-resistant or susceptible cultivar at the stages of seeds and infant plants and thus makes it possible to breed a cultivar having these characters in a short period of time.

Although the preferred embodiments of the present invention have been described so far, the present invention is not limited to the above-described embodiments.

As shown in Examples described later, when BBC or BBC—OH is used as a substrate for a 4-HPPD inhibitor, the catalytic activity to oxidize the agent can be increased also by substituting position 204 and/or position 298 of an HSL protein each with another amino acid (for example, substituting position 204 with phenylalanine and substituting position 298 with leucine) without substituting position 140 with a basic amino acid. In addition, the catalytic activity to oxidize not only BBC and BBC-OH but also sulcotrione, mesotrione, and tembotrione can be increased by substituting position 204 and position 298 of an HSL protein each with another amino acid (for example, substituting position 204 with phenylalanine and substituting position 298 with leucine).

Hence, the present invention provides the following.

<6> A method for producing an HSL protein with increased catalytic activity to oxidize a 4-HPPD inhibitor in a 2-oxoglutarate-dependent manner, comprising the step of: mutating, in an HSL protein, amino acids at position 204 or a portion corresponding to the position and/or position 298 or a portion corresponding to the position of an amino acid sequence of SEQ ID NO: 4 each to another amino acid.

<7> A method for producing a plant with increased resistance to a 4-HPPD inhibitor, comprising the steps of:
(I) mutating, in an HSL protein of a plant cell, amino acids at position 204 or a portion corresponding to the position and/or position 298 or a portion corresponding to the position of an amino acid sequence of SEQ ID NO: 4 each to another amino acid; and
(II) regenerating a plant from the plant cell in which amino acid mutation is introduced in the step (I).

<8> A method for determining resistance of a plant to a 4-HPPD inhibitor, comprising: detecting a nucleotide which codes for amino acids at position 204 or a portion corresponding to the position and/or position 298 or a portion corresponding to the position of SEQ ID NO: 4 in an HSL gene of a test plant; and if the nucleotide codes for phenylalanine at position 204 or a portion corresponding to the position and/or for leucine at position 298 or a portion corresponding to the position, determining that the test plant has resistance to a 4-HPPD inhibitor.

<9> A method for breeding a plant having increased resistance to a 4-HPPD inhibitor, the method comprising the steps of:
(a) crossing a plant cultivar having resistance to a 4-HPPD inhibitor with any cultivar;
(b) determining resistance of an individual obtained by the mating in the step (a) to a 4-HPPD inhibitor by the method according to <8>; and
(c) selecting an individual determined to have resistance to the 4-HPPD inhibitor.

On the other hand, when tefuryltrione is used as a substrate for a 4-HPPD inhibitor, the catalytic activity to oxidize the agent can be reduced by substituting position 204 and/or position 298 of an HSL protein each with another amino acid (for example, substituting position 204 with phenylalanine and substituting position 298 with leucine) as shown in Examples described later.

Hence, the present invention also provides the following.

<10> A method for producing an HSL protein having reduced catalytic activity to oxidize tefuryltrione in a 2-oxoglutarate-dependent manner, the method comprising the step of:
mutating, in an HSL protein, amino acids at position 204 or a portion corresponding to the position and/or position 298 or a portion corresponding to the position of an amino acid sequence of SEQ ID NO: 4 each to another amino acid.

<11> A method for producing a plant having reduced resistance to benzobicyclon, benzobicyclon hydrolysate, or sulcotrione, the method comprising the steps of:
(I) mutating, in an HSL protein of a plant cell, amino acids at position 204 or a portion corresponding to the position and/or position 298 or a portion corresponding to the position of an amino acid sequence of SEQ ID NO: 4 each to another amino acid; and (II) regenerating a plant from the plant cell in which amino acid mutation is introduced in the step (I).

EXAMPLES

Although the present invention is described in more detail based on Examples below, the present invention is not limited to the following Examples.

The present inventors previously found that a gene (HIS1) rice has and a homologous gene (HSL1 gene) thereof contribute to resistance or susceptibility to a 4-HPPD inhibitor. The present inventors also found that a plant with increased resistance or susceptibility to a 4-HPPD inhibitor could be produced by utilizing these genes, and further found that genes having a high homology with the HIS1 gene of rice also exist in barley, sorghum, corn, and the like (PTL 1).

In addition, it has been surmised by the present inventors that the HIS1 and the OsHSL1 are 2-oxoglutarate-dependent dioxygenases (2OGDs), which are oxidases dependent on divalent iron ions and 2-oxoglutarate according to the amino acid motif search. The 2OGD is a protein containing non-heme iron ions, and is a soluble protein that locally exists in cytoplasms of plants. The 2OGD requires 2-oxoglutarate (2OG) and an oxygen molecule as co-substrates and requires a divalent iron ion as a cofactor. As described below, the 2OGD catalyzes the oxidation of the substrate ("R" in the following reaction formula) and this catalysis involves generation of succinic acid and carbon dioxide as a result of decarboxylation of 2OG.

$$R+2OG+O_2 \rightarrow RO+\text{succinic acid}+CO_2.$$

The catalytic center of each individual 2OGD takes a double-stranded β helix structure and has a preserved sequence motif, His-Xaa-Asp/Glu-(Xaa)n-His (SEQ ID NO: 23). This motif binds to a divalent iron ion to form a catalytic triad. The 2OGDs can be seen in from bacteria, animals, through plants, and have a wide variety of functions such as DNA modification, collagen synthesis, production of antibiotics, synthesis of plant hormones, and stress response. From gene information searching, it was predicted that there are 114 types from rice and 130 types from *Arabidopsis thaliana* (Kawai et al., Evolution and diversity of the 2-oxoglutarate-dependent dioxygenase superfamily in plants. The Plant Journal vol. 78 pp. 328-343, 2014).

Example 1

Evaluation on 4-HPPD Inhibitor Decomposition Activity of HIS1 Protein and Homologous Protein Thereof (OsHSL1 Protein)

In view of the above, the present inventors synthesized HIS1 and a homologous protein thereof by a cell-free protein synthesis method using a wheat germ extract described later and evaluated the herbicide (4-HPPD inhibitor) decomposition activity of these.

Note that in the beginning, the present inventors attempted to synthesize an HIS1 protein and the like using protein expression systems of *Escherichia coli* (the pET system, the pCold system, and the like), but not a cell-free protein synthesis method using a wheat germ extract. However, only insoluble HIS1 proteins were produced by any of the pET system, the pCold system, and the like, and the activity was not recovered even for solubilized proteins. For this reason, HIS1 proteins were synthesized by a cell-free protein synthesis system using a wheat germ extract to obtain soluble HIS1 proteins.

Then, the decomposition reaction of a 4-HPPD inhibitor was examined in the presence of divalent iron ions, 2-oxoglutarate, and molecular oxygen in a test tube by a method described later using the HIS1 protein prepared by this cell-free protein synthesis system.

Here, in commercially-available wheat germ extracts, dithiothreitol (DTT) is used as a reducing agent and a protein synthesizing reaction liquid also contains DTT. It was confirmed in advance by liquid chromatography that under the coexistence of divalent iron ions and ascorbic acid, which is a stabilizer for the divalent iron ions, DTT generated radical compounds and secondarily affected the enzyme reaction of HIS1 proteins. For this reason, in the present Example, an unreported protein synthesizing reaction system using Tris (2-carboxyethyl)phosphine (TCEP) as a reducing agent instead of DTT was newly constructed, with which the synthesis of HIS1 proteins and the like was conducted to examine the 4-HPPD inhibitor decomposition activity of these. The decomposition activity was analyzed on the reaction liquid of the protein and the 4-HPPD inhibitor using a high-performance liquid chromatography (mobile phase; 0.5% acetic acid water:acetonitrile=65:35, flow rate; 1 mL/min, feeding; isocratic, column; CAPCELL PAK ADME S5).

Figure 2:
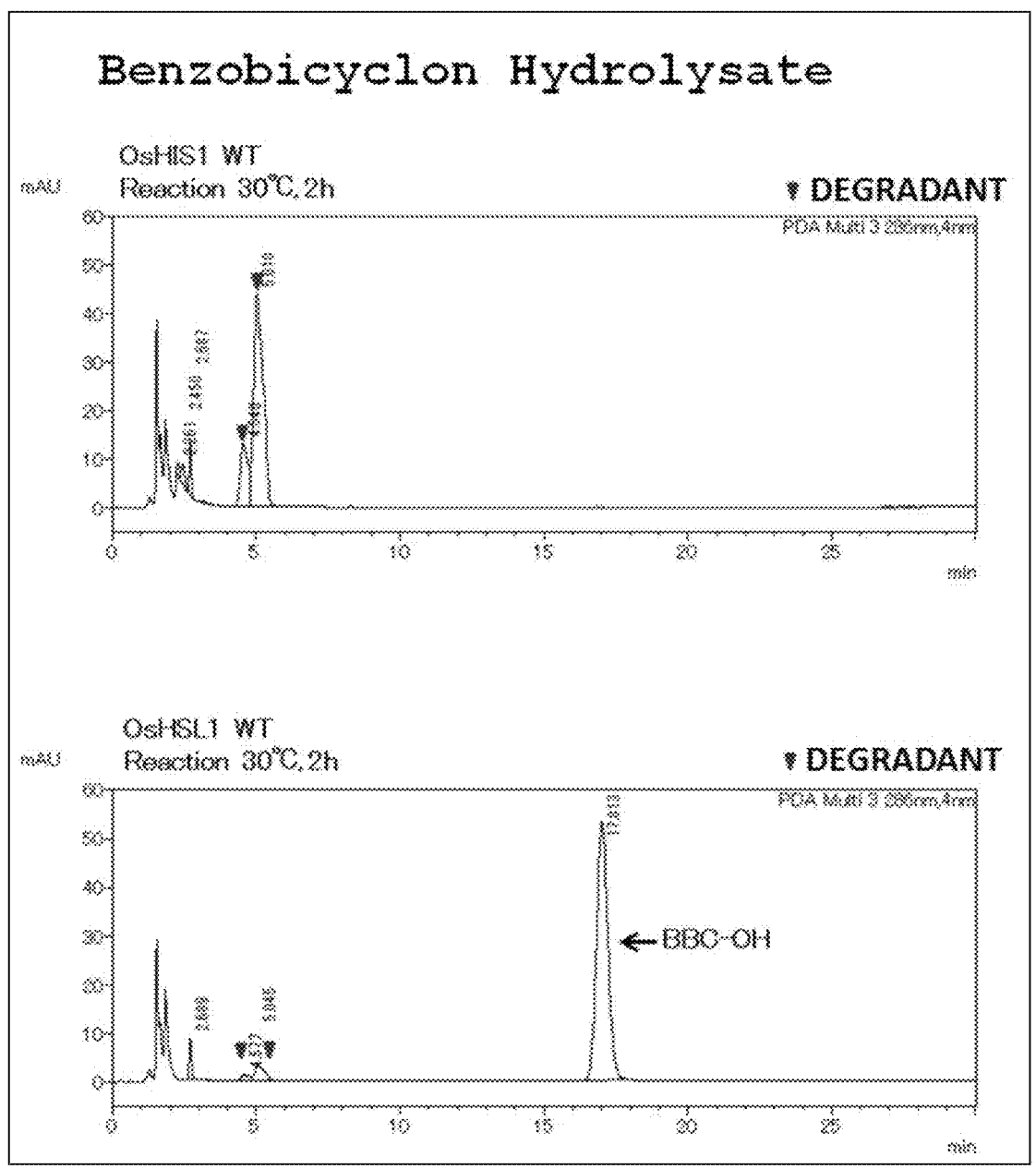
FIG. 2 is spectra showing results of analyzing benzobicyclon hydrolysate (BBC-OH) decomposition activities of an HIS1 protein and an OsHSL1 protein using high-performance liquid chromatography, where triangles each indicate a peak derived from a degradant of BBC-OH.
Figure 3:
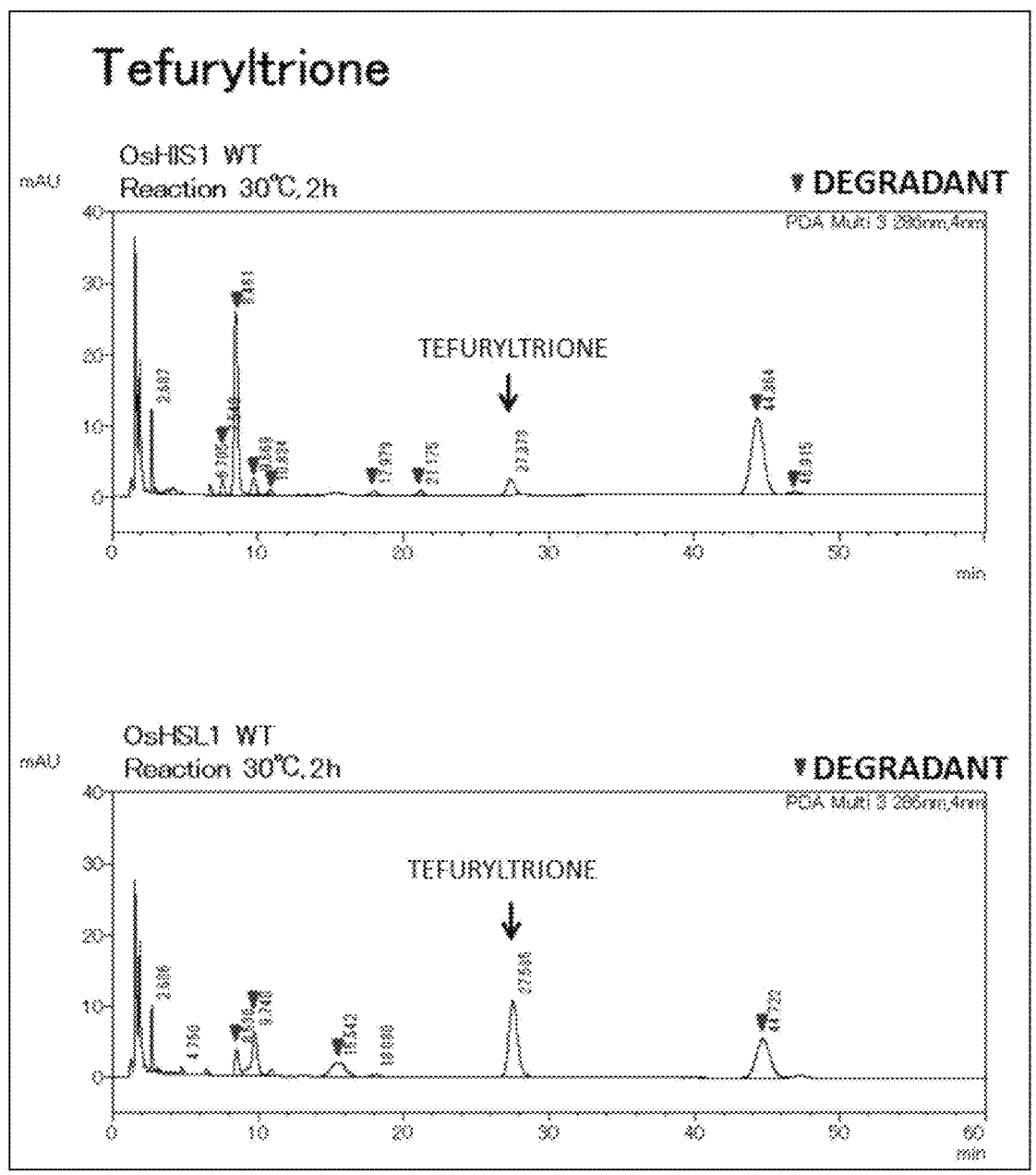
FIG. 3 is spectra showing results of analyzing tefuryltrione decomposition activities of the HIS1 protein and the OsHSL1 protein using high-performance liquid chromatography, where triangles each indicate a peak derived from a degradant of tefuryltrione.
Figure 4:
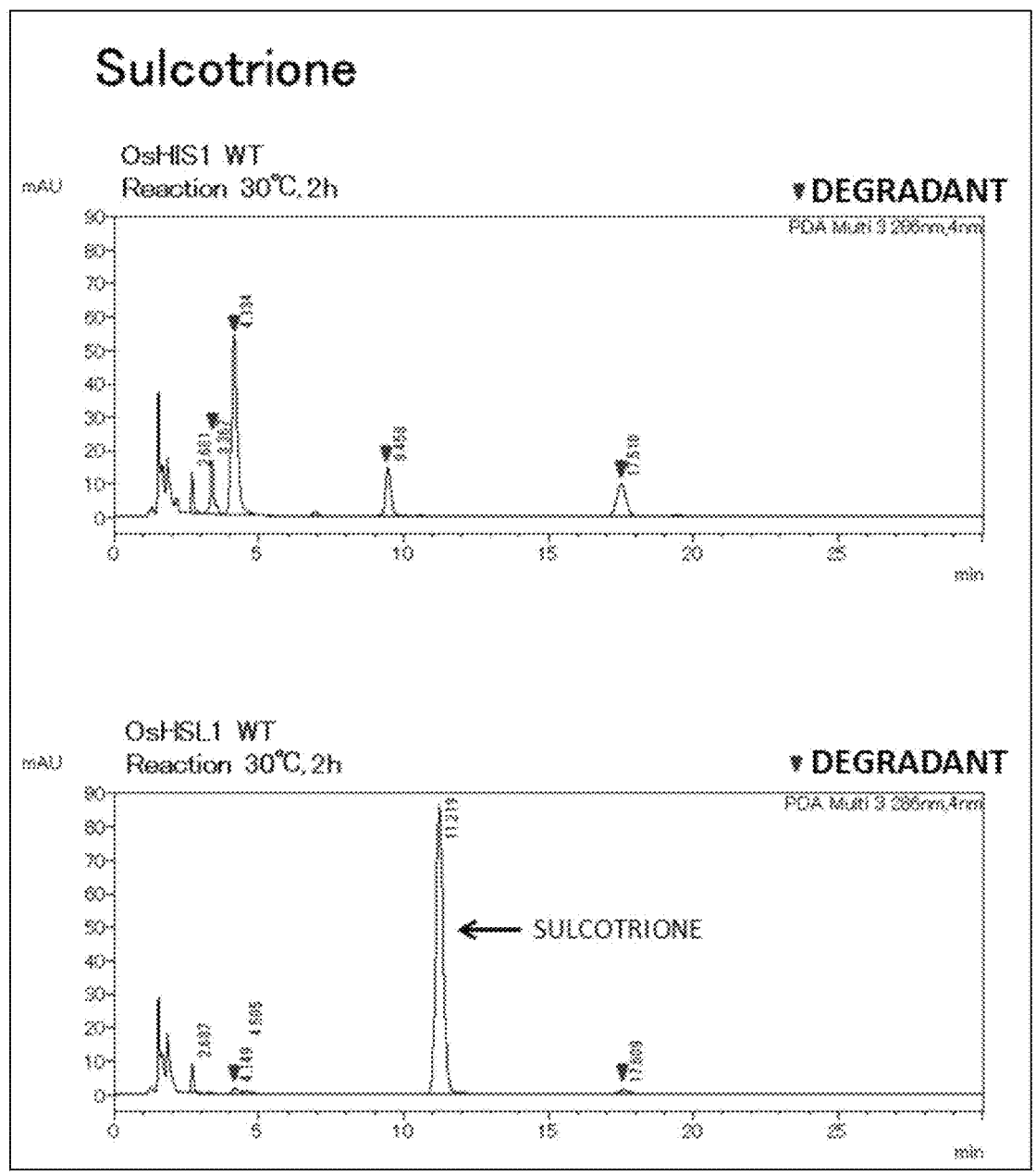
FIG. 4 is spectra showing results of analyzing sulcotrione decomposition activities of the HIS1 protein and the OsHSL1 protein using high-performance liquid chromatography, where triangles each indicate a peak derived from a degradant of sulcotrione.

As a result, as shown in FIGS. 2 to 4, it was confirmed that the HIS1 protein had a high decomposition activity to all of the 4-HPPD inhibitors, benzobicyclon hydrolysate (BBC-OH), tefuryltrione, and sulcotrione.

Note that benzobicyclon (BBC) is in the form of what is termed as a prodrug and is understood to suppress water solubility in soil and undergo hydroxylation around the root system of a plant and be absorbed mainly in the form of hydrolysate (BBC-OH) to exert its drug efficacy. Hence, since BBC-OH serves as an actual active ingredient in a plant, BBC-OH was used as an evaluation target for the present Example.

In addition, although not shown, as a result of examining the modification reaction of BBC-OH using the HIS1 protein, the reaction product was stably obtained. As a result, the modification of BBC-OH was confirmed only in the presence of divalent iron ions and 2-oxoglutarate. Moreover, as a result of analyzing the modification products of BBC-OH, tefuryltrione, and sulcotrione with the HIS1 protein by means of mass analysis, it was confirmed that all of the 4-HPPD inhibitors were each converted into a product with one oxygen atom added.

On the other hand, although the OsHSL1 protein has a high homology with the HIS1 protein at the amino acid sequence level, the decomposition activity to BBC-OH and sulcotrione was hardly observed as shown in FIGS. 2 and 3. Note that as shown in FIG. 4, it was revealed that the OsHSL1 protein had a decomposition activity to tefuryltrione, which was lower than that of the HIS1 protein, though.

Example 2

Estimation of Amino Acid Residue Involved in 4-HPPD Inhibitor Decomposition Activity in HIS1 Protein In view of this, based on this new finding, the present inventors surmised that a slight difference in amino acid sequence between the HIS1 protein and the OsHSL1 protein contributed to the decomposition activity of the 4-HPPD inhibitor. Then, the amino acid residue involved in the 4-HPPD inhibitor decomposition activity in the HIS1 protein was estimated by a method described below.

First, for the purpose of predicting the three-dimensional structure of the HIS1 protein, the present inventors attempted crystal structure analysis. However, the present inventors gave up because the purified protein was very unstable and easily insolubilized.

Instead, among oxidases dependent on divalent iron ions and 2-oxoglutarate, whose protein crystal structures have been revealed, anthocyanidin synthase, which is an enzyme of *Arabidopsis thaliana* and has the highest sequence similarity to HIS1, was used as a template to prepare the structure model of HIS1. The method was as described below.

First, the amino acid sequence of anthocyanidin synthase of *Arabidopsis thaliana* and the amino acid sequences of the rice HIS1 protein and the OsHSL1 protein were analyzed using software ClustalW (Thompson et al. CLUSTAL W: improving the sensitivity of progressive multiple sequence alignment through sequence weighting, position-specific gap penalties and weight matrix choice. Nucleic Acids Research vol. 22 pp. 4673-4680, 1994) to prepare an alignment. The homology in amino acid sequence with anthocyanidin synthase of *Arabidopsis thaliana* was 28.5% with HIS1 and 28.8% with OsHSL1. Subsequently, accession Number 1GP6 registered as the structure of the anthocyanidin synthase protein of *Arabidopsis thaliana* was selected from Protein Data Bank (rcsb.org/pdb/home/home.do), which is a public data bank of protein structures, based on information of the paper (Wilmouth et al. Structure and mechanism of anthocyanidin synthase from *Arabidopsis thaliana*. Structure vol. 10 pp. 93-103, 2002), which reported the protein three-dimensional crystal structure of anthocyanidin synthase of *Arabidopsis thaliana*. By using this 1GP6 as a template, the three-dimensional structure models of HIS1 and OsHSL1 were prepared utilizing software SWISS-MODEL (Biasini et al. SWISS-MODEL: modelling protein tertiary and quaternary structure using evolutionary information. Nucleic Acids Research vol. 42 (W1) pp. W252-W258, 2014.).

As a result, it was confirmed that an amino acid residue in which divalent iron ions are coordinated was stored in three types of proteins in common, and it was confirmed that once this residue was substituted with another amino acid, the enzyme activity of HIS1 disappeared.

Figure 5:
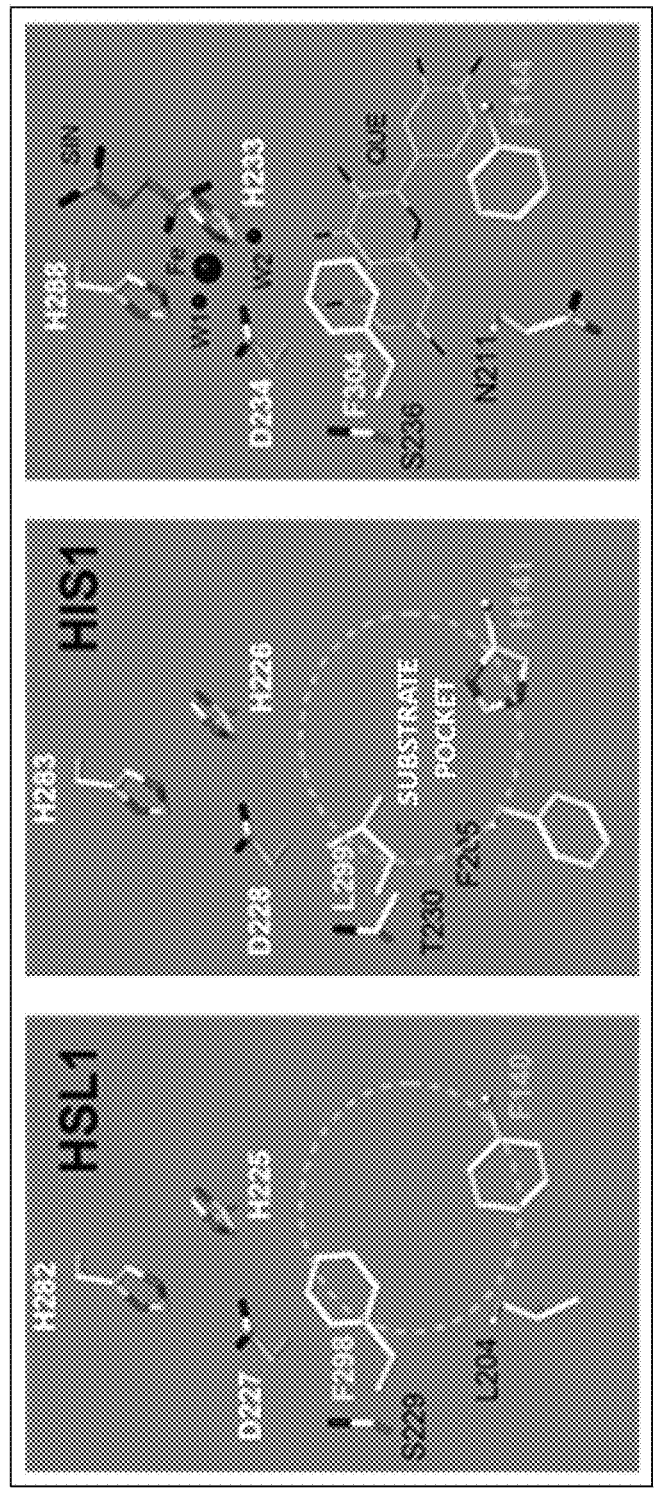
FIG. 5 is three-dimensional structure model diagrams showing amino acid residues predicted as substrate binding sites and amino acid residues predicted as surrounding substrate pockets in the HIS1 protein and the OsHSL1 protein, which are prepared using, as a template, anthocyanidin synthase of *Arabidopsis thaliana*, whose protein three-dimensional crystal structure has been interpreted (see a panel on the right side of FIG. 5).

Moreover, based on three-dimensional structure model (see FIG. 5) prepared using SWISS-MODEL regarding amino acid residues predicted as substrate binding sites and amino acid residues predicted as surrounding substrate pockets in the paper (Wilmouth et al. Structure and mechanism of anthocyanidin synthase from *Arabidopsis thaliana*. Structure vol. 10 pp. 93-103, 2002), which reported the three-dimensional crystal structure of anthocyanidin synthase protein, the present inventors compared mainly the secondary structures, that is, the α helix and β sheet structures to select amino acid residues that were different between HIS1 and OsHSL1.

Specifically, the present inventors found a possibility that among amino acid residues of the HIS1 protein which were predicted to be exposed to the substrate pocket, isoleucine at position 119 was substituted with valine at position 118 in OsHSL1, histidine at position 141 was substituted with phenylalanine at position 140 in OsHSL1, phenylalanine at position 205 was substituted with leucine at position 204 in OsHSL1, threonine at position 229 was substituted with serine at position 230 in OsHSL1, and leucine at position 299 was substituted with phenylalanine at position 298 in OsHSL1.

Example 3

Preparation of Mutants of OsHSL1 Proteins and Evaluation on 4-HPPD Inhibitor Decomposition Activities of these Mutants In view of this, to examine such possibility, amino acid residues in the OsHSL1 protein that are different from those of the HIS1 protein were substituted with those of HIS1 as appropriate and whether the enzyme activity of the HIS1 type was able to be added to the protein was analyzed by a method described below.

<Design of Mutagenesis Primers>

First, in order to substitute one of amino acid residues at positions 118, 140, 204, 229, and 298 of the OsHSL1 protein with that of the HIS1 protein in accordance with a site-directed mutagenesis method, mutagenesis primers used for this method were designed as illustrated below.

1) Amino-Acid Substitution of Valine Residue at Position 118 of OsHSL1 with Isoleucine Residue (HSL1 V118I)

Mutagenesis primers were designed so as to amino-acid substitute a valine residue at position 118 of OsHSL1 with an isoleucine residue. The base sequences of the mutagenesis primers are as described below. Note that lower-case letters indicate a mutated codon or an anticodon thereof.

```
V118IFW:
                                    (SEQ ID NO: 24)
5'-CGACGGCAAGAACTTCCAGattgAAGGGTATGGAACTGAC-3'

V118IRV:
                                    (SEQ ID NO: 25)
5'-GTCAGTTCCATACCCTTCaatCTGGAAGTTCTTGCCGTCG-3'
```

The att from position 20 to position 22 of the primer V118IFW (a codon corresponding to isoleucine, I) and the aat from position 19 to position 21 of the primer V118IRV (the complementary sequence of the codon att corresponding to isoleucine, I) were designed from GTG (valine, V) of a wild type OsHSL1. The valine residue at position 118 is substituted with an isoleucine residue by changing codon GTG to ATT.

2) Amino-Acid Substitution of Phenylalanine Residue at Position 140 of OsHSL1 to Histidine Residue (HSL1 F140H)

Mutagenesis primers were designed so as to amino-acid substitute a phenylalanine residue at position 140 of OsHSL1 to a histidine residue. The base sequences of the mutagenesis primers are as described below. Note that lower-case letters indicate a mutated codon or an anticodon thereof.

```
F140toH141FW:
                                    (SEQ ID NO: 26)
5'-GGTCTGATCGGCTGcatCTCAGAGTTGAACCC-3'

F140toH141RV:
                                    (SEQ ID NO: 27)
5'-GGGTTCAACTCTGAGatgCAGCCGATCAGACC-3'
```

The cat from position 15 to position 17 of the primer F140toH141FW (a codon corresponding to histidine, H) and the atg from position 16 to position 18 of the primer F140toH141RV (the complementary sequence of the codon cat corresponding to histidine, H) were designed from TTT (phenylalanine, F) of a wild type OsHSL1. The phenylalanine residue at position 140 is substituted with a histidine residue by changing codon TTT to CAT.

3) Amino-Acid Substitution of Leucine Residue at Position 204 of OsHSL1 with Phenylalanine Residue (HSL1 L204F)

Mutagenesis primers were designed so as to amino-acid substitute a leucine residue at position 204 of OsHSL1 with a phenylalanine residue. The base sequences of the mutagenesis primers are as described below. Note that lower-case letters indicate a mutated codon or an anticodon thereof.

```
L204toF205FW:
                                    (SEQ ID NO: 28)
5'-CAACAAAGCTCCTGCAtttgCAAGATTCAACTACTACCC-3'

L204toF205RV:
                                    (SEQ ID NO: 29)
5'-GGGTAGTAGTTGAATCTTGCaaaTGCAGGAGCTTTGTTG-3'
```

The ttt from position 17 to position 19 of the primer L204toF205FW (a codon corresponding to phenylalanine, F) and the aaa from position 21 to position 22 of the primer F140toH141RV (the complementary sequence of the codon ttt corresponding to phenylalanine, F) were designed from CTT (leucine, L) of the wild type OsHSL1. The leucine residue at position 204 is substituted with a phenylalanine residue by changing codon CTT to TTT.

4) Amino-Acid Substitution of Serine Residue at Position 229 of OsHSL1 with Threonine Residue (HSL1 S204T)

Mutagenesis primers were designed so as to amino-acid substitute a serine residue at position 229 of OsHSL1 with a threonine residue. The base sequences of the mutagenesis primers are as described below. Note that lower-case letters indicate a mutated codon or an anticodon thereof.

```
S229TFW:
                                    (SEQ ID NO: 30)
5'-CCTCACTCCGACGGCaccCTCTTTACGATTCTTC-3'

S229TRV:
                                    (SEQ ID NO: 31)
5'-GAAGAATCGTAAAGAGggtGCCGTCGGAGTGAGG-3'
```

The acc from position 16 to position 18 of the primer S229TFW (a codon corresponding to threonine, T) and the ggt from position 17 to position 19 of the primer S229TRV (the complementary sequence of the codon acc corresponding to threonine, T) were designed from TCC (serine, S) of the wild type OsHSL1. The serine residue at position 229 is substituted with a threonine residue by changing codon TCC to ACC.

5) Amino-Acid Substitution of Phenylalanine Residue at Position 298 of OsHSL1 with Leucine Residue (HSL1 F298L)

Mutagenesis primers were designed so as to amino-acid substitute a phenylalanine residue at position 298 of OsHSL1 with a leucine residue. The base sequences of the mutagenesis primers are as described below. Note that lower-case letters indicate a mutated codon or an anticodon thereof.

```
F298toL299FW:
                                    (SEQ ID NO: 32)
5'-GGATCTCACTGGCCATGttaTACAGTGTGAATGATGAG-3'

F298toL299RV:
                                    (SEQ ID NO: 33)
5'-CTCATCATTCACACTGTAtaaCATGGCCAGTGAGATCC-3'
```

The tta from position 18 to position 20 of the primer F298toL299FW (a codon corresponding to leucine, L) and taa from position 19 to position 21 of the primer F298toL299RV (the complementary sequence of the codon tta corresponding to leucine, L) were designed from TTT (phenylalanine, F) of the wild type OsHSL1. The phenylalanine residue at position 298 is substituted with a leucine residue by changing codon TTT to TTA.

<Preparation of Mutation-Introduced DNA>

Next, site-directed mutation is introduced into OsHSL1 proteins using QuikChange II Site-Directed Mutagenesis Kit (manufactured by Agilent) and primers designed by introduction of mutation as described above.

Specifically, a plasmid AK241948/pFLC1 in which cDNA coding for the OsHSL1 protein has been cloned (provided from Gene Bank of The National Institute of Agrobiological Sciences) was used as a template and inverse PCR was conducted using the above-described mutagenesis primer set to obtain a PCR product in which mutation was introduced in the cDNA.

To be specific, the composition of the PCR reaction was obtained by mixing 5 μl of buffer provided to the kit, 1 μl of dNTP mix provided to the kit, 1 μl (2.5 units) of pfu DNA polymerase provided to the kit, 1 μl (125 ng) of each of Fw and Rv primers, 1 μl (10 ng) of template plasmid DNA, and 40 μl of distilled water. Then, 50 μl of this reaction liquid was held at 95° C. for 30 seconds, and then reaction at 95° C. for 30 seconds, at 55° C. for one minute, and at 68° C. for 4.5 minutes was repeated for 16 cycles, followed by cooling down to 4° C. to prepare the PCR product, using a PCR reaction device (TaKaRa PCR Thermal Cycler TP350 manufactured by Takara Shuzo Co., Ltd.).

Subsequently, 1 μl (10 units) of DpnI provided to the kit was added to the amplified PCR product, followed by holding at 37° C. for 1 hour. With this reaction, the template plasmid in which mutation was not introduced was cut off.

After the completion of the reaction, 1 μl of the DpnI-treated PCR product was subjected to transformation of an *Escherichia coli* competent cell provided to the kit, and a mutation-introduced plasmid was prepared from the emerged drug-resistant colony.

Then, the mutation introduced OsHSL1 protein thus prepared was prepared by a cell-free protein synthesis method using a wheat germ extract (Kanno et al. Structure-Based in Vitro Engineering of the Anthranilate Synthase, a Metabolic Key Enzyme in the Plant Tryptophan Pathway. Plant Physiology vol. 138 pp. 2260-2268, 2005).

Note that after the reaction, the reaction liquid was subjected to SDS-polyacrylamide gel electrophoresis (SDS-PAGE). The electrophoresis was then followed by CBB staining to confirm that a protein having a desired molecular weight was synthesized.

<Multi Site-Directed Mutagenesis>

In addition, a plurality of amino acid residues at any of positions 118, 140, 204, 229, and 298 of the OsHSL1 protein were substituted with those of the HIS1 protein by the above same method, as shown below.

6) Amino-Acid Substitution of Phenylalanine Residue at Position 140 and Leucine Residue at Position 204 of OsHSL1 with Histidine Residue and Phenylalanine Residue, Respectively (HSL1 F140H L204F)

A plasmid pFLC1-HSL1 (L204F) obtained by amino-acid substituting a leucine residue at position 204 of OsHSL1 with a phenylalanine residue was used as a template, and mutagenesis was conducted such that a phenylalanine residue at position 140 was amino-acid substituted with a histidine residue using the above-described primers F140toH141FW and F140toH141RV.

7) Amino-Acid Substitution of Phenylalanine Residue at Position 140 and Phenylalanine Residue at Position 298 of OsHSL1 with Histidine Residue and Leucine Residue, Respectively (HSL1 F140H F298L)

A plasmid pFLC1-HSL1 (F298L) obtained by amino-acid substituting a phenylalanine residue at position 298 of OsHSL1 with a leucine residue was used as a template, and mutagenesis was conducted such that a phenylalanine residue at position 140 was amino-acid substituted with a histidine residue using the above-described primers F140toH141FW and F140toH141RV.

8) Amino-Acid Substitution of Leucine Residue at Position 204 and Phenylalanine Residue at Position 298 of OsHSL1 with Phenylalanine Residue and Leucine Residue, Respectively (HSL1 L204F F298L)

A plasmid pFLC1-HSL1 (F298L) obtained by amino-acid substituting a phenylalanine residue at position 298 with a leucine residue was used as a template, and mutagenesis was conducted such that a leucine residue at position 204 was amino-acid substituted with a phenylalanine residue using the above-described primers L204toF205FW and L204toF205RV.

9) Amino-Acid Substitution of Phenylalanine Residue at Position 140, Leucine Residue at 204, and Phenylalanine Residue at Position 298 of OsHSL1 with Histidine Residue, Phenylalanine Residue, and Leucine Residue, Respectively (HSL1 F140H L204F F298L)

A plasmid pFLC1-HSL1 (L204F F298L) obtained by amino-acid substituting a leucine residue at position 204 and a phenylalanine residue at position 298 of OsHSL1 with phenylalanine residue and leucine residue, respectively was used as a template, and mutagenesis was conducted such that a phenylalanine residue at position 140 was amino-acid substituted with a histidine residue using the above-described primers F140toH141FW and F140toH141RV. 10) Amino-Acid Substitution of Phenylalanine Residue at Position 140, Leucine Residue at Position 204, Serine Residue at Position 229, and Phenylalanine Residue at Position 298 of OsHSL1 with Histidine Residue, Phenylalanine Residue, Threonine Residue, and Leucine Residue, Respectively (HSL1 F140H L204F S229T F298L)

A plasmid pFLC1-HSL1 (F140H L204F F298L) obtained by amino-acid substituting a phenylalanine residue at position 140, a leucine residue at position 204, and a phenylalanine residue at position 298 of OsHSL1 with a histidine residue, a phenylalanine residue, and a leucine residue, respectively was used as a template, and mutagenesis was conducted such that a serine residue at position 229 was amino-acid substituted with a threonine residue using the above-described primers S229TFW and S229TRV. 11) Amino-Acid Substitution of Valine Residue at Position 118, Phenylalanine Residue at Position 140, Leucine Residue at Position 204, Serine Residue at Position 229, and Phenylalanine Residue at Position 298 with Isoleucine Residue, Histidine Residue, Phenylalanine Residue, Threonine Residue, and Leucine Residue, Respectively (HSL1 V118I F140H L204F S229T F298L)

A plasmid pFLC1-HSL1 (F140H L204F S229T F298L) obtained by amino-acid substituting a phenylalanine residue at position 140, a leucine residue at position 204, a serine residue at position 229, and a phenylalanine residue at position 298 with a histidine residue, a phenylalanine residue, a threonine residue, and a leucine residue, respectively was used as a template, and mutagenesis was conducted such that a valine residue at position 118 was amino-acid substituted with an isoleucine residue using the above-described primers V118IFW and V118IRV.

Example 4

Preparation of Mutants of HSL1 Proteins (Except for OsHSL1 Protein) and Evaluation on 4-HPPD Inhibitor Decomposition Activity of these Mutants In addition, in order to evaluate the 4-HPPD inhibitor decomposition activity of a rice-derived HSL protein group except for OsHSL1 and an HSL protein group that exhibits a homology with HIS1, regarding cultivars other than rice, these proteins were prepared in accordance with a method described below.

(Preparation of Cell-Free Expression Constructs of HSL Proteins)

The preparation of artificially synthesized DNAs was requested to Eurofins Genomics, where in the artificially synthesized DNAs, the SpeI recognition sequence and the SalI recognition sequence were added to upstream and downstream of translated regions of HIS1 homologous genes (HSL genes) derived from rice (*Oryza sativa*), wheat (Triticumaestivum), barley (*Hordeum vulgare*), sorghum (Sorghum biocolor), and corn (*Zea mays*) except for HIS1 and OsHSL1 (regarding the rice-derived OsHSL2 gene, the nucleotide sequence of SEQ ID NO: 5; regarding the barley-derived HvHSL1 gene, the nucleotide sequence of SEQ ID NO: 7; regarding the barley-derived HvHSL2 gene, the nucleotide sequence of SEQ ID NO: 9; regarding the barley-derived HvHSL3 gene, the nucleotide sequence of SEQ ID NO: 11; regarding the wheat-derived TaHSL1 gene, the nucleotide sequence of SEQ ID NO: 13; regarding the wheat-derived TaHSL2 gene, the nucleotide sequence of SEQ ID NO: 15; regarding the corn-derived ZmHSL1, the nucleotide sequence of SEQ ID NO: 17; regarding the corn-derived ZmHSL2, the nucleotide sequence of SEQ ID NO: 19; regarding the sorghum-derived SbHSL1, the nucleotide sequence of SEQ ID NO: 21). The artificially synthesized DNAs obtained were processed with the restriction enzymes SpeI and SalI to isolate target genes. The genes obtained were introduced into plasmid vectors pYT08 for cell-free translation that were also processed with the same restriction enzyme, so that cell-free expression constructs pYT08-OsHSL2, TaHSL1, TaHSL2, HvHSL1, HvHSL2, HvHSL3, SbHSL1, ZmHSL1, and ZmHSL2 were prepared.

<Introduction of Mutation into ZmHSL2 and SbHSL1>

Moreover, regarding rice-derived OsHSL2, the corn-derived ZmHSL2, and the sorghum-derived SbHSL1, mutation-introduced proteins into which an HIS1-type amino acid residue was introduced were prepared and their 4-HPPD inhibitor-modifying activities were examined.

To be specific, as described above, it was surmised from comparison between HIS1 and OsHSL1 that histidine at position 141 and leucine at position 299 of HIS1 were involved in the BBC-OH-modifying activity. In ZmHSL2 and SbHSL1, an amino acid corresponding to leucine at position 299 of HIS1 is the same as that of HIS1 and the other (corresponding to histidine at position 141 of HIS1) has a residue different from that of HIS1. In view of this, for ZmHSL2 and SbHSL1, histidine was mutated to the residue corresponding to position 141 of HIS1 and the activity thereof was examined. On the other hand, in OsHSL2, an amino acid corresponding to leucine at position 140 of HIS1 is the same as that of HIS1 and an amino acid corresponding to leucine at position 299 of HIS1 has a residue different from that of HIS1. In view of this, for OsHSL2, leucine was mutated to the residue corresponding to position 299 of HIS1 and the activity thereof was examined.

(Mutagenesis Primer)

1) Amino-Acid Substitution of Phenylalanine Residue at Position 301 of OsHSL2 with Leucine Residue (HSL2 F301L)

Like Example 3 described above, mutagenesis primers were designed so as to amino-acid substitute a phenylalanine residue at position 301 of OsHSL2 with a leucine residue. The base sequences of the mutagenesis primers are as described below. Note that lower-case letters indicate a mutated codon or an anticodon thereof.

```
Os2_F301L_Fw:
                                    (SEQ ID NO: 34)
5'-ttgTATGCGGTCGATGGGGAGAAG-3'

Os2_F301L_Rv:
                                    (SEQ ID NO: 35)
5'-CATGGCTACCGACATCCTCTCAC-3'
```

The ttg from position 1 to position 3 of the primer Os2_F301L_Fw (a codon corresponding to leucine, L) was designed from TIC (phenylalanine, F) of the wild type OsHSL2. The phenylalanine residue at position 301 is substituted with a leucine residue by changing codon TTC to TTG.

2) Amino-Acid Substitution of Glutamine Residue at Position 140 of ZmHSL2 with Histidine Residue (ZmHSL2 Q140H)

Like Example 3 described above, mutagenesis primers were designed so as to amino-acid substitute a glutamine residue at position 140 of ZmHSL2 with a histidine residue. The base sequences of the mutagenesis primers are as described below. Note that lower-case letters indicate a mutated codon.

```
Zm2_Q140H_Fw:
                                    (SEQ ID NO: 36)
5'-catCTAAAGGTCGAGCCAGAGG-3'

Zm2_Q140H_Rv:
                                    (SEQ ID NO: 37)
5'-CAACCTGTCATTCCAGTCCAAGATG-3'
```

3) Amino-Acid Substitution of Glutamine Residue at Position 140 of SbHSL1 with Histidine Residue (SbHSL1 Q140H)

Like Example 3 described above, mutagenesis primers were designed so as to amino-acid substitute a glutamine residue at position 140 of SbHSL1 with a histidine residue. The base sequences of the mutagenesis primers are as described below. Note that lower-case letters indicate a mutated codon.

```
Sb1_Q140H_Fw:
                                    (SEQ ID NO: 38)
5'-catCTGAAGGTTGAGCCGGAGG-3'

Sb1_Q140H_Rv:
                                    (SEQ ID NO: 39)
5'-GAGTCTGTCGCTCCAGTCGAGAATG-3'
```

4) Amino-Acid Substitution of Tyrosine Residue at Position 205 of ZmHSL2 with Phenylalanine Residue (ZmHSL2 Y205F)

Like Example 3 described above, mutagenesis primers were designed so as to amino-acid substitute a tyrosine residue at position 205 of ZmHSL2 with a phenylalanine residue. The base sequences of the mutagenesis primers are as described below. Note that lower-case letters indicate a mutated codon.

Zm2_Y205F_Fw:
(SEQ ID NO: 40)
5'-tttgCCCGCTTCAACTACTAC-3'

Zm2_Y205F_Rv:
(SEQ ID NO: 41)
5'-GGCTTGGGGACTTGCTC-3'

(Preparation of Mutation-Introduced DNA)

Site-directed mutation was introduced through inverse PCR using primers designed with metagenesis. The pYT08-ZmHSL2 vector prepared as described above was used as a template and inverse PCR was conducted using the above-described mutagenesis primer set to obtain a PCR product in which mutation was introduced.

The composition of the PCR reaction contained 1×PCR buffer for KOD plus neo (manufactured by Toyobo Co., Ltd.), 0.2 mM of dNTPs, 1.5 mM of MgSO4, 0.02 units/μl of KOD plus neo (manufactured by Toyobo Co., Ltd.), 0.3 μM of the Fw and Rv primers, and 1 ng of the template DNA, which were held at 94° C. for 2 minutes, and then reaction at 98° C. for 10 seconds and at 68° C. for 2 minutes and 15 seconds was repeated for 5 cycles, followed by cooling down to 4° C. to prepare the PCR product, using a PCR reaction device (TaKaRa PCR Thermal Cycler TP350 manufactured by Takara Shuzo Co., Ltd.).

Then, 1 μl of DpnI (20 units/μl) (manufactured by Bio rab Laboratories, Inc.) was added to 20 μl of the amplified PCR product, followed by holding at 37° C. for 1 hour. With this reaction, the template plasmid in which mutation was not introduced was cut off.

After the completion of the reaction, 1 μl of the DpnI-treated PCR product was mixed with 0.5 μl of T4 polynucleotide kinase (10 units/μl), 2.5 μl of Ligation high (manufactured by Toyobo Co., Ltd.), and 3.5 μl of MilliQ, followed by holding at 16° C. for 1 hour. The PCR product in which mutation was introduced through the above reactions was self-ligated and circularized to construct a mutation-introduced plasmid.

(Protein Synthesis Through Wheat Germ Cell-Free System)

First, synthesis of DNAs for transfer template was conducted through PCR in accordance with the following procedures. The plasmids prepared were used to prepare for templates of in vitro transfer reaction through PCR using the pYT08_Fw2 primer: 5'-CGCATCAGGCAGGAAATATT-TAGGTGAC-3' (SEQ ID NO: 42) and the pYT08_Rv primer: 5'-GGAGAAAGGCGGACAGGTATCCGGTAAG-3' (SEQ ID NO: 43). The composition of the PCR reaction contained 1×ExTaq buffer, 2 mM of dNTPs, 0.025 units/μl of KOD plus neo (manufactured by Toyobo Co., Ltd.), 0.2 μM of Fw and Rv primers, and 1 ng of template DNA, which were held at 94° C. for 2 minutes, and then reaction at 98° C. for 10 seconds and at 68° C. for 2 minutes and 15 seconds was repeated for 5 cycles, followed by cooling down to 4° C., using a PCR reaction device (TaKaRa PCR Thermal Cycler TP350 manufactured by Takara Shuzo Co., Ltd.).

Next, with the obtained PCR product as a template, transfer reaction was conducted to synthesize mRNA. The mRNA was synthesized (transferred) using the obtained PCR product directly as a template. Specifically, the PCR product was added in an amount of 1/10 to a transfer reaction liquid [80 mM of HEPES-KOH (pH 7.8), 16 mM of Mg (OAc)$_2$, 10 mM of spermidine, 10 mM of DTT, 3 mM of NTP, 1 unit/μl of RNasin RNase inhibitor (manufactured by Promega Corporation), 1 unit/μl of SP6 RNA polymerase (manufactured by Promega Corporation)]. After reaction at 37° C. for 2 hours, ethanol precipitation and 70% ethanol washing were conducted, followed by dissolving into an appropriate amount of sterile water. The absorbance at 260 nm was measured to calculate the amount of RNA.

Subsequently, with the obtained mRNA as a template, protein synthesis was conducted by the dialysis method using a wheat germ extract. Specifically, the above-described mRNA (about 30-35 μg) was added to a dialysis cup containing 50 μl of a wheat germ cell-free protein synthesis liquid. Then, the dialysis cup was immersed into a 24-well plate containing 650 μl of a substrate solution in each well, followed by incubation at 16° C. for 48 hours. After the reaction, 0.5 μl of the reaction liquid was mixed with 10 μl of a 1×loading buffer and thermal denaturation (95° C., 5 min) was conducted, followed by SDS-PAGE using a 12% polyacrylamide gel. The electrophoresis was then followed by CBB staining to confirm that a protein having a desired molecular weight was synthesized.

Then, the amounts of the synthesized proteins obtained in Examples 1 to 4 as described above were estimated as described below, followed by the analysis on the 4-HPPD inhibitor decomposition activities.

(Estimation of Amount of Synthesized Protein Using Liquid Scintillation Counter)

The amount of each synthesized protein was estimated by adding [$^{14}$C]-Leucine to the synthesis reaction liquid to conduct cell-free protein synthesis and measuring the $^{14}$C count taken in the synthesized protein. Specifically, the mRNA and [$^{14}$C]-Leucine (manufactured by PerkinElmer Inc.) were added to inside and outside liquids in an amount of 1/100 in a dialysis cup containing 50 μl of a wheat germ cell-free protein synthesis liquid, and the dialysis cup was immersed into a 24-well plate containing 650 μl of a substrate solution in each well, followed by incubation at 16° C. for 48 hours. After the completion of the reaction, 5 μl of the reaction liquid was spotted on a paper filter 3MM CHR (manufactured by GE Healthcare), and TCA precipitation and ethanol washing were conducted, followed by immersion into Clear-Sol (manufactured by Nacalai Tesque, Inc.). Then, $^{14}$C count taken in the synthesized protein was measured by using a liquid scintillation counter and the total $^{14}$C count contained in the synthesized protein was calculated (A). Moreover, the total $^{14}$C contained in the reaction liquid was spotted on a paper filter and the $^{14}$C count was measured in the same manner (B), the ratio of [$^{14}$C]Leu taken in the synthesized protein (B/A) was calculated from these values (C). Then, the ratio of specific one residue taken in the amino acid sequence of the synthesized protein (C/D) was calculated by dividing the ratio of [$^{14}$C]Leu by the number of Leus (D) contained in the amino acid sequence of the protein (E). Then, the amount of the synthesized protein (F×E×G) was calculated by multiplying this by the amino acid content (F) in the reaction liquid and the molecular weight (G) of the synthesized protein.

(Enzyme Preparation)

Cell-free protein synthesis was conducted without adding [$^{14}$C]-Leucine under the same conditions as those in the estimation of the synthesized amount to estimate the protein concentration of this translation reaction liquid from the above-described estimation. Then, 100 μl of the translation reaction liquid was subjected to buffer exchange to a basic translation buffer (30 mM HEPES-KOH (pH=7.8), 100 mM KOAc) by using the illustra MicroSpin G-25 column (manufactured by GE Healthcare). The amounts of the solution before and after the buffer exchange were measured and the estimated protein concentration was corrected.

(Enzyme Analyzing Method)

An enzyme reaction liquid was prepared by mixing 250 mM of HEPES-KOH (pH 7.0) with a mixture liquid, which contained 0.25 mM of FeCl2, 1.5 mM of ascorbic acid, 1.5 mM of 2-oxoglutarate, and 0.75 mM of a substrate, and a translation reaction liquid, which contained a synthesized enzyme protein, in a proportion of 40% and 60%, respectively. After incubation at 30° C. for 3 hours, 100% methanol in the same amount as the enzyme reaction liquid was added and sufficiently mixed, followed by being left to stand for 5 minutes on ice. This was subjected to centrifuge separation (20, 400 g, 20 minutes, 4° C.) and the supernatant was passed through Cosmonice Filter W (0.45 µm) (manufactured by Nacalai Tesque, Inc.) to obtain a sample for high-performance liquid chromatography. The analysis on the substrate and the product before and after the enzyme reaction was conducted by loading a column_Pro C18 (150×4.6 mm I.D.) (manufactured by YMC Co., Ltd.) on a high-performance liquid chromatography device_ELITE LaChrom L-2000 series (manufactured by Hitachi, Ltd.). Elution was conducted at a flow speed of 1 mL/min and a column temperature of 40° C. under solvent conditions of acetonitrile:water (1% acetic acid)=55:45 or 50:50 (BBC-OH), acetonitrile:water (1% acetic acid)=45:55 (Sulcotrione), acetonitrile:water (1% acetic acid)=45:55 (Mesotrione), acetonitrile:water (1% acetic acid)=55:45 or 50:50 (tefryltrone), and acetonitrile:water (1% acetic acid)=55:45 or 50:50 (Tembotrione), respectively, and the compound was detected at an ultraviolet wavelength of 286 nm.

Figure 6:
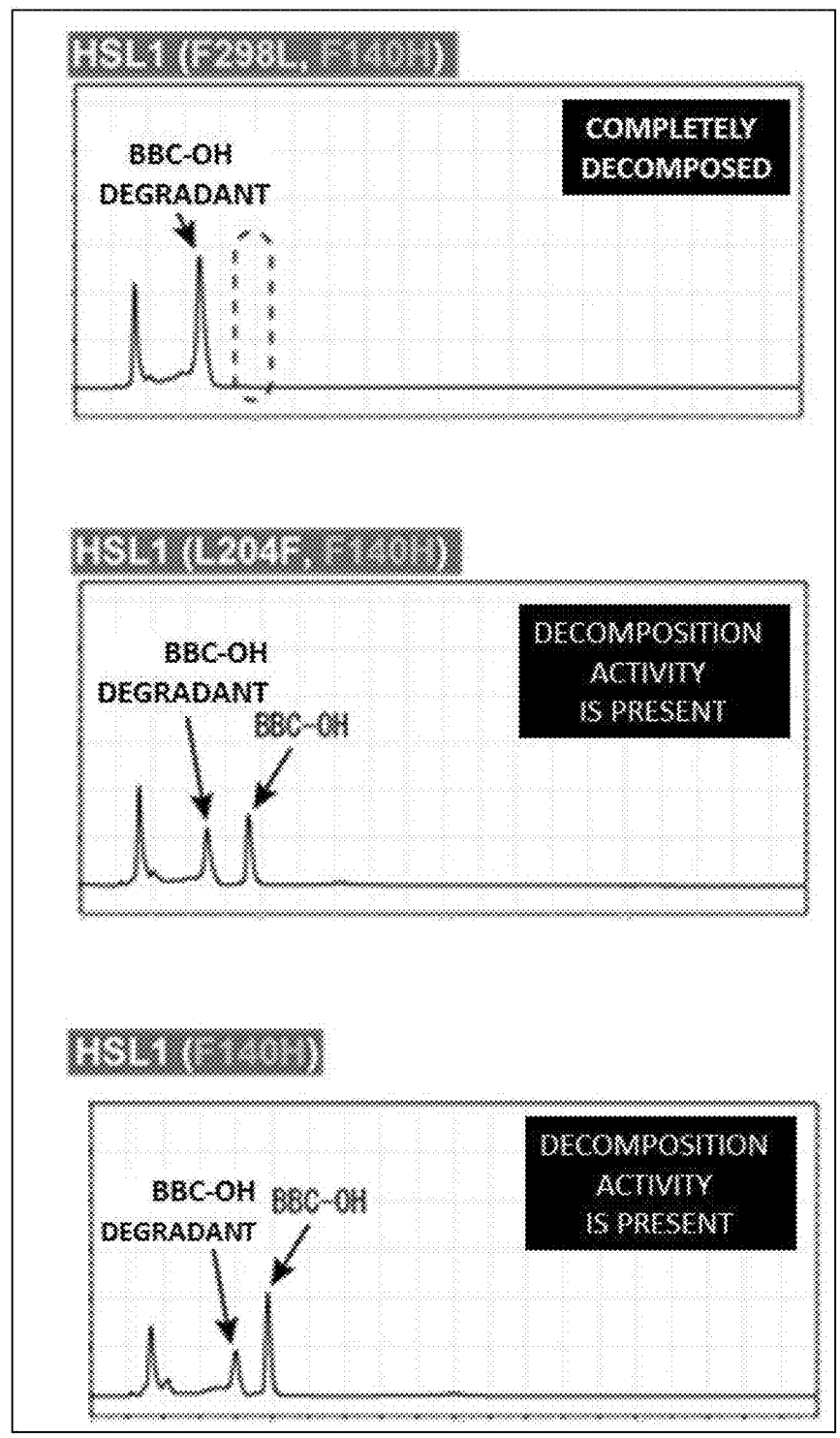
FIG. 6 is spectra showing results of analyzing BBC-OH decomposition activities of OsHSL1 protein mutants (a two-site mutant of F140H and F298L, a two-site mutant of F140H and L204F, and a single-site mutant of F140H) using high-performance liquid chromatography.
Figure 7:
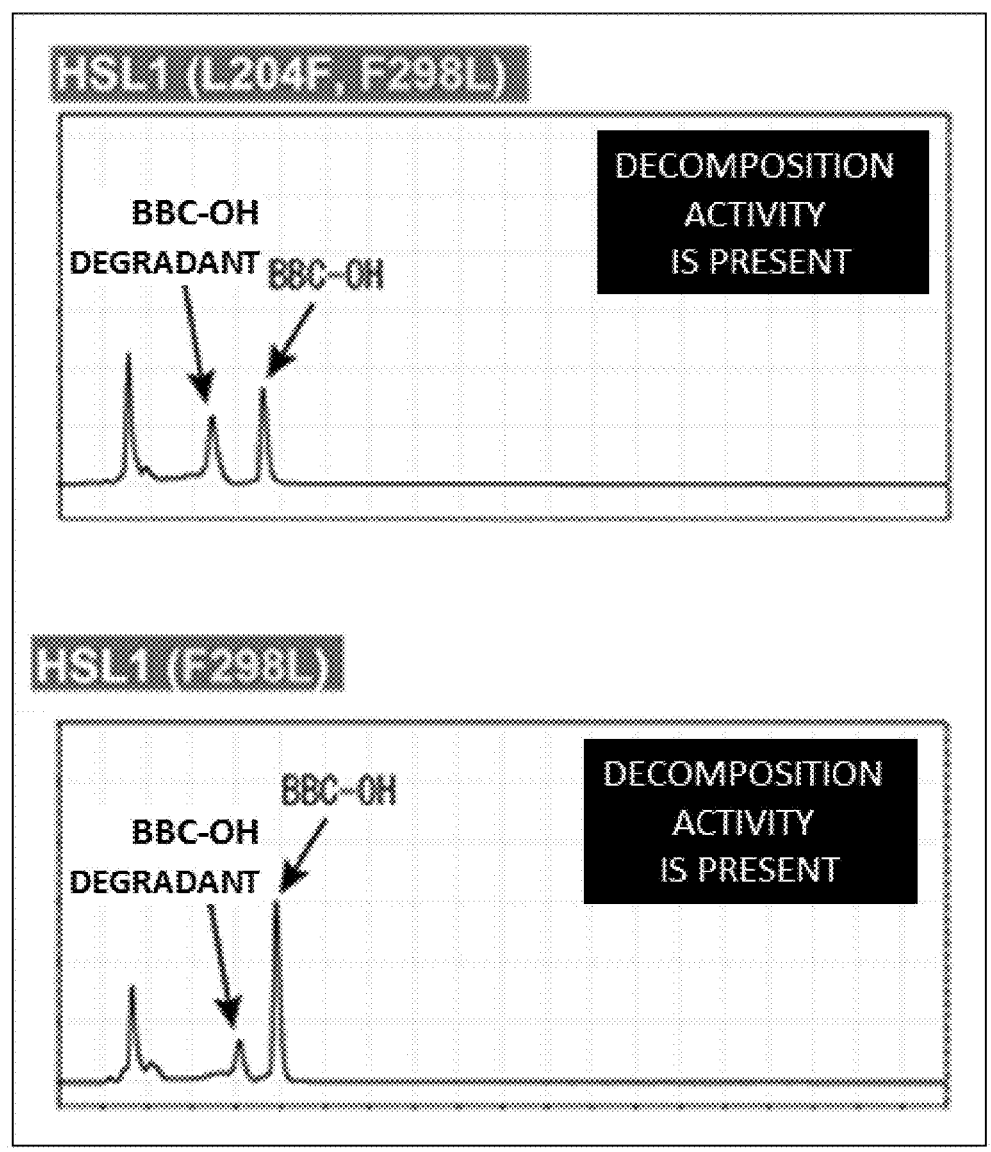
FIG. 7 is spectra showing results of analyzing BBC-OH decomposition activities of OsHSL1 protein mutants (a two-site mutant of L204F and F298L and a single-site mutant of F298L) using high-performance liquid chromatography.
Figure 8:
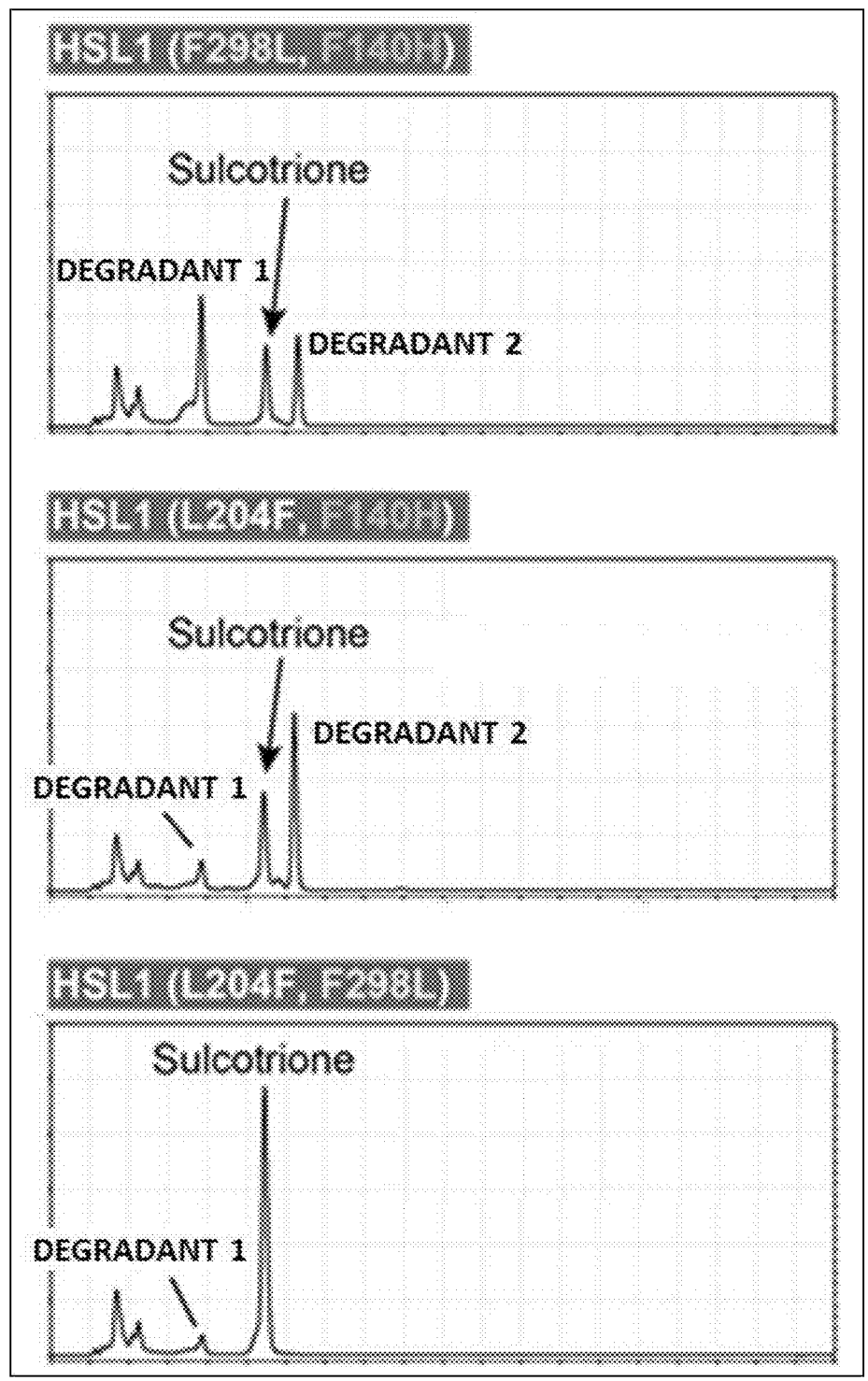
FIG. 8 is spectra showing results of analyzing sulcotrione decomposition activities of OsHSL1 protein mutants (the two-site mutant of F140H and F298L, the two-site mutant of F140H and L204F, and the two-site mutant of L204F and F298L) using high-performance liquid chromatography.
Figure 9:
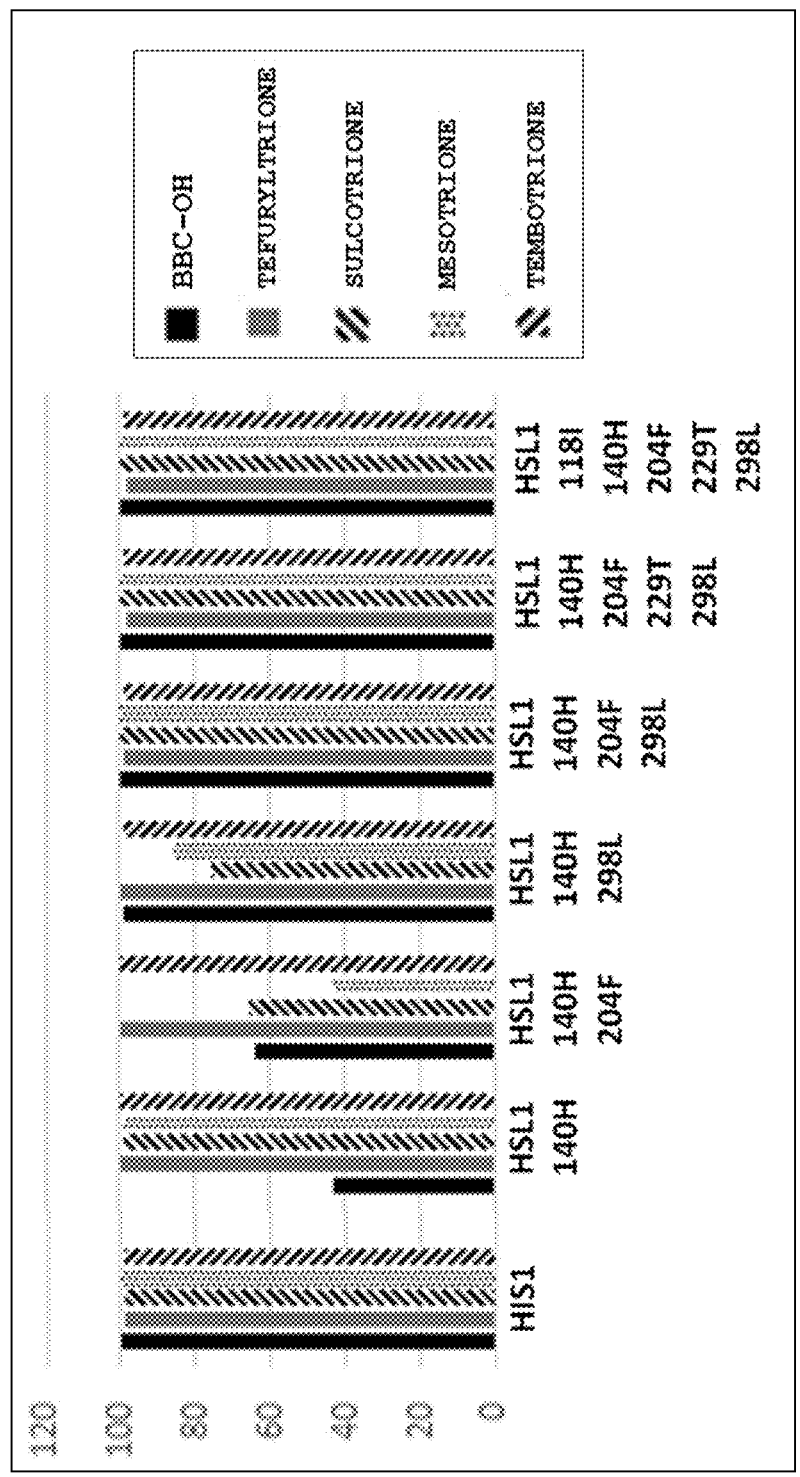
FIG. 9 is a graph showing results of analyzing decomposition activities of various mutants of the HIS1 protein and the OsHSL1 protein against various 4-HPPD inhibitors, using high-performance liquid chromatography, where "HIS1" indicates various 4-HPPD inhibitors decomposition activities of the HIS1 protein, "HSL1140H" indicates those of the single-site mutant (F140H) of the OsHSL1 protein, "HSL1 140H 204F" indicates those of a two-site mutant (F140H and L204F) of the OsHSL1 protein, "HSL1 140H 298L" indicates those of the two-site mutant (F140H and F298L) of the OsHSL1 protein, "HSL1 140H 204F 298L" indicates those of a three-site mutant (F140H, L204F, and F298L) of the OsHSL1 protein, "HSL1 140H 204F 229T 298L" indicates those of a four-site mutant (F140H, L204F, S229T, and F298L) of the OsHSL1 protein, and "HSL1 118I 140H 204F 229T 298L" indicates those of a five-site mutant (V118I, F140H, L204F, S229T, and F298L) of the OsHSL1 protein, and where the vertical axis indicates a relative value when the values of the 4-HPPD inhibitor decomposition activities of the HIS1 protein are each set to 100.

By the above-described method, the HIS1 proteins and their homologous proteins (HSL proteins) as well as mutation-introduced products of these were evaluated in terms of the 4-HPPD inhibitor decomposition activity, and the results of the evaluation are shown in FIGS. 12 to 17. In addition, representative results are shown in FIGS. 6 to 8. Moreover, a graph in which the results of the mutation-introduced product of the HSL1 proteins were compiled is shown in FIG. 9.

Note that the 5-point scale of the decomposition activity in each of FIGS. 12 to 17 is based on a relative value of the degree of decrease in a substrate-derived peak area detected by HPLC where the degree of decrease in the HIS1 protein was designated by 5. Moreover, the amino acid portions shown in FIGS. 12, 16 and 17 indicate positions in the OsHSL1 protein of SEQ ID NO: 4; in FIGS. 13, 14, and 15, the portions are read as amino acids corresponding to these positions. In addition, Table 7 shows amino acids at the portions of the OsHSL1 protein, amino acids corresponding to the aforementioned amino acids in the other proteins, and positions of the corresponding amino acids of each of the other proteins.

<Introduction of Mutation in OsHSL1 Protein>

Regarding the OsHSL1 protein, in the case where the substrate was BBC-OH, only very weak decomposition activity was observed in the wild type, as shown in FIG. 12 and FIG. 2. However, as shown in FIG. 12, FIG. 6, and FIG. 9, introduction of the F140H mutation significantly increased the activities. Moreover, it was revealed that addition of the L204F mutation or addition of the F298L mutation further improved the decomposition activities of BBC-OH.

Moreover, as shown in FIG. 12, it was revealed that substitution of that portion with lysine, which is a basic amino acid like histidine, also improved the BBC-OH decomposition activity of the OsHSL1 protein, which was less effective than the introduction of the F140H mutation, though.

In addition, as shown in FIG. 12 and FIG. 7, it was revealed that introduction of the F298L mutation also improved the BBC-OH decomposition activity of the OsHSL1 protein, which was less effective than the introduction of the F140H mutation, though. Moreover, it was revealed that addition of the L204F mutation further improved the activity.

In addition, regarding the OsHSL1 protein, in the case where the substrate was tefuryltrione, as shown in FIG. 16 and FIG. 3, it was observed that even the wild type had the decomposition activity, which was less effective than that of the HIS1 protein, though. Moreover, as shown in FIG. 16, it was revealed that introduction of the F140H mutation improved the activity to as high a level as that of the HIS1 protein. On the other hand, in the introduction of the F298L mutation, it was revealed that although the tefuryltrione decomposition activity of the OsHSL1 protein decreased, addition of both mutations (F140H and F298L) allowed for as high a tefuryltrione decomposition activity as that of the HIS1 protein again.

Furthermore, as shown in FIG. 16, it was revealed that substitution of that portion with lysine, which is a basic amino acid like histidine, also improved the tefuryltrione decomposition activity of the OsHSL1 protein, which was less effective than the introduction of the F140H mutation, though.

In addition, regarding the OsHSL1 protein, in the case where the substrate was sulcotrione, only very weak decomposition activity was observed in the wild type, as shown in FIG. 17 and FIG. 4. However, as shown in FIG. 17 and FIG. 9, it was revealed that introduction of the F140H mutation improved the activity to as high a level as that of the HIS1 protein. On the other hand, as shown in FIG. 8 and FIG. 9,

TABLE 7

| | Position 118 | Position 140 | Position 204 | Position 229 | Position 298 |
|---|---|---|---|---|---|
| OsHSL1 (SEQ NO: 4) | VALINE | PHENYLALANINE | LEUCINE | SERINE | PHENYLALANINE |
| HIS1 (SEQ NO: 2) | Position 119 ISOLEUCINE | Position 141 HISTIDINE | Position 205 PHENYLALANINE | Position 230 THREONINE | Position 299 LEUCINE |
| OsHSL2 (SEQ NO: 6) | Position 119 ISOLEUCINE | Position 141 HISTIDINE | Position 206 THREONINE | Position 231 CYSTEINE | Position 301 PHENYLALANINE |
| ZmHSL2 (SEQ NO: 20) | Position 118 LEUCINE | Position 140 GLUTAMINE | Position 205 TYROSINE | Position 230 PROLINE | Position 299 LEUCINE |
| SbHSL1 (SEQ NO: 22) | Position 118 LEUCINE | Position 140 GLUTAMINE | Position 205 TYROSINE | Position 230 PROLINE | Position 299 LEUCINE | it was also revealed that addition of the L204F mutation or addition of the F298L mutation decreased the sulcotrione decomposition activity.

In addition, as shown in FIG. 17, it was revealed that even when the F140H mutation was not introduced, introduction of the L204F mutation and the F298L mutation improved the sulcotrione decomposition activity. Moreover, although not shown in the figures, regarding mesotrione and tembotrione as well, it was revealed that this 2-site mutagenesis improved the decomposition activity.

Moreover, as shown in FIG. 17, substitution of that portion with arginine, which is a basic amino acid like histidine, also improved the sulcotrione decomposition activity of the OsHSL1 protein, which was less effective than the introduction of the F140H mutation, though.

In addition, regarding the OsHSL1 protein, in the case where the substrate was mesotrione or tembotrione, although not shown in the figures, only very weak decomposition activity was observed in the wild type. However, it was revealed that introduction of the F140H mutation improved the activities in both cases to as high a level as that of the HIS1 protein.

<Introduction of Mutation in OsHSL2 Protein>

Regarding the OsHSL2 protein, in the case where the substrate was BBC-OH, only very weak decomposition activity was observed in the wild type, as shown in FIG. 13. However, it was revealed that introduction of the F298L mutation was improved the BBC-OH decomposition activity of the OsHSL2 protein.

<Introduction of Mutation in ZmHSL2 Protein>

Regarding the ZmHSL2 protein, in the case where the substrate was BBC-OH, as shown in FIG. 14, it was revealed that even the wild type had the decomposition activity, which was less effective than that of the HIS1 protein, though. Moreover, it was revealed that introduction of the Q140H mutation improved the activity to as high a level as that of the HIS1 protein. In addition, it was also revealed further introduction of the Y204F mutation further improved the activity.

In addition, although not shown in the figures, regarding the ZmHSL2 protein, it was also found that in the case where the substrate was sulcotrione, introduction of the Q140H mutation improved the activity.

<Introduction of Mutation in SbHSL1 Protein>

Regarding the SbHSL1 protein, in the case where the substrate was BBC-OH, as shown in FIG. 15, it was confirmed that even the wild type had the decomposition activity, which was less effective than that of the HIS1 protein, though. Moreover, it was revealed that introduction of the Q140H mutation improved the activity to as high a level as that of the HIS1 protein.

As described above, in the case where any of benzobicyclon hydrolysate (BBC-OH), tefuryltrione, sulcotrione, mesotrione, and tembotrione, or a 4-HPPD inhibitor of any of these was used as the substrate, it was revealed that substituting the amino acid at position 140 with a basic amino acid, particularly histidine, improved the decomposition activity of the HSL protein.

In addition, as shown in FIG. 9, it was also revealed that in the case where BBC-OH was used as the substrate, the addition of the L204 mutation or the addition of the F298 mutation further improved the decomposition activity; on the other hand, in the case where tefuryltrione, sulcotrione, or mesotrione was used as the substrate, the decomposition activity did not change or decreased.

Moreover, it was revealed that the introduction of mutation into three portions F140, L204, and F298 improved all of the decomposition activities against BBC-OH, tefuryltrione, sulcotrione, mesotrione, and tembotrione to as high a level as that of the HIS1 protein.

Example 5

Evaluation on Resistance of OsHSL1 Mutant Against 4-HPPD Inhibitor in Plant (*Arabidopsis thaliana*)

OsHSL1 mutants (a five-site mutant of V118I, F140H, L204F, S229T, and F298L, a four-site mutant of F140H, L204F, S229T, and F298L, and a three-site mutant of F140H, L204F, and F298L) to which the decomposition activity against benzobicyclon hydrolysate (BBC-OH) was added in the above-described in vitro system were expressed in plants, and whether the resistance to benzobicyclon (BBC) in the form of a prodrug were enhanced was evaluated by a method described below.

Specifically, first, genes coding for each OsHSL1 mutant was prepared in the same manner as described above. Then, each gene was linked to downstream of the 35S promoter and was cloned together with a kanamycin-resistance gene cassette in the binary vector. The vectors thus obtained were each introduced into *Arabidopsis thaliana* (Columbia) by a floral dip method and transformed. T0 seeds thus obtained were seeded in a kanamycin-containing medium and resistant individuals were obtained. Then, individuals determined to have the gene introduced therein were selected, from which T1 seeds were collected and seeded in a BBC-containing growth medium. The growth conditions of these were observed. The results thus obtained are shown in FIG. 10.

Figure 10:
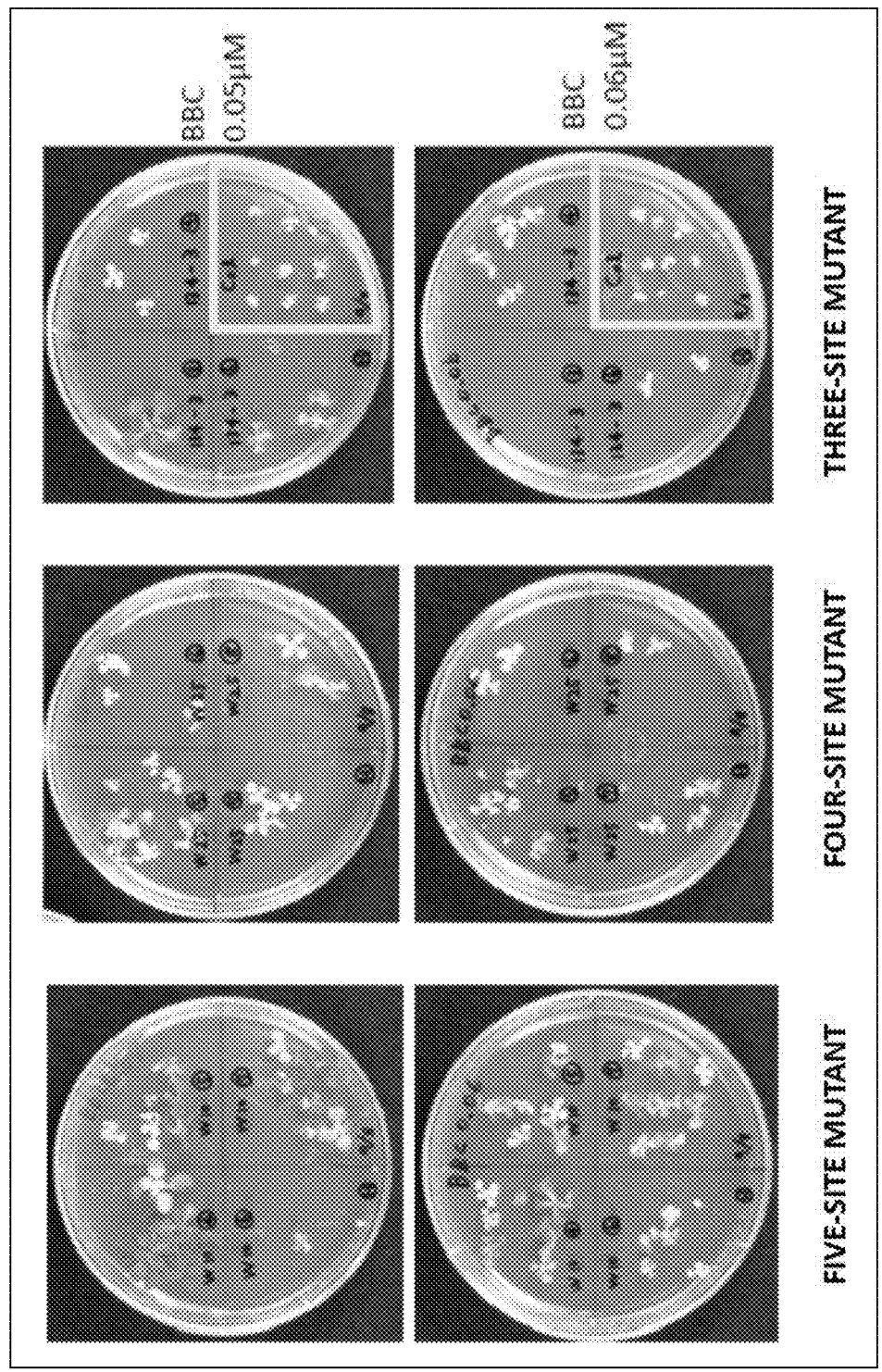
FIG. 10 is photographs showing results of observing growth conditions of *Arabidopsis thaliana* in which OsHSL1 protein mutants (the five-site mutant of V118I, F140H, L204F, S229T, and F298L, the four-site mutant of F140H, L204F, S229T, and F298L, the three-site mutant of F140H, or L204F, and F298L) are expressed in agar growth media containing 0.05 µM or 0.06 µM benzobicyclon (BBC), where lower right quarters in the respective two plates on the right side show results of observing growth conditions of *Arabidopsis thaliana* which was not transformed and arrows indicate individuals that took in green.

As is clear from the results shown in FIG. 10, in any of the mutants, it was observed that individuals that took in green appeared under conditions in which non-recombinant control individuals were whitened. To be more specific, apparent resistance against BBC was observed in one out of 3 lines of *Arabidopsis thaliana* in which the three-site mutant was expressed, was observed in one out of 4 lines of *Arabidopsis thaliana* in which the four-site mutant was expressed, and was observed in three out of 4 lines of *Arabidopsis thaliana* in which the five-site mutant was expressed. In other words, it was confirmed that expressing the OsHSL1 mutant provided with the 4-HPPD inhibitor decomposition activity in a plant enhanced the resistance of the plant against the 4-HPPD inhibitor.

In addition, a single-site mutant of F140H or a single-site mutant of F298L was expressed in *Arabidopsis thaliana*, and it was evaluated whether the resistance against sulcotrione (the concentration of sulcotrione contained in the growth medium: 0.1 µM), mesotrione (the concentration of mesotrione contained in the growth medium: 0.1 µM), or tembotrione (the concentration of tembotrione contained in the growth medium: 0.05 µM) was enhanced in the same manner as described above.

As a result, although not shown in the figures, in the single-site mutant of F140H, it was observed that individuals that took in green appeared under conditions in which non-recombinant control individuals (HSL1 (wild type)) were whitened, and the efficacy of the mutation in improvement of the resistance against the agent was confirmed as in the case of the above-described in vitro system. On the other hand, in the single-site mutant of F298L, no improvement of the resistance against the agent was confirmed.

Example 6

Evaluation on Resistance of OsHSL1 Mutant to 4-HPPD Inhibitor in Plant (Rice)

Next, the efficacy of the F140H mutation was confirmed using rice. Specifically, first, an mHSL1 gene obtained by modifying phenylalanine at position 140 in a rice HSL1 cDNA gene to histidine was prepared. Subsequently, the mutated gene or an HSL1 gene in which the mutation was not introduced was linked to downstream of the 35S promoter and was cloned together with a hygromycin-resistance gene expression cassette in the binary vector. Then, these vectors were each introduced into a benzobicyclon-susceptible cultivar "Yamadawara" by an *agrobacterium* method and recombinant rice was grown.

The recombinant rice (T1) seeds thus produced and the seeds of the original cultivar "Yamadawara" were tested and seeded on an MS medium containing 0.25 μM BBC in a sterile manner and grown at 30° C. in a bright place for 8 days. Results thus obtained are shown in FIG. 11.

Figure 11:
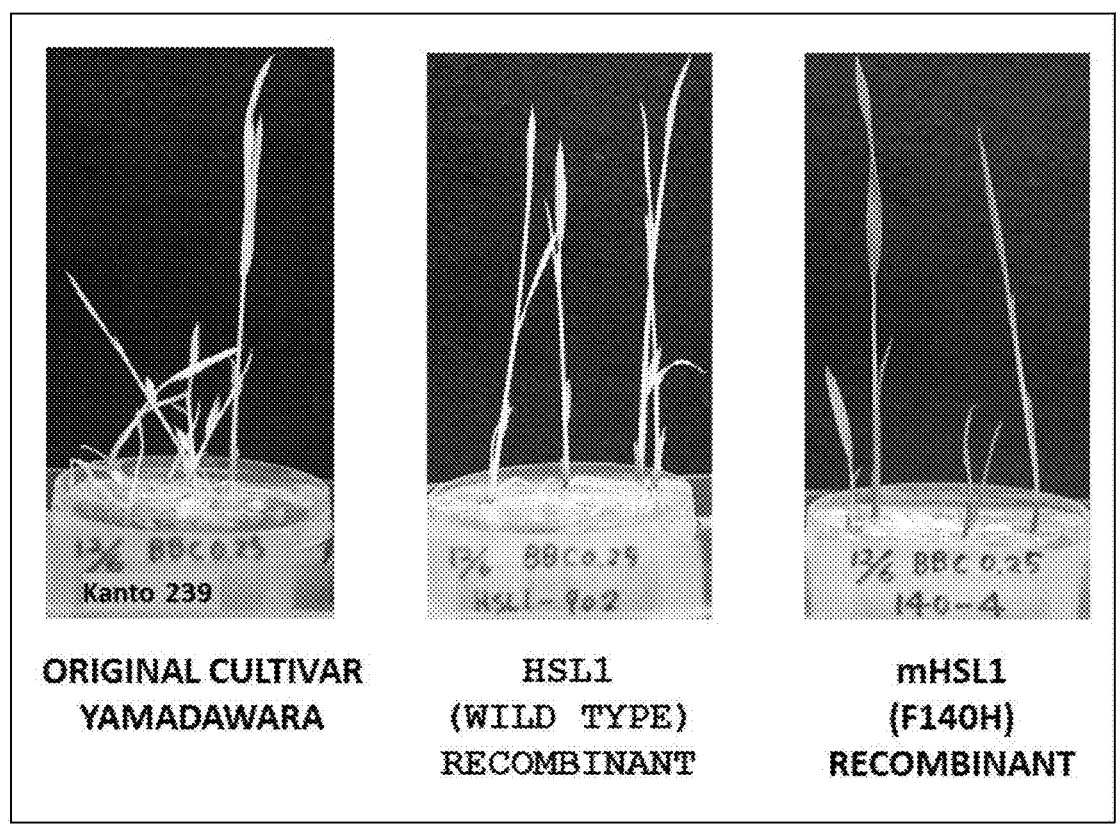
FIG. 11 is photographs showing results of observing growth conditions of Yamadawara, which is a benzobicyclon-susceptible rice, Yamadawara in which a wild type of the OsHSL1 protein is expressed (in FIG. 11, "HSL1 (wild type) recombinant"), and Yamadawara in which a mutant (the single-site mutant of F140H) of the OsHSL1 protein is expressed (in FIG. 11, "mHSL1 (F140H) recombinant"), in BBC-containing MS media.

As is clear from the results shown in FIG. 11, in the mHSL1 recombinant rice, individuals that took in green appeared under conditions in which the non-recombinant control (original cultivar) and non-modified HSL1 recombinant rice were whitened (Note that since it is a hetero-population, individuals that were whitened also appeared. However, in this experiment, null individuals generated due to gene separation were removed.

In this way, it was confirmed that in rice as well, BBC resistance was added to the BBC-susceptible cultivar by overexpressing the mHSL1 (F140H) gene.

INDUSTRIAL APPLICABILITY

As described so far, according to the present invention, it is possible to increase the catalytic activity of an HSL protein to oxidize a 4-HPPD inhibitor in a 2-oxoglutarate-dependent manner by mutating, in the protein, position 140 to a basic amino acid. Then, in the present invention, it is also possible to produce a plant with increased resistance to a 4-HPPD inhibitor by utilizing such a method for producing an HSL protein with increased catalytic activity to oxidize a 4-HPPD inhibitor in a 2-oxoglutarate-dependent manner.

Moreover, as described above, based on the finding that an amino acid at position 140 in an HSL protein is an amino acid that affects the catalytic activity, according to the present invention, it is also possible to determine resistance of a test plant to a 4-HPPD inhibitor by detecting a nucleotide which codes for an amino acid at position 140 in an HSL gene of the test plant. In addition, according to the present invention, it is also possible to provide a method for breeding a plant having increased resistance to a 4-HPPD inhibitor, utilizing the above method.

Therefore, when plants having increased resistance to a 4-HPPD inhibitor of the present invention are used and cultivated, the weed control can be efficiently carried out in cultivation paddy fields or cultivation fields. In addition, the method for determining resistance of a plant to a 4-HPPD inhibitor of the present invention can be utilized, for example, to reduce a germination risk of self-sown seeds from the previous year in crop rotation cycles. In this manner, the present invention can contribute greatly to stable production and yield increase of useful plants.

Sequence Listing Free Text

SEQ ID NO: 23
<223> catalytic triad
<223> Xaa at position 2 may be any amino acid.
<223> Xaa at position 3 is aspartic acid or glutamic acid.
<223> Xaa at position 4 may be any amino acid.
SEQ ID NOs: 24 to 43
<223> sequence of artificially synthesized primers

---

The invention claimed is:

1. A method for producing a mutant HSL (4-Hydroxyphenylpyruvate dioxygenase Inhibitor sensitive 1-Like) protein with increased catalytic activity to oxidize a 4-HPPD (4-hydroxyphenylpyruvate dioxygenase) inhibitor in a 2-oxoglutarate-dependent manner, said method comprising:
expressing, in a plant cell, a mutant HSL protein, wherein said mutant HSL protein is a mutant of a wild type HSL protein, wherein said wild type HSL protein comprises an amino acid sequence having at least 95% sequence identity to the amino acid sequence of any one of SEQ ID NO: 4, 18, 20, or 22,
wherein the mutant HSL protein comprises the substitution of a phenylalanine or glutamine to a basic amino acid at a position corresponding to position 140 of SEQ ID NO: 4, and optionally further comprises one or both of the following substitutions: (1) a leucine or tyrosine to phenylalanine at a position corresponding to position 204 of SEQ ID NO: 4, and (2) a phenylalanine to leucine at a position corresponding to position 298 of SEQ ID NO: 4, wherein the basic amino acid is lysine, histidine or arginine, and
wherein said mutant HSL protein has no more than three substitutions relative to the wild type HSL protein.

2. A method for producing a plant with increased resistance to a 4-HPPD inhibitor, comprising the steps of:
(I) mutating, in a plant cell, an endogenous gene encoding a wild type HSL protein, wherein said wild type HSL protein comprises an amino acid sequence having at least 95% sequence identity to the amino acid sequence of any one of SEQ ID NO: 4, 18, 20, or 22,
wherein said mutating produces a mutated gene that encodes a mutant HSL protein, wherein the mutant HSL protein comprises the substitution of a phenylalanine or glutamine to a basic amino acid at a position corresponding to position 140 of SEQ ID NO: 4, and optionally further comprises one or both of the following substitutions: (1) a leucine or tyrosine to phenylalanine at a position corresponding to position 204 of SEQ ID NO: 4, and (2) a phenylalanine to leucine at a position corresponding to position 298 of SEQ ID NO: 4, wherein the basic amino acid is lysine, histidine or arginine, and
wherein said mutant HSL protein has no more than three substitutions relative to the wild type HSL protein; and
(II) regenerating a plant from the plant cell, wherein the regenerated plant comprises said mutated gene.

* * * * *